US006592573B2

(12) United States Patent
Castañeda et al.

(10) Patent No.: US 6,592,573 B2
(45) Date of Patent: *Jul. 15, 2003

(54) THROUGH-PORT HEART STABILIZATION SYSTEM

(75) Inventors: Javier E. Castañeda, Miami, FL (US); Jose Luis Francese, Springs, FL (US); Matthew A. Palmer, Miami, FL (US); Ralph de la Torre, Charlestown, MA (US)

(73) Assignee: Popcab, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/893,099

(22) Filed: Jun. 27, 2001

(65) Prior Publication Data

US 2002/0042606 A1 Apr. 11, 2002

Related U.S. Application Data

(63) Continuation-in-part of application No. 09/686,696, filed on Oct. 11, 2000, now Pat. No. 6,464,691, and a continuation-in-part of application No. 09/686,530, filed on Oct. 11, 2000, now Pat. No. 6,464,690, and a continuation-in-part of application No. 09/733,493, filed on Dec. 8, 2000, and a continuation-in-part of application No. 09/733,498, filed on Dec. 8, 2000, and a continuation-in-part of application No. 09/733,503, filed on Dec. 8, 2000, now Pat. No. 6,355,028, and a continuation-in-part of application No. 09/741,387, filed on Dec. 20, 2000.

(51) Int. Cl.[7] .............................................. A61B 17/00

(52) U.S. Cl. .......................... 606/1; 604/513; 604/539; 604/174; 604/164.04; 606/108

(58) Field of Search ................................ 600/201, 208, 600/215, 210, 235; 606/1, 108; 604/513, 533, 539, 174, 164.04

(56) References Cited

U.S. PATENT DOCUMENTS

| 4,143,652 A | 3/1979 | Meier et al. .................. 128/20 |
| 4,492,229 A | 1/1985 | Grunwald ..................... 128/303 |
| 4,635,636 A | 1/1987 | Goldstein .................... 128/334 |
| 5,104,383 A | 4/1992 | Shichman .................... 604/167 |
| 5,147,316 A | 9/1992 | Castillenti ................... 604/164 |
| 5,176,648 A | 1/1993 | Holmes et al. ............. 604/164 |
| 5,195,506 A | 3/1993 | Hulfish ........................ 128/20 |
| 5,300,087 A | 4/1994 | Knoepfler ................... 606/207 |
| 5,364,367 A | 11/1994 | Banks et al. ................ 604/174 |

(List continued on next page.)

FOREIGN PATENT DOCUMENTS

| CA | 2216893 | 7/1997 |
| DE | 29707567 U1 | 7/1997 |
| EP | 0336 526 A1 | 10/1989 |

(List continued on next page.)

OTHER PUBLICATIONS

Pilling Surgical Instruments 1993 catalogue, p. 304, designs for Miscellaneous Heart Instruments.

(List continued on next page.)

Primary Examiner—Linda C. M. Dvorak
Assistant Examiner—Jocelyn Ram
(74) Attorney, Agent, or Firm—Gordon & Jacobson, P.C.

(57) ABSTRACT

A heart stabilizer includes a shaft and two articulating arms coupled to a distal end of the shaft. At the end of each arm is a rotatable foot adapted to be angled relative to the heart wall contour and apply pressure against the wall of the heart to effectively eliminate motion of the heart wall between the feet. The stabilizer is adapted to be collapsible (foldable) to be inserted through the port device and locked longitudinally relative thereto. The stabilizer is also adapted to be deployed into an open configuration and then manipulated by actuation of a proximal control and actuation handle into a selected orientation.

43 Claims, 64 Drawing Sheets

U.S. PATENT DOCUMENTS

| | | | |
|---|---|---|---|
| 5,374,277 A | 12/1994 | Hassler | 606/207 |
| 5,375,588 A | 12/1994 | Yoon | 128/4 |
| 5,389,081 A | 2/1995 | Castro | 604/167 |
| 5,391,156 A | 2/1995 | Hildwein et al. | 604/174 |
| 5,407,427 A | 4/1995 | Zhu et al. | 604/26 |
| 5,445,615 A | 8/1995 | Yoon | 604/96 |
| 5,452,733 A | 9/1995 | Sterman et al. | 128/898 |
| 5,472,429 A | 12/1995 | Yoon | 604/178 |
| 5,476,479 A | 12/1995 | Green et al. | 606/205 |
| 5,490,843 A | 2/1996 | Hildwein et al. | 604/164 |
| 5,501,698 A | 3/1996 | Roth | 606/205 |
| 5,540,648 A | 7/1996 | Yoon | 600/114 |
| 5,545,179 A | 8/1996 | Williamson, IV | 606/213 |
| 5,571,072 A | 11/1996 | Kronner | 600/102 |
| 5,582,577 A | 12/1996 | Lund et al. | 600/204 |
| 5,613,937 A | 3/1997 | Garrison et al. | 600/201 |
| 5,637,097 A | 6/1997 | Yoon | 604/174 |
| 5,653,718 A | 8/1997 | Yoon | 606/148 |
| 5,685,857 A | 11/1997 | Negus et al. | 604/170 |
| 5,688,247 A | 11/1997 | Haindl et al. | 604/175 |
| 5,707,362 A | 1/1998 | Yoon | 604/164 |
| 5,717,869 A | 2/1998 | Morejon | 604/174 |
| 5,725,553 A | 3/1998 | Moenning | 606/213 |
| 5,735,290 A | 4/1998 | Sterman et al. | 128/898 |
| 5,749,892 A | 5/1998 | Vierra et al. | 600/204 |
| 5,782,813 A | 7/1998 | Yoon | 604/174 |
| 5,799,661 A | 9/1998 | Boyd et al. | 128/898 |
| 5,807,243 A * | 9/1998 | Vierra et al. | 128/898 |
| 5,817,062 A | 10/1998 | Flom et al. | 604/174 |
| 5,820,555 A | 10/1998 | Watkins, III et al. | 600/204 |
| 5,823,946 A | 10/1998 | Chin | 600/204 |
| 5,836,913 A | 11/1998 | Orth et al. | 604/107 |
| 5,865,730 A | 2/1999 | Fox et al. | 600/228 |
| 5,865,809 A | 2/1999 | Moenning et al. | 604/174 |
| 5,865,817 A | 2/1999 | Moenning et al. | 604/283 |
| 5,894,843 A | 4/1999 | Benetti et al. | 128/898 |
| 5,972,080 A | 10/1999 | Farascioni | 600/213 |
| 5,980,455 A | 11/1999 | Daniel et al. | 600/235 |
| 6,007,486 A * | 12/1999 | Hunt et al. | 600/201 |
| 6,015,378 A | 1/2000 | Borst et al. | 600/37 |
| 6,017,304 A | 1/2000 | Vierra et al. | 600/204 |
| 6,019,722 A | 2/2000 | Spence et al. | 600/210 |
| 6,027,476 A | 2/2000 | Sterman et al. | 604/96 |
| 6,033,362 A | 3/2000 | Cohn | 600/213 |
| 6,033,426 A | 3/2000 | Kaji | 606/213 |
| 6,036,641 A | 3/2000 | Taylor et al. | 600/231 |
| 6,039,725 A | 3/2000 | Moenning et al. | 606/1 |
| 6,045,536 A | 4/2000 | Meier et al. | 604/174 |
| 6,050,266 A * | 4/2000 | Benetti et al. | 128/898 |
| 6,056,689 A | 5/2000 | Lenox et al. | 600/217 |
| 6,056,766 A | 5/2000 | Thompson et al. | 606/185 |
| 6,063,021 A | 5/2000 | Hossain et al. | 600/37 |
| 6,110,187 A | 8/2000 | Donlon | 606/151 |
| 6,113,534 A | 9/2000 | Koros et al. | 600/213 |
| 6,123,370 A | 10/2000 | Furnish et al. | 600/235 |
| 6,139,492 A | 10/2000 | Vierra et al. | 600/204 |
| 6,193,652 B1 * | 2/2001 | Berky et al. | 600/201 |
| 6,383,134 B1 * | 5/2002 | Santilli | 600/205 |
| 6,394,951 B1 * | 5/2002 | Taylor et al. | 600/210 |
| 6,398,726 B1 * | 6/2002 | Ramans et al. | 600/228 |

FOREIGN PATENT DOCUMENTS

| | | |
|---|---|---|
| EP | 0356410 A1 | 2/1990 |
| EP | 0630629 A1 | 12/1994 |
| EP | 0791330 A2 | 8/1997 |
| EP | 0820721 A1 | 1/1998 |
| FR | 1019217 | 1/1953 |
| WO | WO87/04081 | 7/1987 |
| WO | WO93/09720 | 5/1993 |
| WO | WO/9421179 | 4/1994 |
| WO | WO94/14383 | 7/1994 |
| WO | WO95/01757 | 1/1995 |
| WO | WO95/15715 | 6/1995 |
| WO | WO95/17127 | 6/1995 |
| WO | WO 96/04854 | 2/1996 |
| WO | WO97/10753 | 3/1997 |
| WO | WO97/20524 | 6/1997 |
| WO | WO97/27807 | 8/1997 |
| WO | WO98/25549 | 6/1998 |
| WO | WO99/11201 | 3/1999 |

OTHER PUBLICATIONS

Article entitled "Left Anterior Descending Coronary Artery Grafting via Left Anterior Small Thoracotomy without Cardiopulmonary Bypass" by Calafiore et al., in the 1996 Journal, The Society of Thoracic Surgeons, pp. 1658–1665.

Article entitled "Coronary Artery Bypass without Cardiopulmonary Bypass" by Pfister et al, in the 1992 Journal, The Society of Thoracic Surgeons, pp. 1085–1092.

Article entitled "Snaring of the Target Vessel in Less Invasive Bypass Operations does not cause Endothelial Dysfunction", by Perrault et al., in the 1997 Journal, The Society of Thoracic Surgeons, pp. 751–755.

Article entitled "Triple Coronary Artery Revascularization on the Stabilized Beating Heart: Initial Experience", by Cartier et al., from the Department of Cardiovascular Surgery and the Dept. of Anesthesiology, Montreal Heart Institute, Sep. 19, 1997, pp. 283–288.

Article entitled "Direct Myocardial Revascularization by Saphenous Vein Graft" by Favaloro et al. in the Aug. 1970, vol. 10, Journal of The Society of Thoracic Surgeons, pp. 97–111.

Editorial entitled "Coronary Surgery without Cardiopulmonary bypass", in British Heart Journal, 1995;73:pp. 203–205.

Article entitled "A new retaratcor to aid in coronary artery surgery" by DelRossie et al., 2 pages, in The Annals of Thoracic Surgery, vol. 36, No. 1, Jul. 1983.

Article entitled "The Cardiac Rag– simple exposure of the heart" by Badellino et al., vol. 15, No. 2, 1988 in the Texas Heart Institute Journal, pp. 134–135.

Letter to the Editor in Archives of Surgery, vol. 115, No. 9, Sep. 1980, on "New Use for an Old Clamp", 4 pages.

J Cardiovasc Surgery, 30, 1989, pp. 996–997, Technical Comments article entitled "Internal mammary artery dissection: A three dimensional sternal retractor" by Roux et al.

Article entitled "Off–Bypass Coronary Grafting via Minithoracotomy using Mechanical Epicardial Stabilization", by Cremer et al., in the 1997 Journal, The Society of Thoracic Surgeons, pp. 579–583.

Article entitled "Single coronary bypass grafting– a comparison between minimally invasive "off pump" techniques and conventional procedures", by Bonatti et al., in the European Journal of Cardio–thoracic Surgery 17 (Suppl 1), 1998, pp. S7–S12.

Article entitled "Less Invasive Coronary Surgery: Consensus from the Oxford Meeting", by Westaby et al., in the 1996 Journal, The Society of Thoracic Surgeons, pp. 924–931.

Article entitled "Mini–Sternotomy for Coronary Artery Bypass Grafting", by Arom et al., in the 1996 Journal, The Society of Thoracic Surgeons, pp. 1271–1272.

Article entitled "Limited Access Myocardial Revascularization" by Cooley, in the Texas Heart Institute Journal, vol. 23, No. 2, 1996, pp. 81–84.

Letter to the Editor on Mini–Sternotomy for Coronary Artery Bypass Grafting by A. Cohen et al., 1996, pp. 1884–1885, Journal, The Society of Thoracic Surgeons.

Article entitled "Fabric Heart Retractor for Coronary Artery Bypass Operations" by Kazama et al. in the 1993 Journal, The Society of Thoracic Surgeons, pp. 1582–1583.

Article entitled "Minimally Invasive Coronary Artery Bypass Grafting" by Calafiore et al. in the 1996 Journal, The Society of Thoracic Surgeons, pp. 1545–1548.

Article entitled "Improved Visualization of the Internal Mammary Artery with a New Retractor System" by Pittman et al. in the 1989 Journal, The Society of Thoracic Surgeons, pp. 869–870.

Article entitled "A Modified Sternal Retractor" by Ancalmo et al. from the Dept. of Surgery, Alton Ochsner Medical Foundation and Ochsner Clinic, New Orleans, LA, Aug. 8, 1975., p. 174.

Article entitled "A Versatile Retractor For Use In Harvesting The Internal Mammary Artery And Performing Standard Cardiac Operations" by Phillips et al., in the J Thoracic Carciovasc Surg 1989, vol. 97, pp. 633–635.

Article entitled "Surgical Management of Diseased Intracavitary Coronary Arteries" by Ochsner et al. in The Annals of Thoracic Surgery, vol. 38, No. 4, Oct. 1984, pp. 356–362.

Article entitled "Technique of internal mammary–coronary artery anastomosis" by Green, in the Journal of Thoracic Surgery, vol. 78, 1979, pp. 455–459.

Article entitled "Graduated probes for coronary bypass surgery" by Parsonner et al., in the Journal of Thoracic and Cardiovascular Surgery, vol. 68, No. 3, Sep. 1974, pp. 424–427.

Article entitled "A Modified Sternal Retractor for Exposure of the Internal Mammary Artery" by McKeown et al., in the Society of Thoracic Surgeons, 1980, p. 619.

Article entitled "A New Concept in Sternal Retraction: Application for Internal Mammary Artery Dissection and Valve Replacement Surgery" by Chaux et al., in the Annals of Thoracic Surgery, vol. 42, Oct. 1986, pp. 473–474.

Article entitled "Cardiac Retractor for Coronary Bypass Operations" by Rousou et al., in The Society of Thoracic Surgeons, pp. 877–878.

Article entitled A New Retractor to Aid in Coronary Artery Surgery: by DelRossi et al., in the in the Annals of Thoracic Surgery, vol. 36, No. 1, Jul. 1983.

Article entitled "New Helper Instrument in Cardiac Surgery" by Roux et al., in the Society of Thoracic Surgeons, 1989, pp. 505–596.

Article entitled "Aortic Spoon–Jaw Clamp for Aorto–Saphenous Vein Anastomosis" by Robicsek, in the Journal of Card Surg, 1995; vol. 10, pp. 583–585.

Article entitled "Techniques of dissecting the internal mammary after using the Moussali bar" by Hasan et al. , the European J Cardio–thorac Surg, 1990, vol. 4, pp. 571–572.

Article entitled "Self–Retaining Epicardial Retractor For Aortocoronary Bypass Surgery" by Parsonnet et al., in the Journal of Thoracic and Cardiovascular Surgery, 1979, pp. 629–630.

Article entitled Coronary Artery bypass Grafting without Cardiopulmonary Bypass and Without Interruption of Native Coronary Flow Using a Novel Anastomosis Site Restraining Device ("Octopus"), by Borst et al., JACC, vol. 27, No. 6, May 1996, pp. 1356–1364.

Article entitled "A New Internal Mammary Artery Retractor" by Bugge, in the Thorac.cardiovasc.Surgeon, vol. 38, 1990, pp. 316–317.

Article entitled "A Simple, Inexpensive Method of Heart Retraction During Coronary Artery Bypass Surgery" by Angelini, in the Ann Thorac Surg, vol. 46, pp. 246–247, Aug. 1988.

Article entitled A New Device for Exposing the Circumflex Coronary Artery: by Matsuura et al., in the Society of Thoracic Surgeons, 1995, pp. 1249–1250.

Article entitled "Application of a Special vasal devaricator during coronary surgery" by Vigano, in the Minerva Cardioangiologica, Jul. 1975, pp. 370–371.

Translation of "Heart Retractor for Use in Anastomosis in Coronary Artery By–pass Surgery" by Eguchi, from the Japanese Journal of Thoracic Surgery, vol. 40, No. 1, 1987, 4 pages.

Japanese article (title translated) on "A Special Retractor for Stabilizing the Heart During Circumflex Coronary Grafting" by Eguchi, 1987, 2 pages.

Article entitled "Revascularization of the Circumflex Coronary Artery—A new Instrument and a Technical Method–" by Murata, in the Japanese Journal of Thoracic Surgery, 1989, vol. 42, No. 2, 6 pages.

* cited by examiner

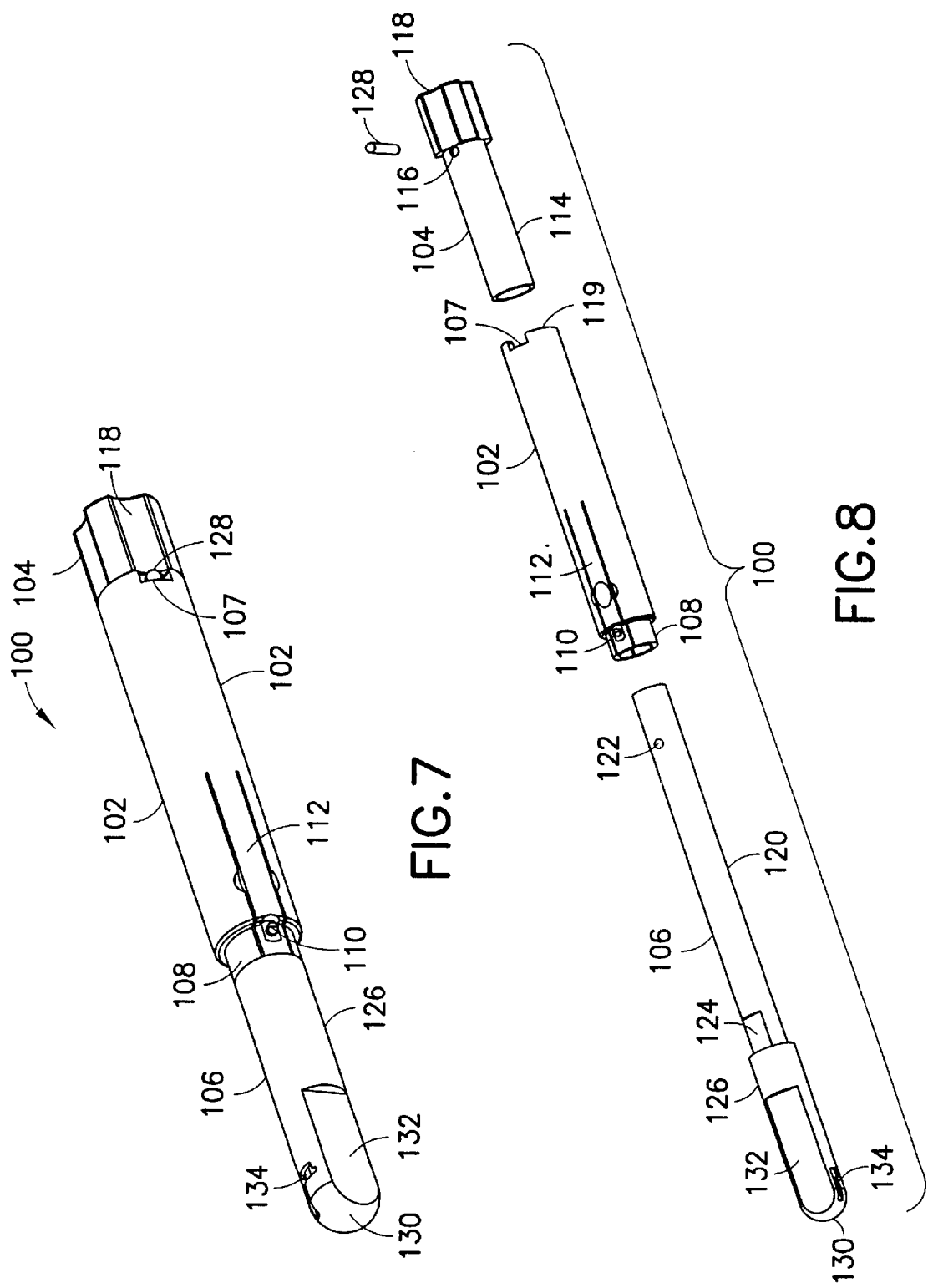

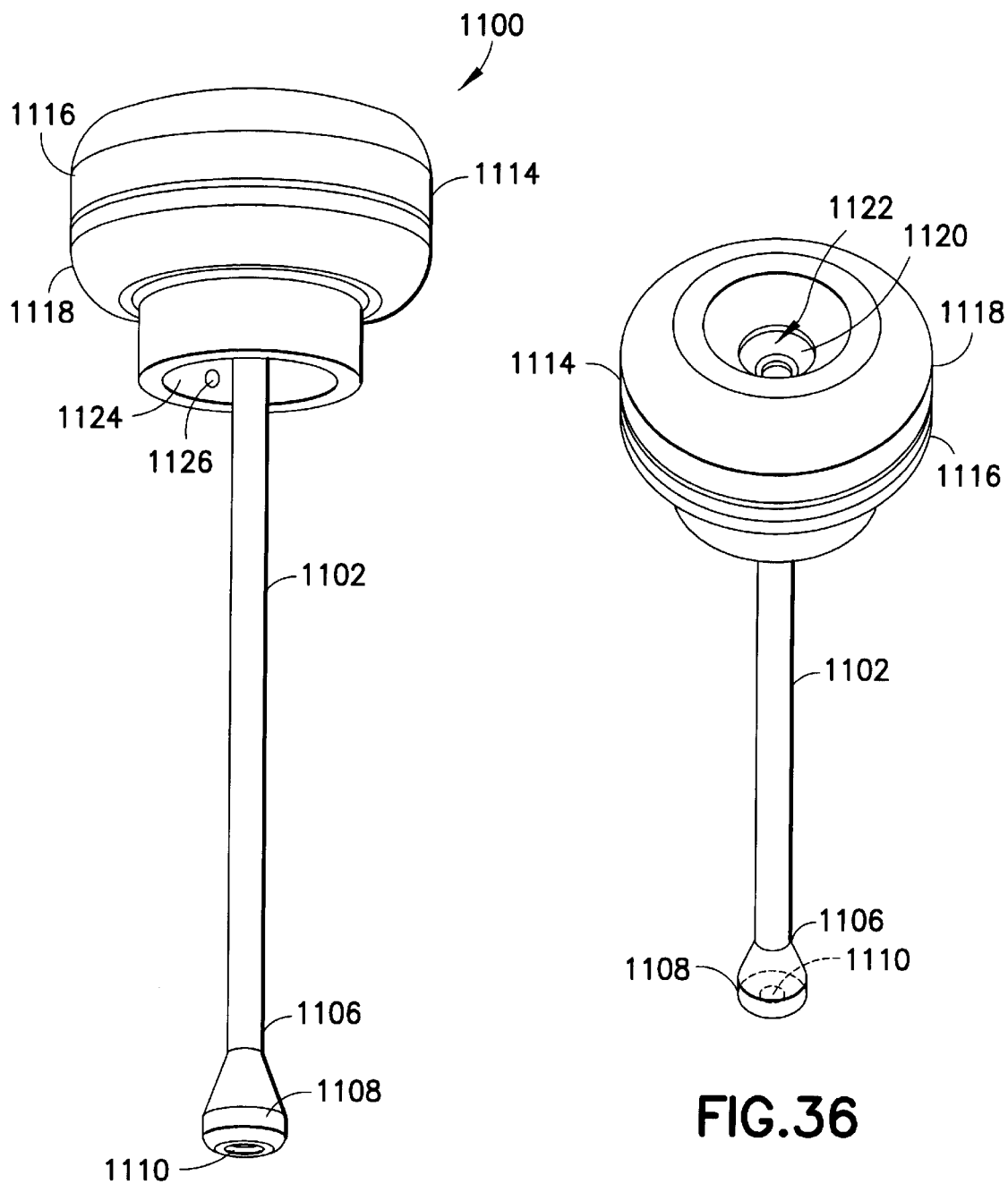

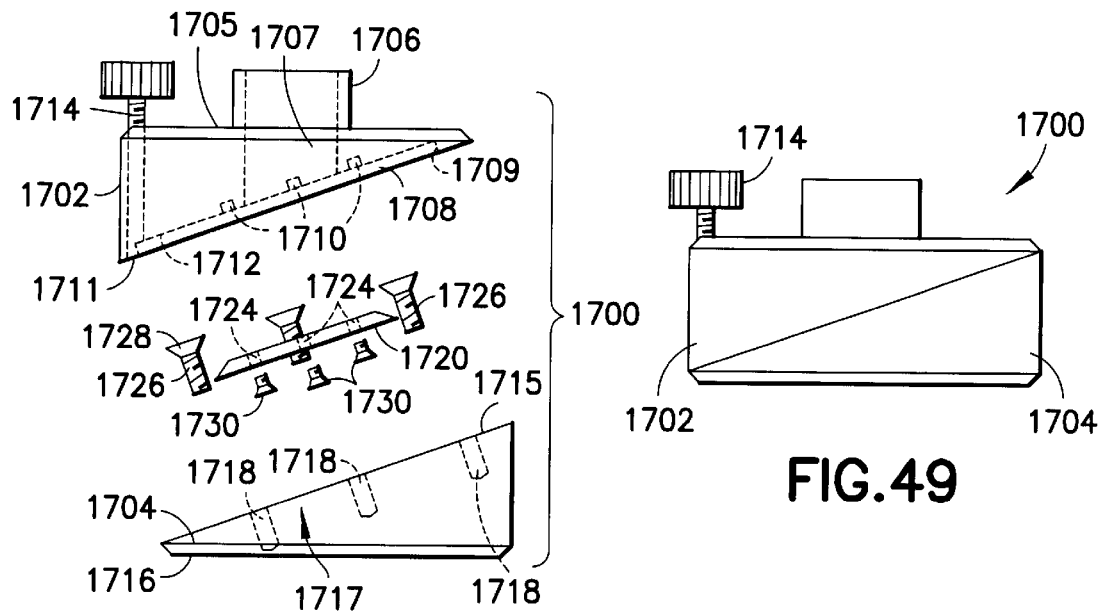
FIG.49
FIG.50
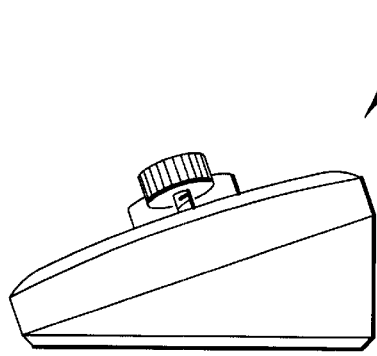
FIG.51
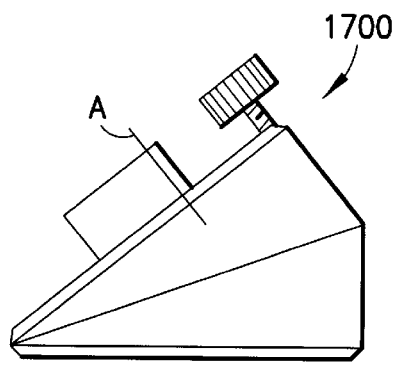
FIG.52

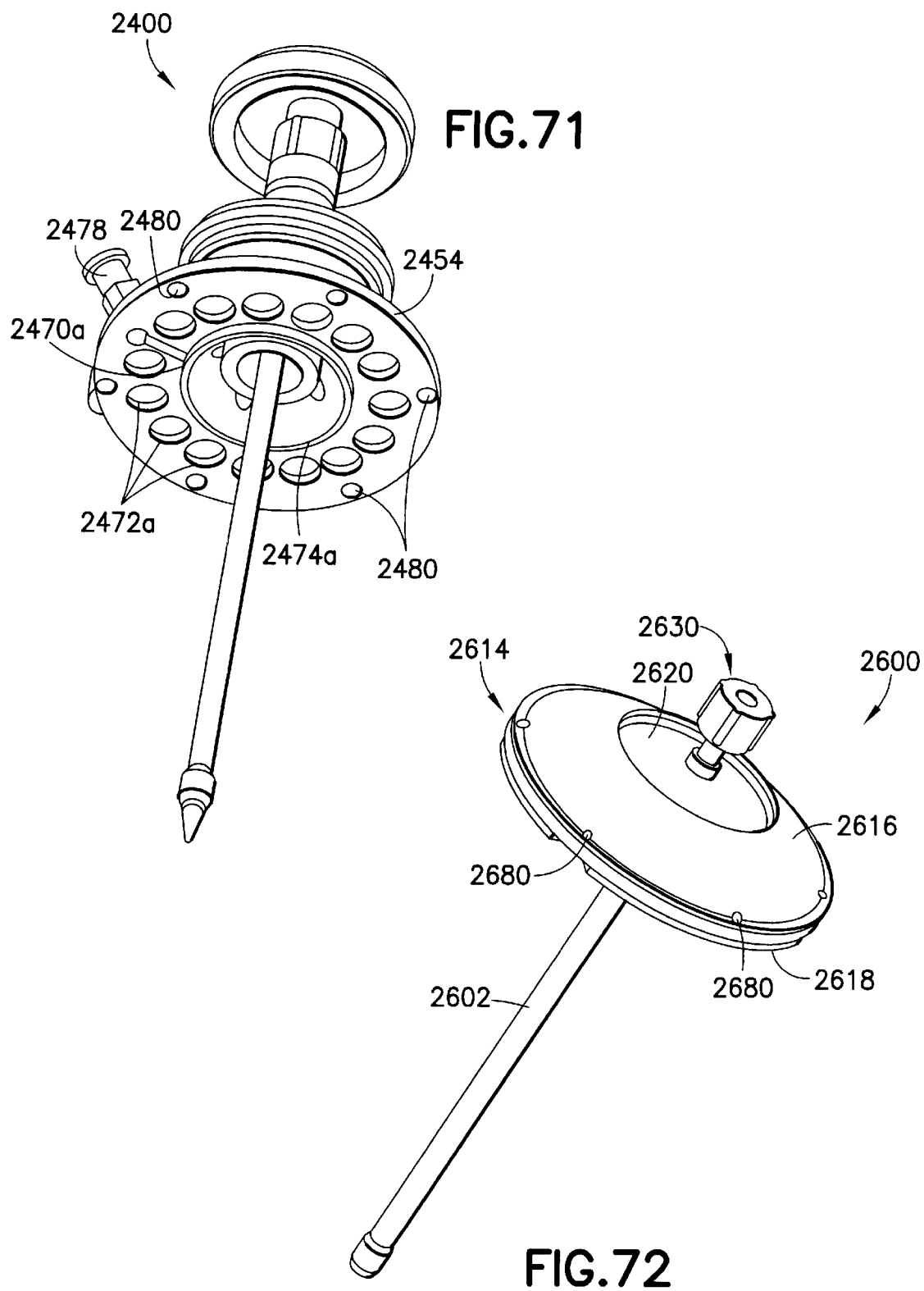

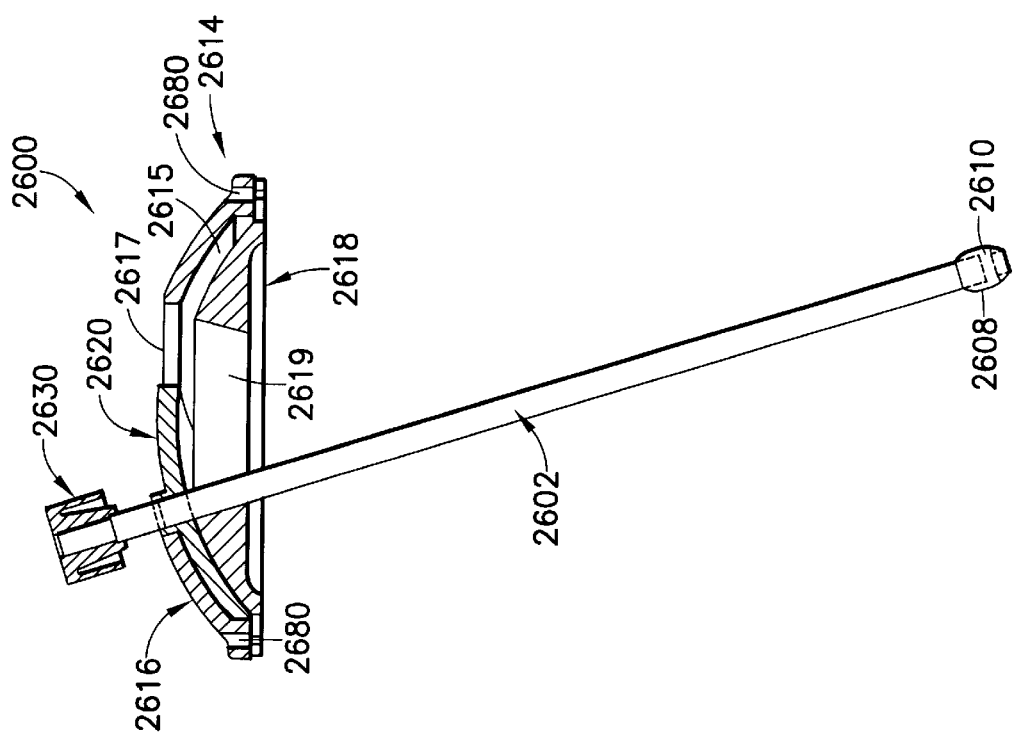
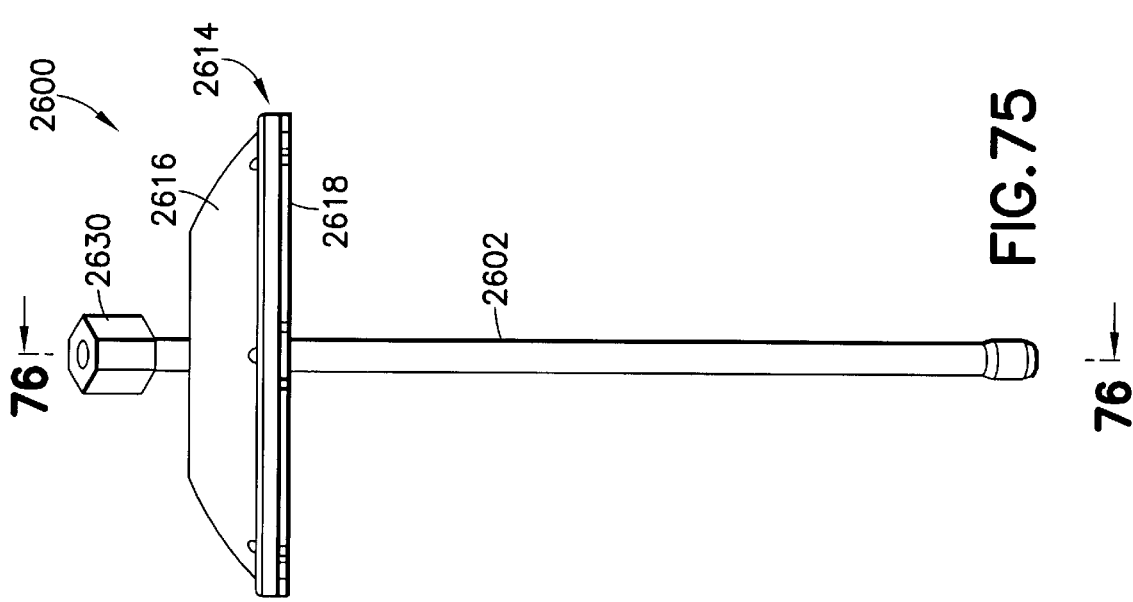

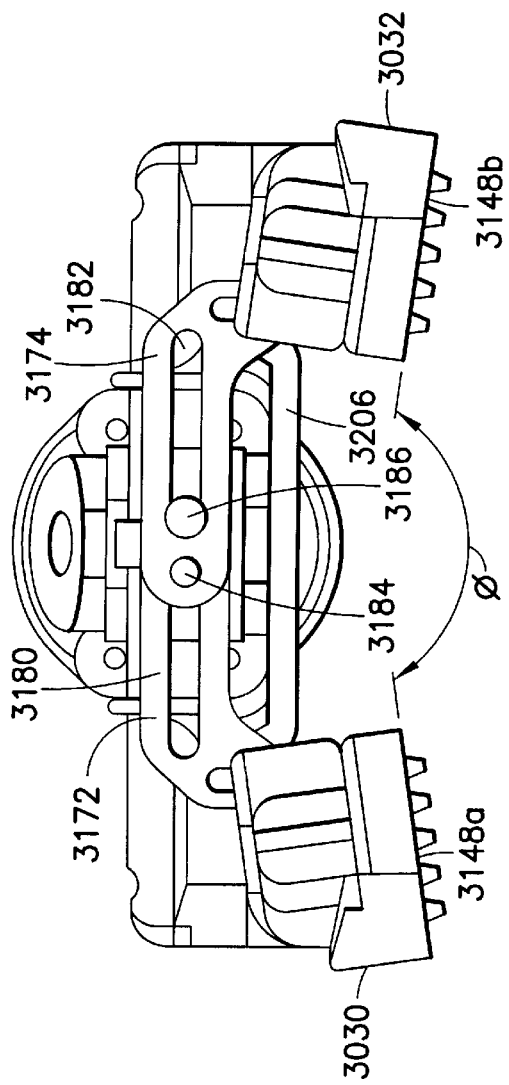
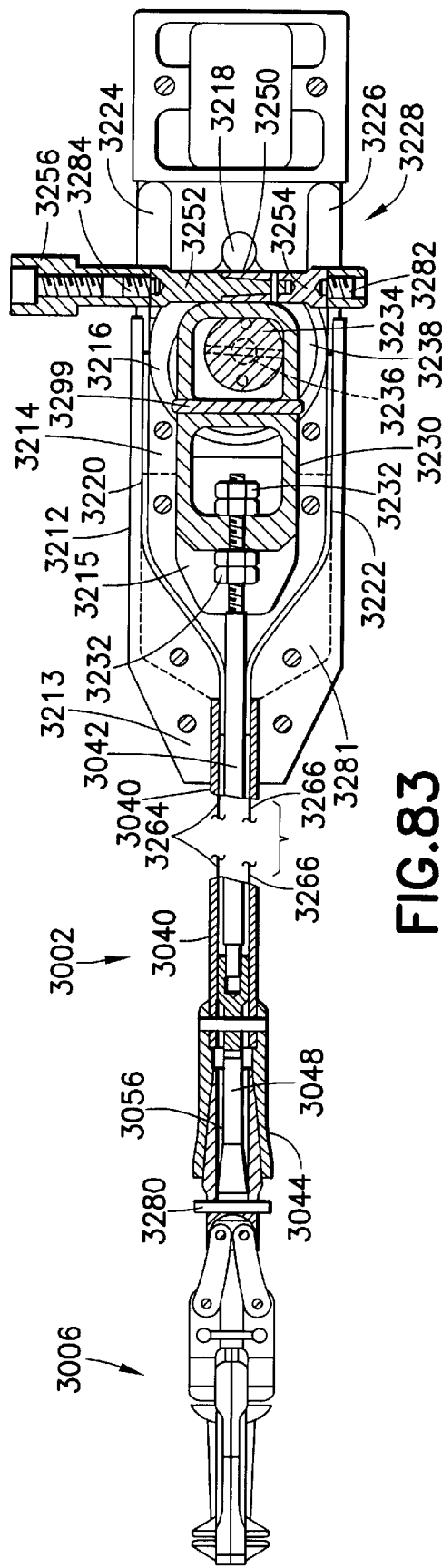
FIG. 81
FIG. 83

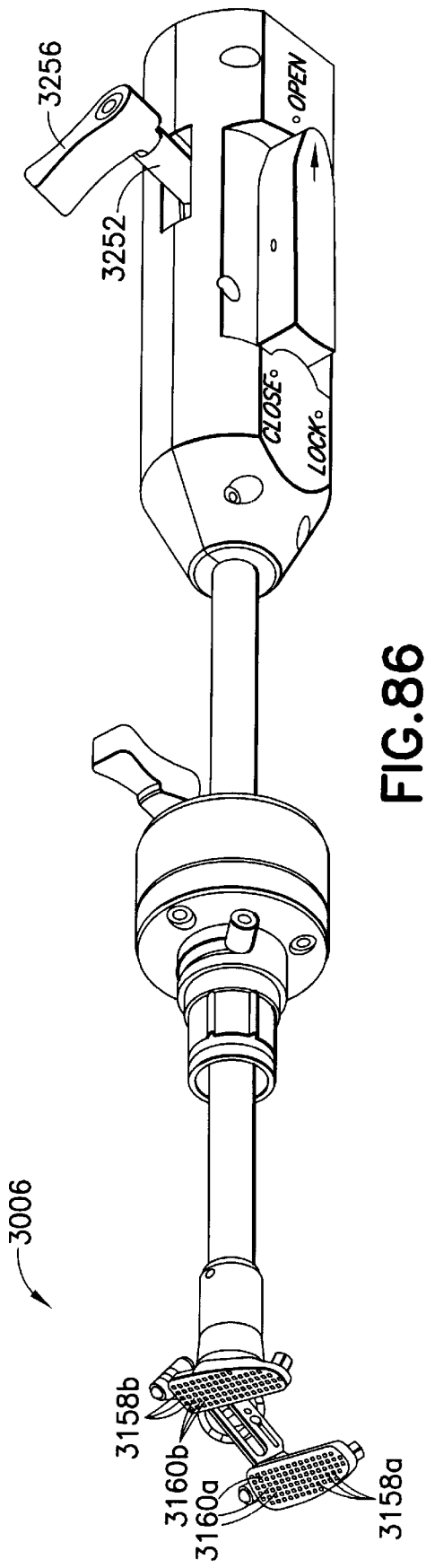
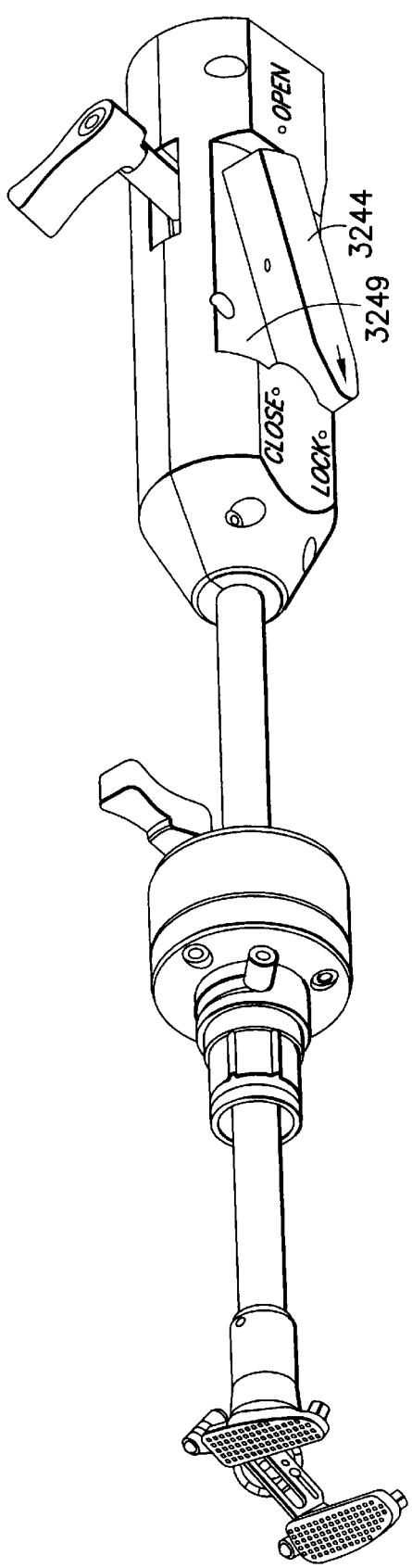
FIG. 86
FIG. 87

THROUGH-PORT HEART STABILIZATION SYSTEM

This application is a continuation-in-part of U.S. Ser. No. 09/686,696, filed Oct. 11, 2000 now U.S. Pat. No. 6,464,691 and entitled "Port Device for Port Off-Pump Beating Heart Coronary Artery Bypass Surgery System", U.S. Ser. No. 09/686,530, filed Oct. 11, 2000 now U.S. Pat. No. 6,464,690 and entitled "Port Off-Pump Beating Heart Coronary Artery Bypass Heart Stabilization System", U.S. Ser. No. 09/733,493, filed Dec. 8, 2000 and entitled "System for Performing Port Off-Pump Beating Heart Coronary Artery Bypass Surgery", U.S. Ser. No. 09/733,498, filed Dec. 8, 2000 and entitled "Method of Performing Port Off-Pump Beating Heart Coronary Artery Bypass Surgery", U.S. Ser. No. 09/733,503, filed Dec. 8, 2000 now U.S. Pat. No. 6,355,028 and entitled "Stable Port Device for Port Off-Pump Beating Heart Coronary Artery Bypass Surgery", and U.S. Ser. No. 09/741,387, filed Dec. 20, 2000 and entitled "Instrument Stabilizer for Through-the-Port Surgery", each which is hereby incorporated by reference herein in its entirety.

BACKGROUND OF THE INVENTION

1. Field of the Invention

This invention relates broadly to surgical instruments and systems. More particularly, this invention relates to heart stabilizers for stabilizing the coronary artery. More particularly, the invention relates to such stabilizing being adapted to pass through a port during the surgery.

2. State of the Art

Substantially all coronary artery bypass (CAB) procedures are performed via an open chest method. In the procedure, the chest is opened through an incision in the middle of the chest, called a sternotomy, and the ribs are retracted and held stably open with a retractor. This provides a sufficient amount of access to the heart. The heart is then arrested and the blood flow is rerouted through a heart-lung machine. The bypass procedure is then performed, and once complete, the heart is then restarted and blood is permitted to flow through the "bypass". While this procedure is the norm, it is far from desirable. First, arresting the heart is a dangerous procedure and can lead to serious complications and even death. Second, the procedure requires a sternotomy, which is painful and traumatic. Because of this incision the recovery time is relatively long and the patient is left with a permanent large scar.

More recently, some surgeons have performed coronary artery bypass surgery on a beating heart. The chest is opened via a sternotomy and retracted. Using a device called a heart stabilizer, the surgical site on the heart is essentially immobilized for suturing. The heart stabilizer is typically anchored to the retractors which are in turn anchored to the walls of the chest at the site of the incision. Direct access to the surgical site as well as immobilization of the surgical site are key to the surgery. These factors allow the surgeon to perform a suture or other operation with precision. While the methodology is effective and eliminates the potential complications of arresting the heart, the drawbacks associated with the sternotomy remain.

It has recently been proposed by others to perform a closed chest bypass procedure on the beating heart. However, the proposal has not been followed by any concrete directions on how to satisfactorily perform the procedure. In addition, the inventors of the present application have recognized that the closed chest procedure has a number of hurdles to overcome. First, it is necessary to stabilize the heart such that the location requiring the bypass does not significantly move during the procedure. Second, while open chest procedure are accompanied by a retractor and instrument supporting framework, in a closed chest procedure, there is no such framework for holding the instruments required for the procedure. In addition, there is no suitable stable port device adapted to securely support instruments passing therethrough. Third, when performing any surgery through a port, the instruments used to work at the surgical site are relatively long compared to open chest instruments. The distance from the surgeons's hand to the tip of the instrument where the work is being performed can be many times greater than in conventional surgery. This increase in length amplifies normal hand tremor and any errors in motion.

SUMMARY OF THE INVENTION

It is therefore an object of the invention to provide a less traumatic instrument access to the surgical site.

It is another object of the invention to provide a port device which is easy to insert into the body, and particularly into the chest wall.

It is a further object of the invention to provide a port device with a high degree of stability.

It is an additional object of the invention to provide a heart stabilizer which can be inserted through the port device and which is adapted to stabilize a portion of a beating heart such that coronary artery bypass surgery can be performed on the portion of the heart.

It is also an additional object of the invention to provide a heart stabilizer which can be manipulated via a proximal handle external of the port device.

It is still another object of the invention to provide an instrument stabilization system which minimizes unwanted motion of the tips of instrument performing the procedure.

It is still a further object of the invention to provide an instrument stabilization system which can be coupled to the port device.

It is yet another object of the invention to provide a system of components which cohesively operates together to facilitate port off-pump coronary artery bypass surgery on a beating heart.

It is yet a further object of the invention to provide a method of performing port off-pump coronary artery bypass surgery on a beating heart.

In accord with these objects, which will be discussed in detail below, a system for performing port off-pump beating heart coronary artery bypass surgery is provided. The system includes three primary subsystems: a port device, a heart stabilizer, and an instrument stabilizer.

The port device is insertable between the ribs of the patient and functions as an entry way for each instrument necessary for the procedure, e.g., optics, graspers, needle holders, suction/irrigation tubes, stabilizers. According to a currently preferred embodiment, the port device includes a tubular port body having a plurality of circumferential grooves along its length, a slit ball provided about the port body and having ratchet springs which engage within the grooves of the port body, and a base defining a socket in which the slit ball is provided. The base includes a clamping system which compresses the ball to lock the ball at a selected orientation within the socket and also immobilizes the port body relative to the ball. The distal end of the port body includes a pair of swivels rotatably attached thereto. A removable obturator extends within the port body and can be manipulated to cause the swivels to rotate between a closed position (in which the swivels are oriented substantially parallel to the axis of the port body), and an open position (in which the swivels are directed outward from the port body and form a crossbar) and back again. The port body is sized to be inserted through a pair of ribs in a chest wall of a patient.

In another embodiment, the proximal portion of the tubular body includes a plurality of thread grooves extending at least partially about a circumference of the body as well as a means to permit the heart stabilizer, the instrument stabilizer, or another device to be releasably secured to the port. The distal portion of the tubular body is coupled to a swivel adapted to be moved between a first orientation in which the swivel extends in substantially a same direction as the body, and a second orientation at an angle relative to, and preferably substantially perpendicular to, the first orientation.

According to certain embodiments of the port device, a washer is positioned on the body between the swivel and the proximal portion of the body, and a locknut is threadably engaged in the thread grooves. When the tubular body is inserted between two ribs in the chest wall of the patient, the swivel is then opened into the second orientation and the washer is moved along the body to position the chest wall between the swivel and the washer. The locknut is then tightened about the body to clamp the washer against the chest wall and stably secure the tubular body within the chest wall.

According to other embodiments of the port device, a platform movable along the length of the port body includes adjustable legs and feet. The legs are adjusted such that the feet contact the chest wall and clamp the chest wall between the feet and the swivel. In addition, the legs may be adjusted to provide the body in a desired angle relative to the chest wall. According to preferred aspects of these embodiments of the port device, the platform may be ratcheted relative to the port body and the feet may be ratcheted relative to the platform to permit rapid adjustment of the port relative to the patient. In addition, preferably three legs are provided to aid in stability of the port on the body of the patient.

According to various aspects of the several embodiments of the port, the port may include a thread system adapted to permit quick locking of the locknut against the washer or the platform along the body, one or two swivels, and/or a ball joint permitting angular orientation of the port to permit the port to be directed toward a desired location such as the surgical site. In addition, the swivel or swivels may be spring biased to move from the first orientation to the second orientation, or an introducer device may be provided to mechanically move the swivel or swivels between the first and second orientations.

The heart stabilizer preferably includes a shaft and two jointed arms coupled to a distal end of the shaft. At the end of each arm is a rotatable foot adapted to be angled relative to the heart wall contour and apply pressure against the wall of the heart to effectively eliminate motion of the heart wall between the feet. The stabilizer is adapted to provide a stabilized area sufficiently large to allow an accurate anastomosis to be performed. According to preferred aspects of the invention, the stabilizer is particularly adapted to be collapsible (foldable) to be inserted through the port device and locked longitudinally relative thereto. The stabilizer is also preferably adapted to be manipulated into a desired configuration by operation of a proximal portion of the stabilizer extending outside the port, and then locked in such position. In addition, the stabilizer is adapted to automatically fold when being pulled back through the port.

According to various embodiments of the heart stabilizer, the feet of the stabilizer may be further adapted to facilitate immobilization of the heart wall between the feet. In addition to compressive forces, the feet may apply suction, chemical agents, electrical current, or thermal cooling to enhance the heart wall immobilization.

According to another aspect of the invention, the instrument stabilizer is adapted to minimize unwanted motion at the distal end of a surgical instrument extending through the instrument stabilizer by applying a biasing force to the tip of the instrument. The instrument stabilizer may be coupled to a port or more preferably may be coupled directly to a patient, e.g., with sutures. According to a currently preferred embodiment, the instrument stabilizer preferably includes a cannula (tubular member) through which an instrument can extend, and a preferably distal contact element, e.g., an O-ring or a tapered diameter of the cannula, adapted to be in a close fit about the instrument and which provides proximal and distal stabilization. The instrument stabilizer also includes a proximal housing that preferably includes a mechanism which applies a stabilizing force to the tubular member for movements transverse to the axis of the cannula. The mechanism which applies the force may be, by way of example, one or more of elastic bands, springs, struts, etc. In one embodiment, the stabilizing force is applied by the tissue of the patient and not by a mechanical mechanism within the housing. When the surgical instrument is extended through the cannula and contacts the contact element, movement of the cannula and consequently the surgical instrument is damped by the stabilization force on the cannula. The housing is preferably couplable to the body of a patient, e.g., via negative pressure, sutures, or an adhesive. Also, according to the currently preferred embodiment, the cannula may be locked in an angular orientation relative to a base. Furthermore, the cannula is optionally provided with a valve to permit the instrument stabilizer to be used for surgical procedures requiring insufflation of the body cavity in which the instrument stabilizer is inserted. According to other embodiments, a cannula is not required and the mechanism which applies a stabilization force to a medical instrument may be attached to a shaft of another instrument, e.g., the shaft of the heart stabilizer.

A stabilizer swivel may be used with an instrument stabilizer to angularly direct the cannula of the instrument stabilizer relative to the body of the patient. The stabilizer swivel includes upper and lower wedges rotatably coupled to each. Each wedge includes an opening through which the cannula may be extended. Relative rotational configurations of the wedges operate to orient the opening of the upper wedge relative to the lower wedge and the surface on which the lower wedge is seated.

The above-described components together define a surgical system for performing port off-pump beating heart coronary artery bypass surgery. According to a preferred method which utilizes the system, a port device is stably positioned, e.g. clamped, in the chest wall and directed as necessary for operation on the heart wall. A heart stabilizer is coupled to the port, and operated to apply a compressive force against the heart wall surrounding a location of the required bypass such that the location is substantially immobilized. An instrument stabilizer is inserted through a puncture hole in the chest cavity, and the distal tip of the cannula of the stabilizer is located adjacent to the surgical site. A first surgical instrument, e.g., a scalpel or needle holder, is passed through the cannula and operated to perform at least a portion of the procedure. If other surgical instruments are required, the first instrument may be removed and other instruments may be extended therethrough. Alternatively, an instrument stabilizer may be provided for each instrument. Once the bypass procedure is complete, the instruments and instrument stabilizers are removed from the locus of the surgery, and the heart stabilizer is also removed through its port. Then, the clamping forces on the port is loosened and the port is withdrawn from the chest wall. Finally, the incision and puncture holes in which the port and instrument stabilizer were located are closed. This method eliminates the need for many open heart procedures, as well as the need to stop the heart.

Additional objects and advantages of the invention will become apparent to those skilled in the art upon reference to the detailed description taken in conjunction with the provided figures.

BRIEF DESCRIPTION OF THE DRAWINGS

FIG. 7 is a front perspective view of an introducer according to the invention;

FIG. 8 is an exploded perspective view of the introducer of FIG. 7;

FIG. 35 is a lower perspective view of a first embodiment of an instrument stabilizer according to the invention;

FIG. 36 is a top perspective view of the first embodiment of the instrument stabilizer;

FIG. 49 is a side view of a stabilizer swivel according to the invention and in a normal direction;

FIG. 50 is an exploded view of the stabilizer swivel according to the invention;

FIG. 51 is a side view of the stabilizer swivel in a first angular orientation;

FIG. 52 is a side view of the stabilizer swivel in a second angular orientation;

FIG. 71 is a bottom perspective view of the seventh embodiment of an instrument stabilizer, shown with an alternate vacuum base;

FIG. 72 is a top perspective view of an eighth embodiment of an instrument stabilizer according to the invention;

FIG. 75 is a side elevation of the eighth embodiment of an instrument stabilizer according to the invention, shown in an angled configuration;

FIG. 76 is a section view across line 76—76 in FIG. 75;

FIG. 81 is an enlarged distal end view of the distal end of the heart stabilizer of the second embodiment of the invention;

FIG. 83 is a longitudinal top section view of the heart stabilizer of the second embodiment of the invention, shown in a closed configuration;

FIG. 86 is a perspective view of the second embodiment of a heart stabilizer shown in an open configuration according to the invention;

FIG. 87 is a perspective view of the second embodiment of a heart stabilizer shown in a locked configuration according to the invention;

FIG. 89 is an exploded perspective view of a shaft lock according to the second embodiment of the invention.

DETAILED DESCRIPTION OF THE PREFERRED EMBODIMENTS

According to the invention, a system is provided for performing port off-pump beating heart coronary artery bypass surgery. The system includes a port device and a heart stabilizer.

Figure 1:
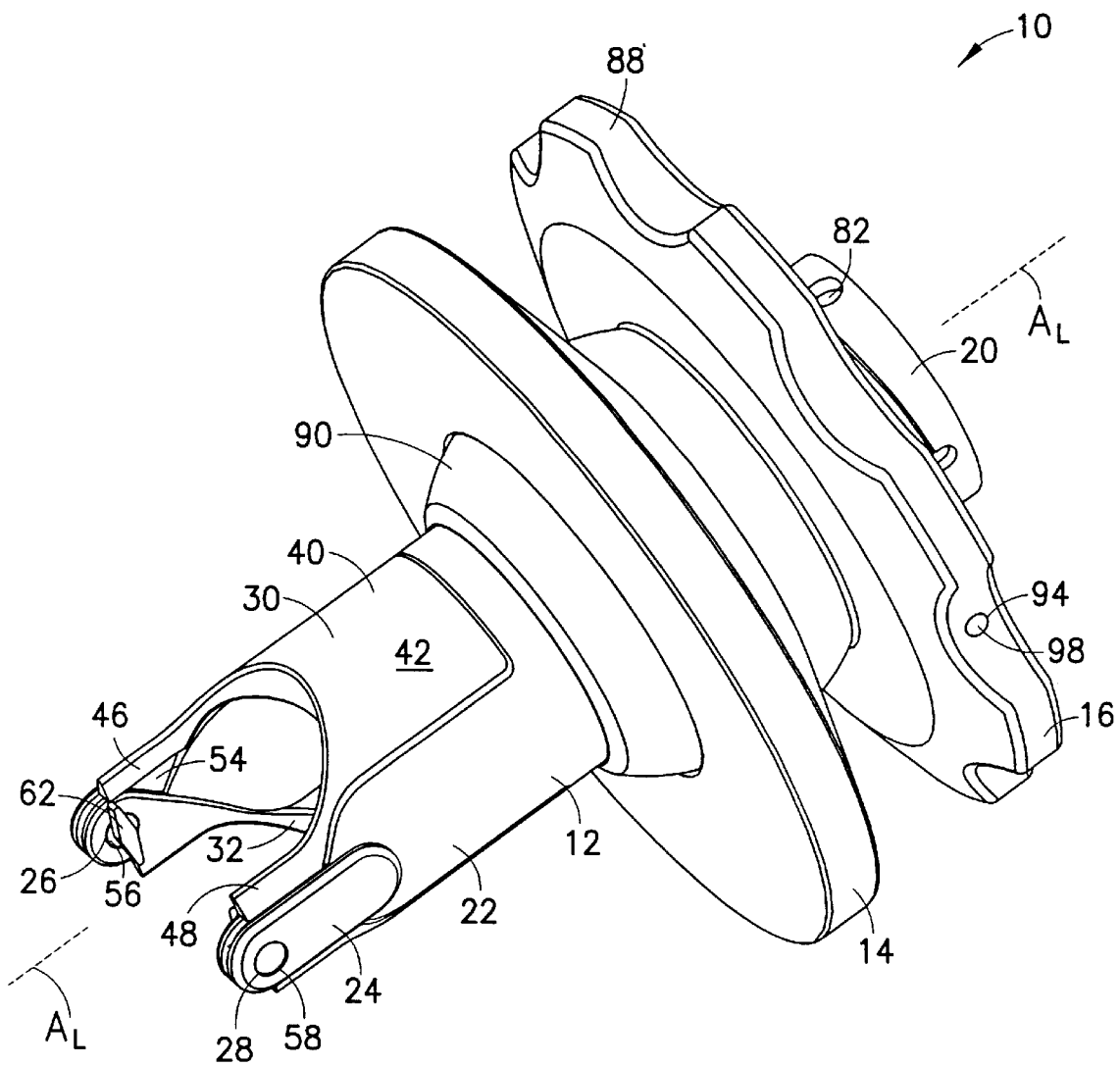
FIG. 1 is a bottom perspective view of a first embodiment of a port device according to the invention, shown with the swivels in a closed configuration.

Turning now to FIG. 1, a first embodiment of the port device 10 includes a tubular body 12, a washer 14 slidably mounted on the tubular body and a locknut 16 threadably coupled to the body 12 proximal of the washer 14. The tubular body 12 includes a proximal portion 20 and a distal portion 22. The distal portion 22 includes a clevis 24 defining two coaxial pivot bores 26, 28, and a pair of clamping swivels 30, 32 are rotatably coupled to the clevis 24 at the pivot bores 26, 28.

Figure 2:
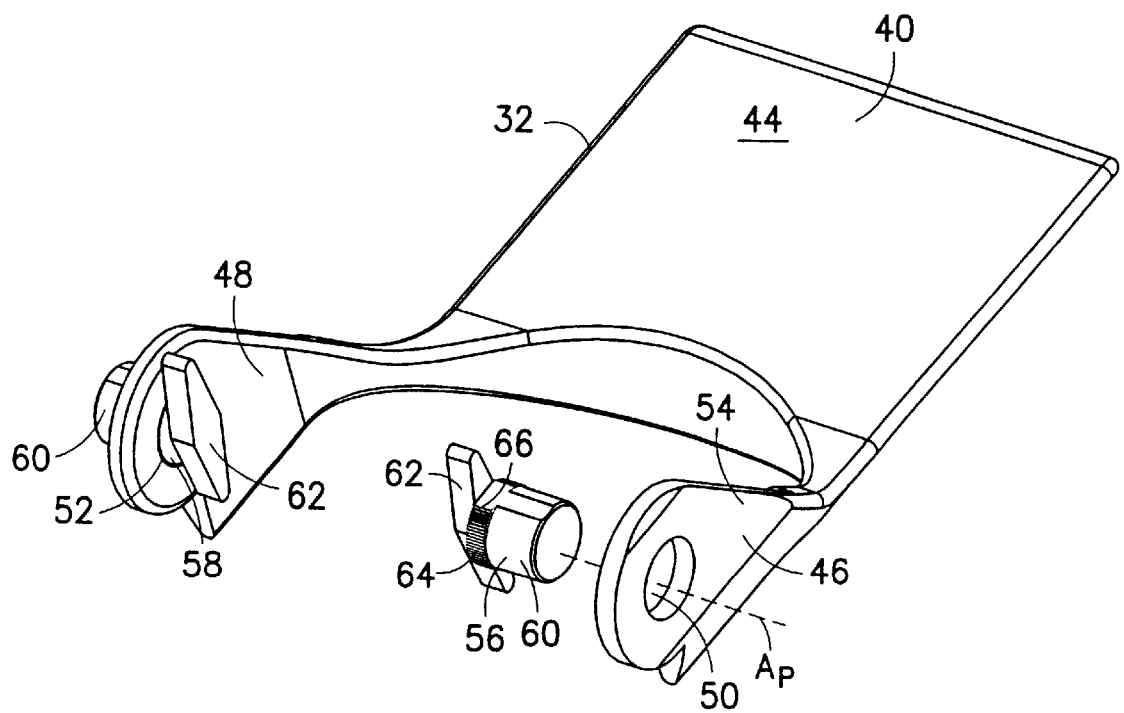
FIG. 2 is a partially disassembled top perspective view of a swivel and pivot axles according to the first embodiment of a port device according to the invention.
Figure 3:
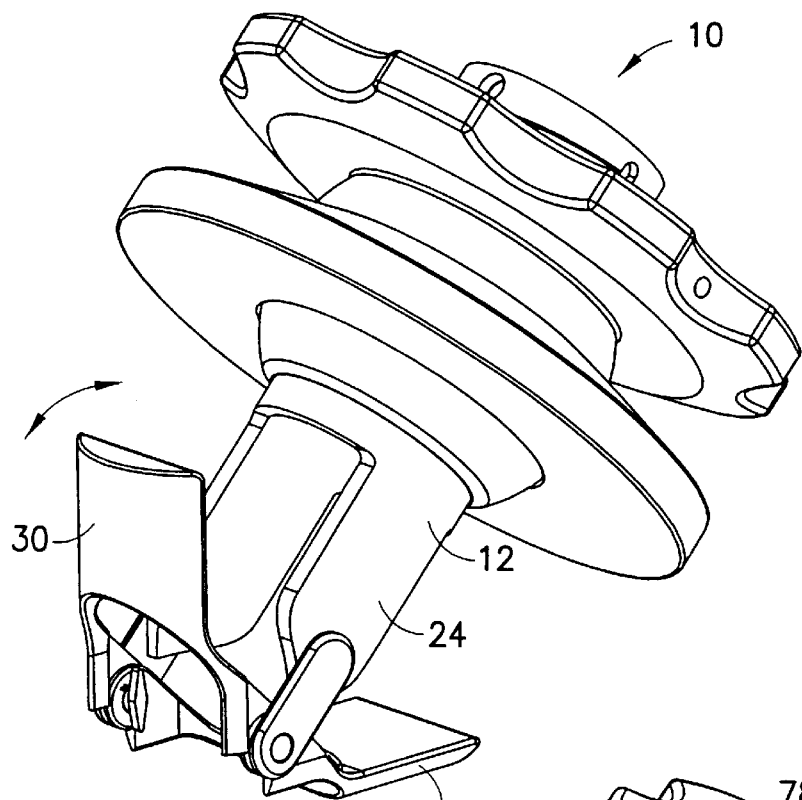
FIG. 3 is a bottom perspective view of the first embodiment of the port device according to the invention, shown with the swivels in a partly open configuration.
Figure 4:
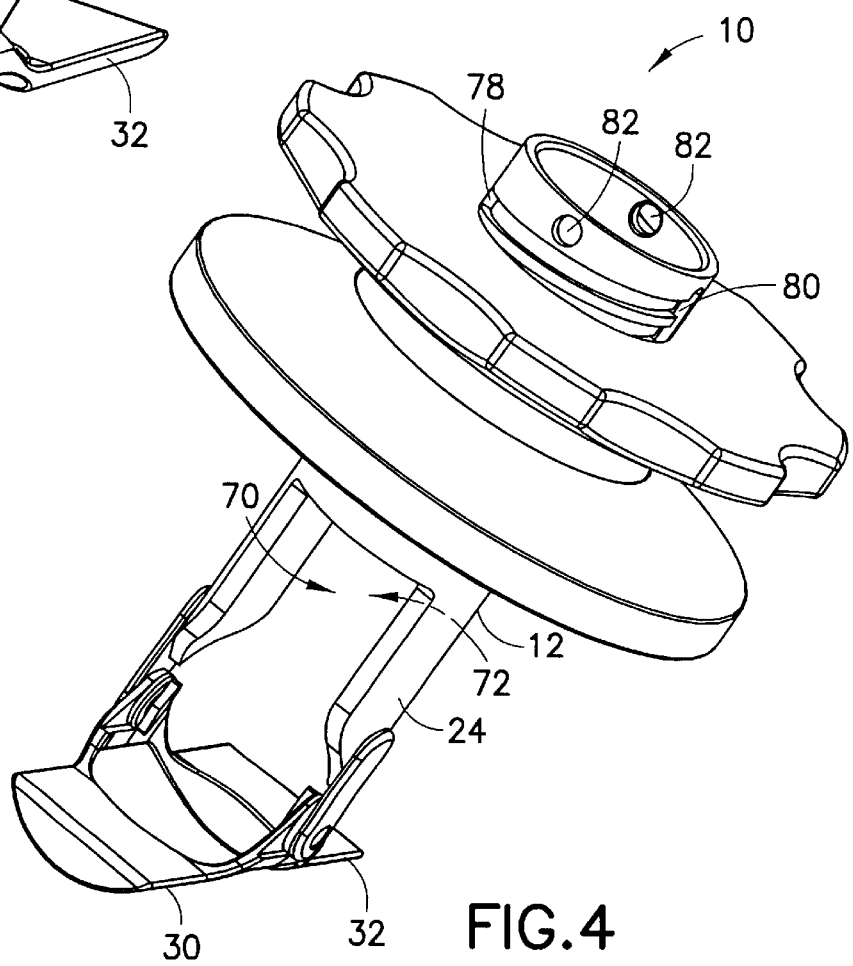
FIG. 4 is a top perspective view of the first embodiment of the port device according to the invention, shown with the swivels in an open configuration.

Referring to FIGS. 1 and 2 and with reference to swivel 32, each swivel includes a wing portion 40 with a preferably curved outer surface 42 and a preferably substantially planar inner contact surface 44, and two arms 46, 48 each including an axle bore 50, 52. One arm 46 of each swivel includes an inner recess 54 adapted to permit interleaving of the swivels about the clevis 24. Each arm 46, 48 of the swivel is coupled to the tubular body 12 with an axle member 56, 58 which extends through a respective axle bore 50, 52 and pivot bore 26, 28, and defines a pivot axis $A_P$. With reference to axle member 56, each axle member includes a relatively cylindrical first portion 60, an elongate trapezoidal-shaped lever 62, and an interference portion 64 between the first portion and lever portion. The interference portion 64 is slightly larger in diameter than the first portion 62 and includes knurls 66 or other gripping structure. The interference portion 64 of axle member 56 engages arm 46 about a respective axle bore, and the first portion 60 extends into the clevis bore 26, in which it is freely rotatable, while the interference portion 64 of axle member 58 engages arm 48 about a respective axle bore. As such, each axle member 56, 58 is fixedly attached to only one of the swivels and the swivel pivots about it. Then, as each swivels rotates about the clevis, a respective lever is also rotated and, similarly, rotation of the individual levers results in independent rotation of the swivels. The swivels 30, 32 are rotatable from a closed orientation (FIG. 1) in which the swivels extend substantially parallel to the body 12 through intermediate orientations (e.g., FIG. 3), and into a open orientation in which the swivels 30, 32 extend preferably perpendicular to the first orientation (FIG. 4). When in the first orientation, the swivels 30, 32 preferably complete the openings 72, 74 (FIG. 4) defined by the clevis 24, and the curvature of the outer surfaces 42 of the swivels provide the outer surface of the distal portion 22 with a substantially smooth surface. In addition, in the first orientation, the levers 62 are preferably oriented transverse the longitudinal axis $A_L$ of the body 12.

Figure 5:
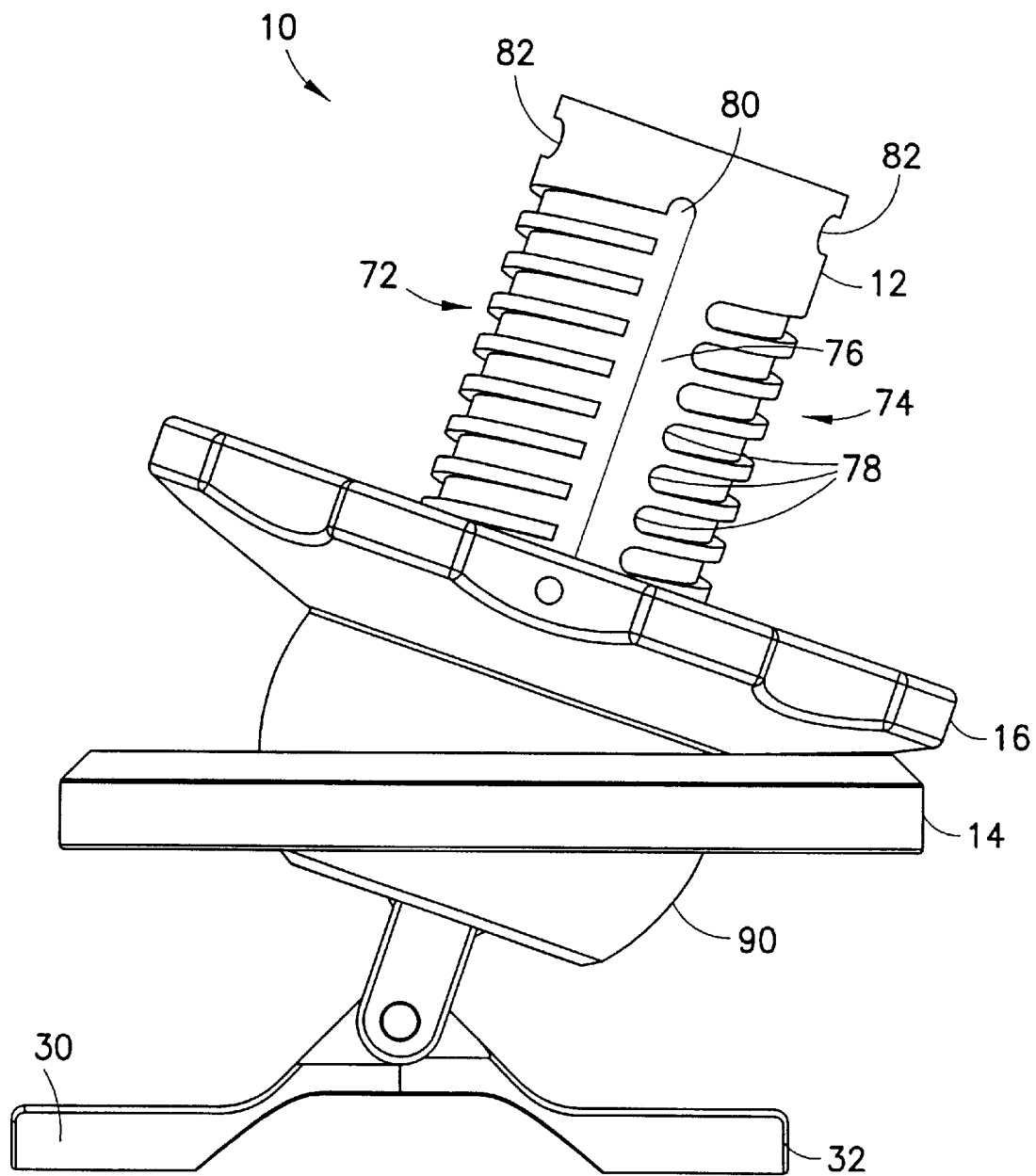
FIG. 5 is a side elevation view of the first embodiment of the port device according to the invention, shown with the swivels in an open configuration, and the port body angled relative to the washer.

Referring to FIG. 5, the proximal portion 20 of the tubular body 12 includes first and second sets of interrupted helical threads (grooves) 72, 74 extending along diametrically opposite sides of the body. The interruption 76 in the threads creates stops 78 after substantially 180° of rotation. A longitudinal groove 80 connects each set of threads 72, 74 together. The locknut 16, as described hereinafter, travels in the longitudinal grooves 80 and the threads 72, 74.

Referring now to FIGS. 1, 4 and 5, the proximal end 20 of the body 12 includes a coupling structure, e.g., the holes 82 of a ball latch, for removably coupling thereto the heart stabilizer the hereinafter described port introducer, or other device, as described in detail below.

The washer 14 is preferably disc-shaped and has a central opening 84 permitting the washer to fit about the tubular body 12 and provides an external clamping structure which operates in conjunction with the swivels 30, 32 to clamp human tissue therebetween, as described further below.

Figure 6:
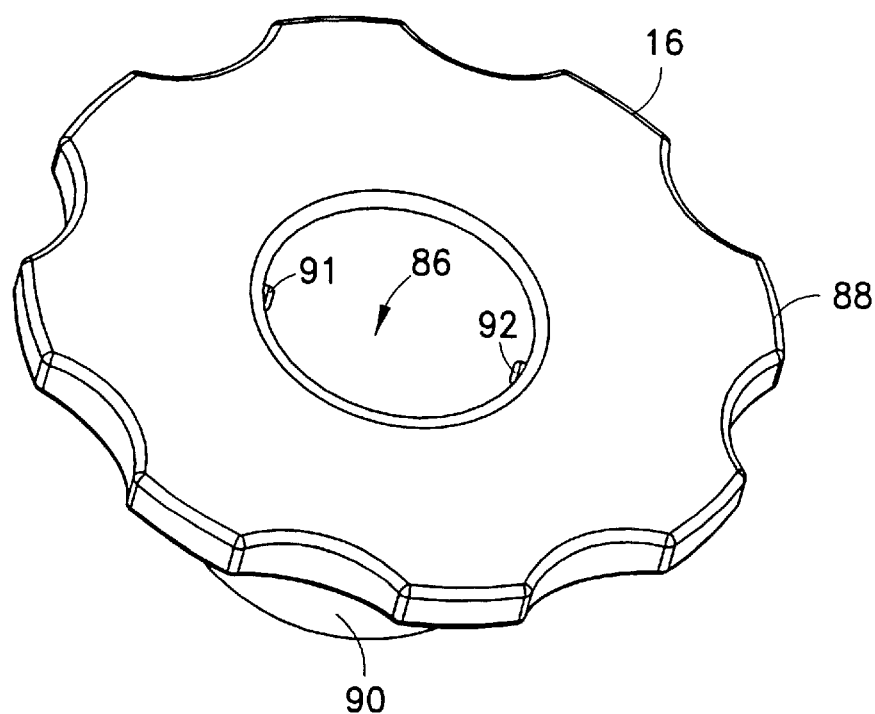
FIG. 6 is a top perspective view of a locking nut according to a first embodiment of a port device according to the invention.

Referring to FIGS. 1 and 6, the locknut 16 includes a central opening 86, a handle portion 88, and a ball portion 90. Two nubs 91, 92 radially extend into the central opening and are sized to ride within the threads 72, 72, 74 and longitudinal grooves 80 on the proximal portion of the tubular body 12 (FIG. 5). As such, when each nub 91, 92 is positioned within a respective longitudinal groove 80, the locknut 16 may be moved quickly over the port body 12 and then rotated to thread the nubs 91, 92 into the threads 72, 74 to secure the locknut 16 at a desired location over the body 12. One preferred manner of forming the nubs 91, 92 includes providing two diametrically opposite radial holes 94 in the handle portion 86 and inserting peg 98 into each radial hole such that the pegs extend into the central opening 86 to form the nubs. The ball portion 90 is a truncated sphere in shape and defines a diameter slightly larger than the diameter of the central opening 84 of the washer 14. Referring to FIGS. 1 and 5, the washer 14 is thereby adapted to articulate on the ball portion 90 of the locknut 16.

Figure 9:
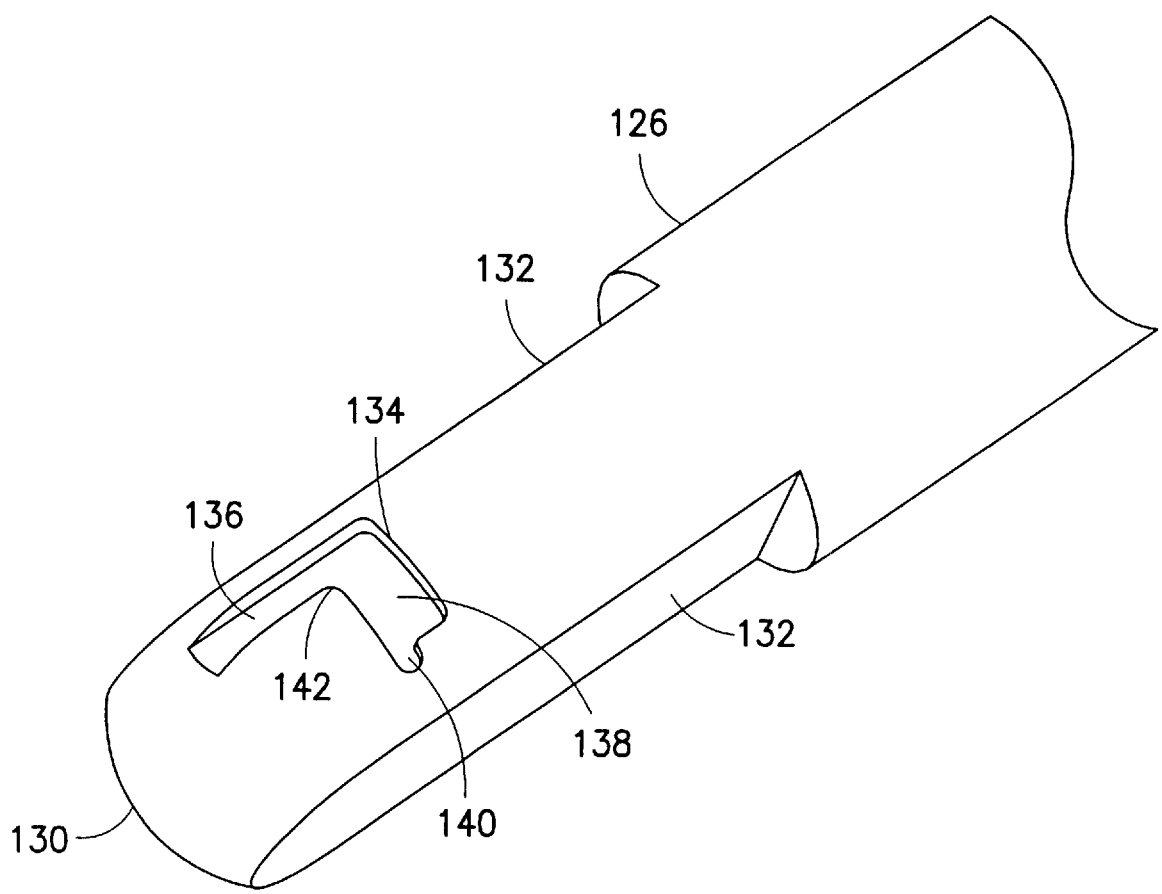
FIG. 9 is an enlarged perspective view of the distal end of the introducer of FIG. 7.

Turning now to FIGS. 7 and 8, an introducer 100 adapted to introduce the port device into an incision in the chest wall and also to effect movement of the swivels between closed and open configurations is shown. The introducer 100 includes a central tubular handle 102, a proximal cap 104, and a mandrel 106 extending through the handle 102 and coupled to the cap 104. The handle 102 includes a proximal stop notch 107, and distal smaller diameter portion 108 including two diametrically-opposed hemispherical latch elements 110 for engagement within holes 82 of the port body 12, and which together form a ball latch. The latch elements 110 are provided on fingers 112 of the handle 102, which under radial force are moved radially inward. The cap 104 includes a tubular portion 114 provided with a radial hole 116, and a knob 118 which is relatively larger in diameter than the tubular portion. The tubular portion 114 of the cap 104 extends into the handle and the knob 118 seats on the proximal end 119 of the handle. The mandrel 106 includes a cylindrical shaft 120 provided with a radial bore 122 and two diametrically-opposed distal planar portions 124, and a distal actuator 126. The shaft 120 extends through the handle 102 and into the cap 104. A crosspin 128 is positioned through the radial hole 116 and into radial bore 122 securing the shaft 120 of the mandrel 106 and the cap 104 together. In addition, the crosspin 128 extends into the stop notch 107 limiting rotation of the knob (and mandrel) relative to the handle 102. The planar portions 124 provide space to permit radial movement of the latch elements 110 when the fingers 112 of the handle 102 are compressed. Referring to FIGS. 7 through 9, the actuator 126 of the mandrel 106 includes a preferably blunt end 130 and a pair of diametrically-opposed substantially planar sides 132 about the end 130. A pair of diametrically-opposed actuation grooves 134 are provided between the planar sides 132. The actuation grooves 134 are generally L-shaped and include a longitudinal portion 136 which terminates at the blunt end 130, and a transverse portion 138. The transverse portion 138 includes a notch 140.

Figure 10:
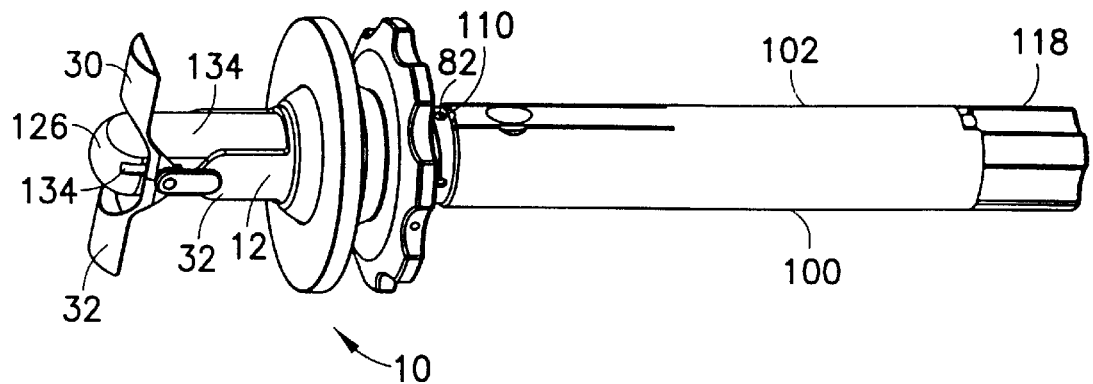
FIG. 10 is a side perspective view of introducer coupled to the port device according to the invention, with the swivels shown in an open configuration.
Figure 11:
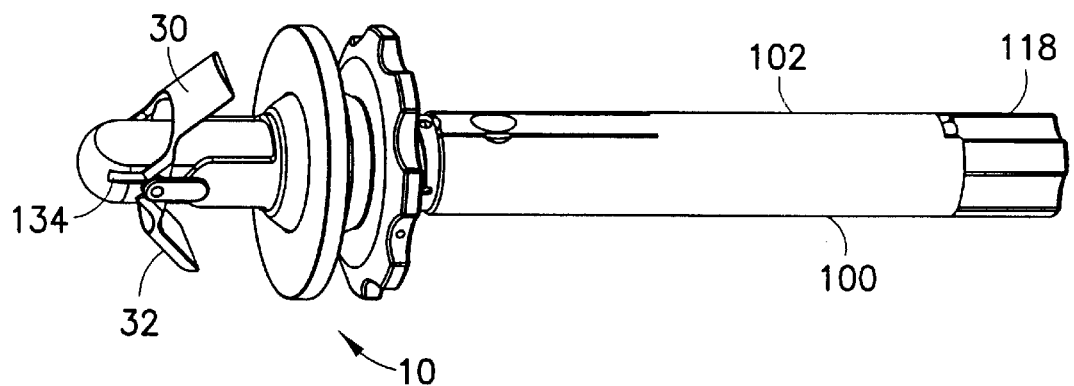
FIG. 11 is a view similar to FIG. 10 with the swivels shown in a partly closed configuration.
Figure 12:
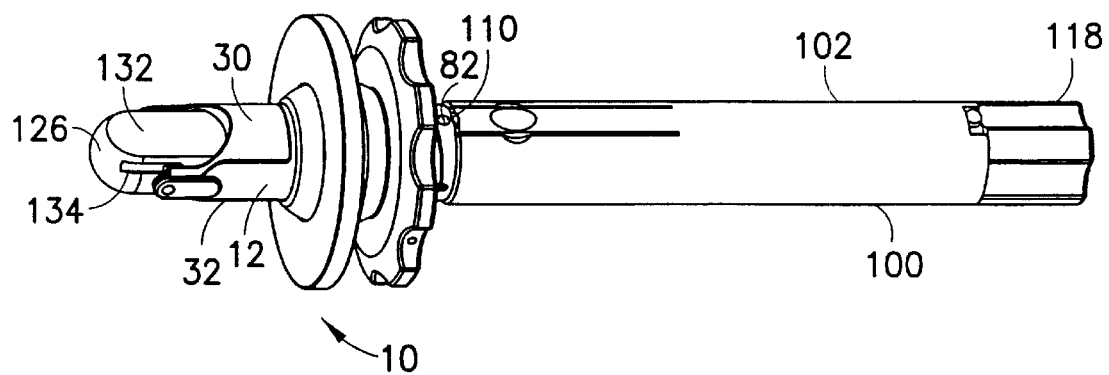
FIG. 12 is a view similar to FIG. 10 with the swivels shown in a closed configuration.

Referring now to FIG. 10, the introducer 100 is coupled to the port device 10 by opening the swivels 30, 32 of the port device and inserting the actuator 126 of the introducer until the ball latch engages; i.e., the proximal end of the port device rides over the latch elements 110 until the latch elements catch in the holes 82 in the port body 12. With the swivels 30, 32 in the open configuration, the levers 62 (FIG. 2) are also aligned within respective longitudinal portions 136 of the actuation grooves 134 and reside therein. More particularly, the pivot axis $A_P$ of the levers 62 are located just proximal of the inner corners 142 of the grooves (FIGS. 2. and 9). Referring to FIGS. 2, 9, 11 and 12, while keeping the handle 102 fixed, the knob 118 is rotated in a clockwise direction (causing movement of the grooves 134 relative to the levers 62. The corners 142 contact the levers 62 and rotate the levers into the transverse portions of each of the grooves, thereby effecting closing of the swivels about the port body 12. One end of each lever engages a notch 140 in its respective groove 134 to "lock" the levers (and swivels) in the closed position until the knob is rotated in an opposite direction. The amount of the rotation of the knob 118 relative to the handle 102 required to effectuate the closing is relatively limited, e.g., approximately twenty-four degrees with groove 134, and contact of the crosspin 128 against the top notch 107 limits the movement.

The introducer may be provided with other shaped grooves, the rotation of which effects movement of the levers and swivels. For example, referring to FIG. 31, the J-groove 134a on the introducer 100a operates to close (or open) the swivels by clockwise rotation of approximately 45°.

The planar sides 132 of the actuator 126 are so shaped such that the swivels 30, 32 may rest thereagainst when the swivels are in the closed configuration (FIG. 12) and thereby permit the outer surface of the swivels to effectively complete the circumference of the tubular body of the port device.

Once the swivels are locked in a closed configuration about the introducer 100, the introducer may be manipulated to introduce the port device 10 into an incision in a chest wall, preferably between two ribs, or an incision in another area of human tissue. To secure the port within the incision, the knob 118 is rotated in a counter-clockwise direction, releasing the ends of the levers from the notch 140 and causing the levers to ride against their respective walls of longitudinal portions 136 and rotate about their pivot axis $A_P$. This results in aligning the levers 62 within the longitudinal portions 136 of the grooves 134 and moving the swivels into the open configuration (FIG. 10). In the open configuration, it is preferable that the swivels each be located under a respective rib. The port body 12 is pulled back to contact the ribs and then the washer 14 is moved against the outer surface of the tissue surrounding the incision. The nut 16 is advanced through the longitudinal grooves 80 to contact and press against the washer and then threadably rotated within the threads 72, 74 to lock against the washer. The swivels and washer thereby provide a clamping action about the ribs and tissue and stably secure the tubular body 12 of the port device within the chest wall.

The introducer 100 is then released from the port body 12 by depressing the fingers 112 of the handle 102. Finally, the introducer is withdrawn leaving an open port through which a surgical instrument other device may be introduced, and to which a device may be securely coupled. It will be appreciated that due to the articulating relationship of the ball portion 90 of the lock nut 16 and the washer 14, the tubular port 12 may be articulated relative to the washer, and the chest wall.

The port device may be removed from the body by reinserting the introducer in the port device such that the levers align with and enter the longitudinal grooves. The introducer is preferably coupled to the tubular body. The locknut is released, and the port device is moved slightly into the chest cavity to provide space for the swivels to fold. Then the knob of the introducer is rotated relative to the handle to cause the actuator to rotate relative to the swivels, and cause the swivels to fold against the tubular body into the closed configuration. The introducer and port device are then together withdrawn from the chest wall of the patient.

The introducer may also be configured as separate tubular handle and mandrel elements which may be used separate from each other. In such an embodiment of the introducer, the handle may be coupled to the port body and manipulated to introduce the port body between a hole in the ribs. The mandrel can then be inserted through the handle, and operated to open the swivels. The mandrel is then removed, followed by disengagement of handle from the port body. Such an embodiment of the introducer is shown below with respect to the introducer 2000 in FIGS. 59 and 60.

Figure 13:
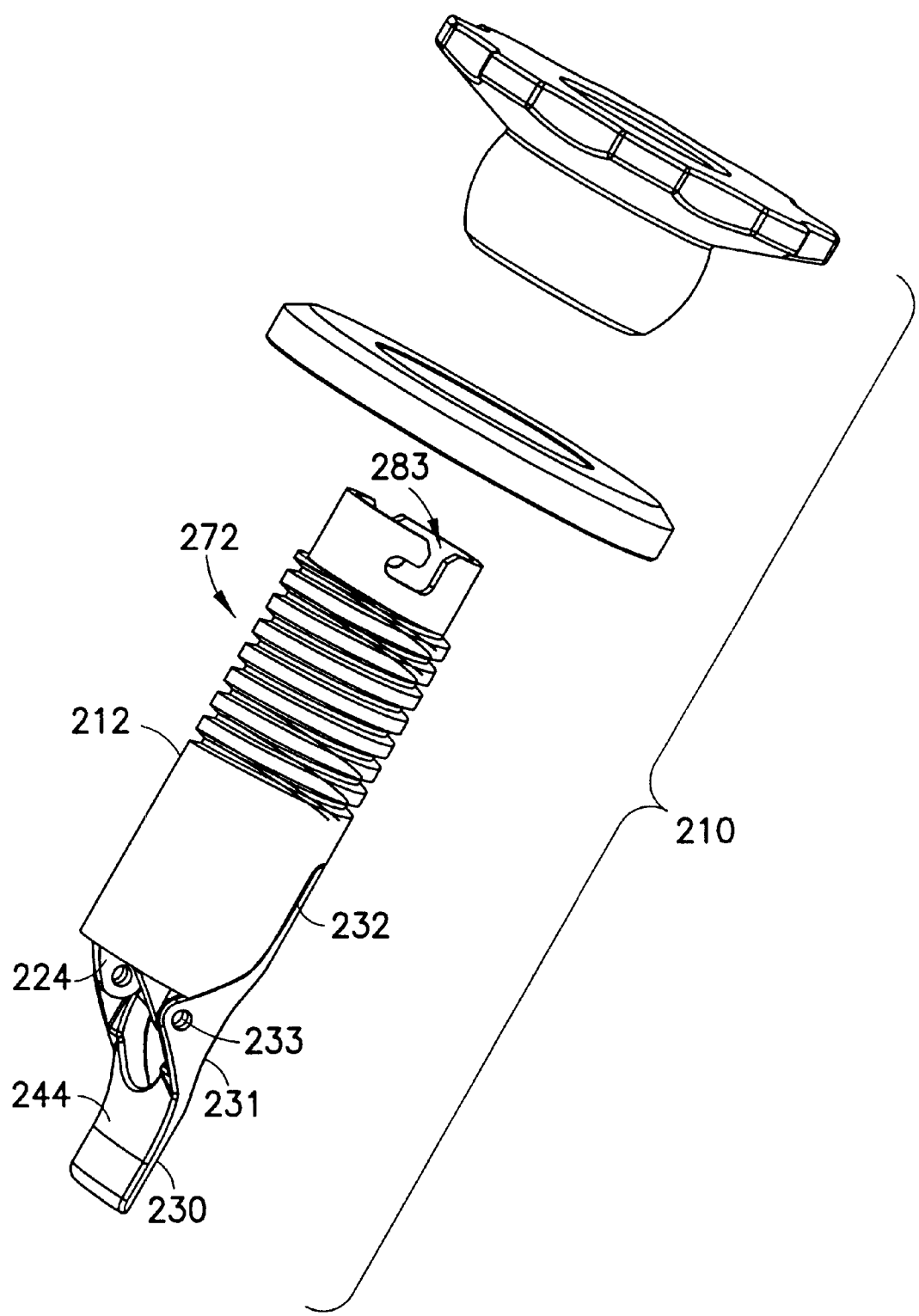
FIG. 13 is an exploded side perspective view of a second embodiment of a port device according to the invention, with the swivel shown in a closed configuration.
Figure 14:
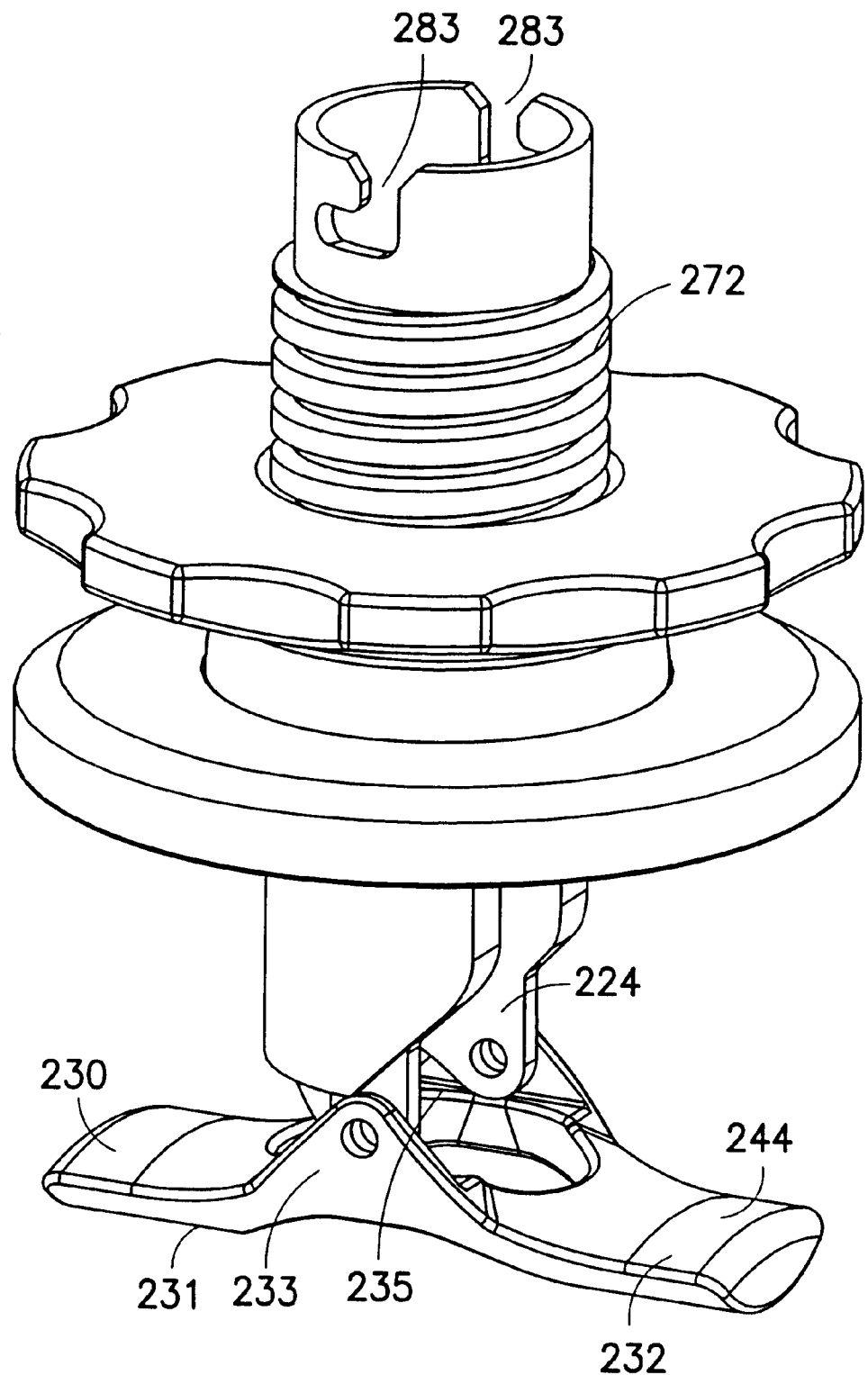
FIG. 14 is a top perspective view of the second embodiment of the port device, with the swivel shown in an open configuration.
Figure 15:
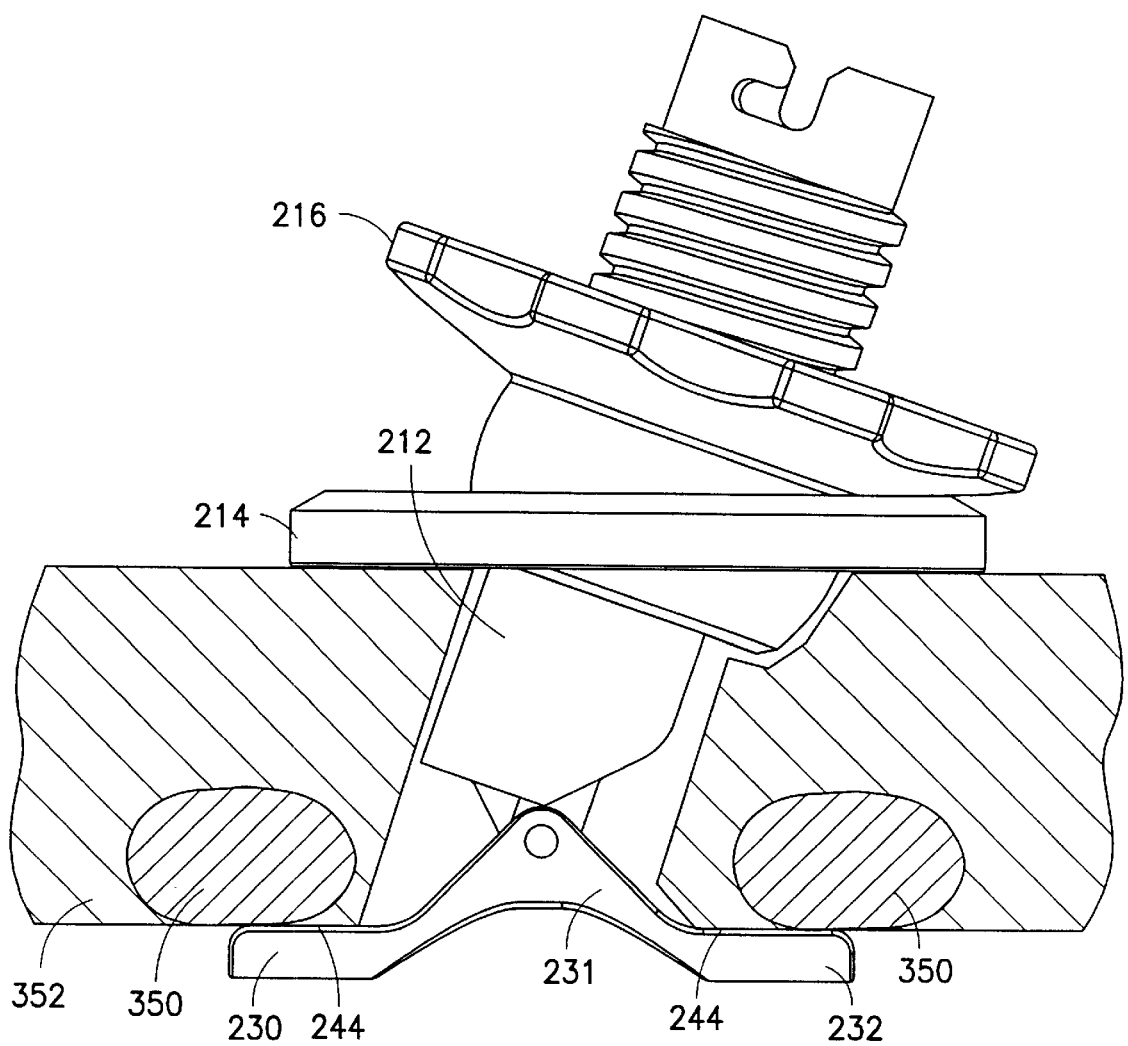
FIG. 15 is a side perspective of a second embodiment of the port device shown inserted in body tissue and between ribs of a patient.

Turning now to FIGS. 13 and 14, a second embodiment of a port device 210 according to the invention substantially similar to the first embodiment (with like parts having reference numerals incremented by 200) is shown. The tubular body 212 of the port device 210 includes a double helix thread 273 without interruptions. The proximal end of the port device includes a female bayonet coupling 283. The distal end of the tubular body includes a single swivel 231 including two arms 230, 232 and rotatably coupled at a central portion 233 to a clevis 224 formed at the distal end of the body. The inner contact surfaces 244 of the swivel are preferably provided with a convex contour to facilitate placement of the swivels against the ribs even when the tubular body is articulated through various angles relative to the washer. The swivel 231 is preferably biased with a spring 235 to move into an open configuration substantially perpendicular to the tubular body. As such, during insertion, a mandrel (not shown) is preferably positioned within the tubular body, and may be coupled to the female bayonet coupling, to maintain the swivel in a closed configuration substantially parallel to the tubular body. Then, when the proximal end of the swivel 231 is past the ribs (see FIG. 15), the mandrel is removed from the tubular body, and the spring 235 automatically rotates the swivel 231 into the open configuration with the swivel being captured by the ribs 350. The washer 214 and locknut 216, which are preferably the same as described in the first embodiment, are then tightened against the tissue 352 (as shown in FIG. 15), clamping the ribs 350 and tissue 352 between the washer and swivel.

The swivel 231 may be returned to the closed configuration for removal from the patient body by loosening the locknut and washer, pushing the swivel distally into the chest cavity, and inserting the mandrel back through the tubular body and causing contact against an arm of the swivel to force the swivel to rotate back into the closed configuration.

Figure 32:
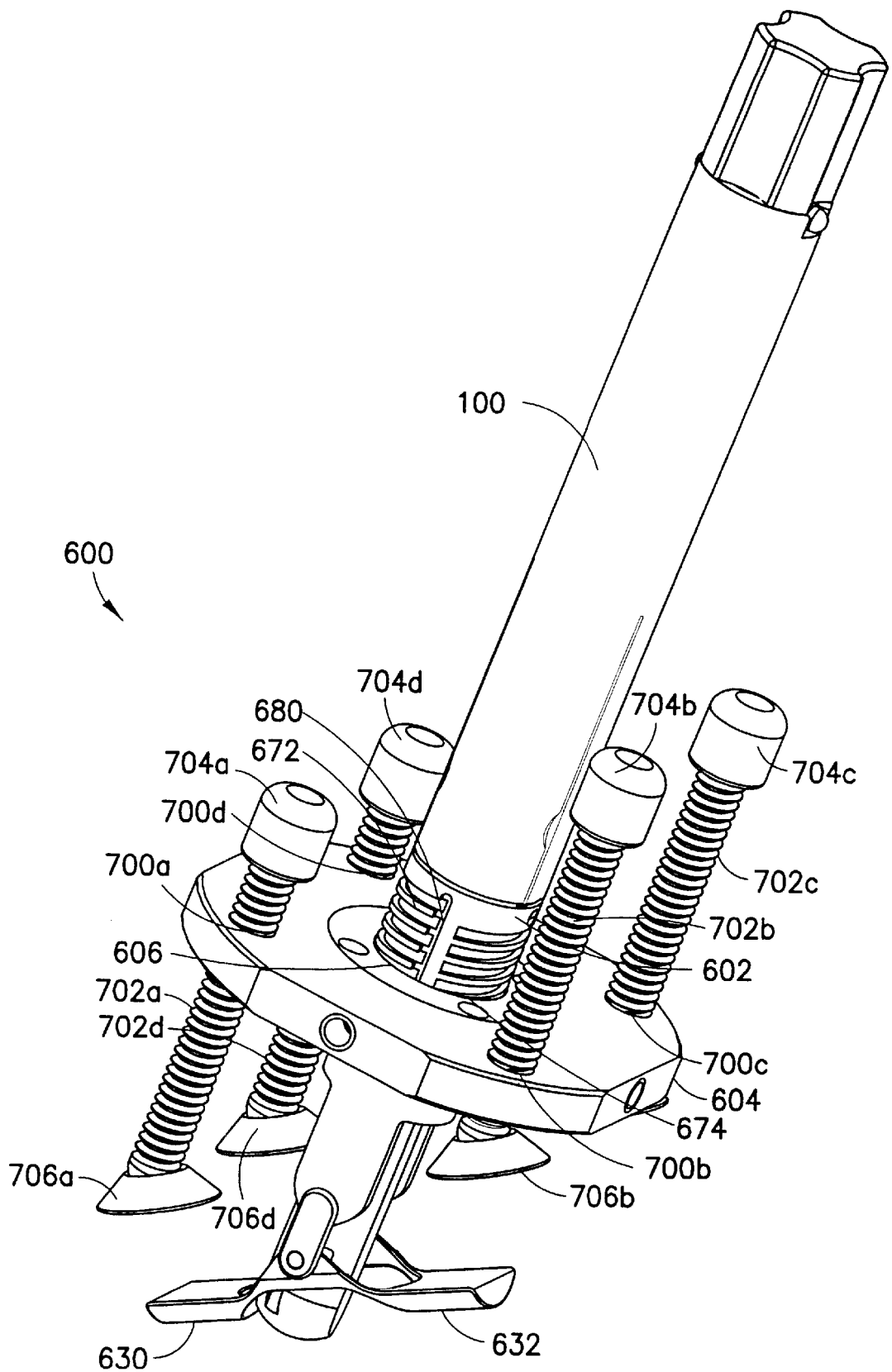
FIG. 32 is a perspective view of a third embodiment of a port device according to the invention.

Turning now to FIG. 32, a third embodiment of a port device 600 according to the invention is shown. The port device includes a tubular body 602 and an adjustable platform 604. The tubular body 602 includes swivels 630, 632 at a distal end thereof, and threads 672, 674 and longitudinal grooves 680 along the body, preferably the same as those described with respect the first embodiment. The platform 604 includes a central opening 606 and nubs which extend into the opening (the nubs are not shown, but are substantially similar to nubs 91, 92 in the first embodiment). The nubs permit the platform to travel in the longitudinal grooves 680 and threads 672, 674 to move and threadably lock the platform relative to the body 602. The platform 604 also includes a plurality of, e.g., four, threaded bores 700a–d preferably equally spaced about the central opening 606. Bolts 702a–d are thread partially through the bores 700a–d, and each is provided with a proximal handle 704a–d by which the bolt may be manually rotated, and a distal foot 706a–d pivotable about the end distal end of the bolt.

An introducer 100, shown coupled to the port device 600, is preferably utilized to insert and deploy the swivels 630, 632 of the port device 600 into the chest wall, and is then disengaged and removed from the port. The platform 604 is then angularly adjusted relative to the chest wall by rotating the bolts. That is, if it is desired to have the platform 604 be oriented substantially planar with the chest wall, each bolt 702a–d, by rotation of its respective handle 704a–d, is tightened by substantially the same amount to cause the chest wall to be evenly clamped between the swivels 630, 632 and the feet 706a–d. However, if it is desired to cause the platform, and port body 602 therein, be at an angle relative to the chest wall (to provide better access to the surgical site), the bolts 706a–d may be thread into the bores 700a–d by different amounts to cause the platform 604 to assume a desired angle relative to the chest wall.

Figure 33:
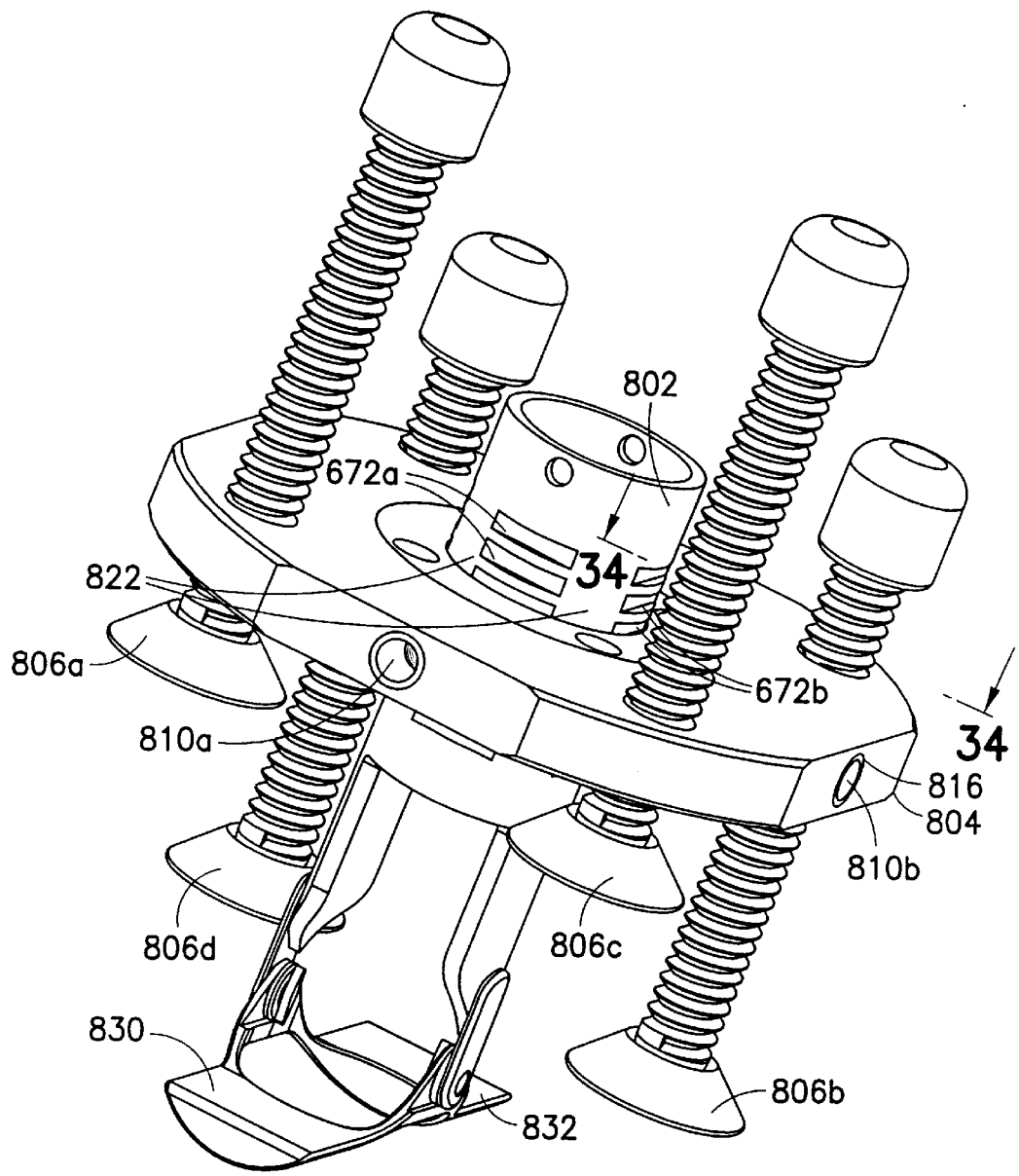
FIG. 33 is a perspective view of a fourth embodiment of a port device according to the invention.
Figure 34:
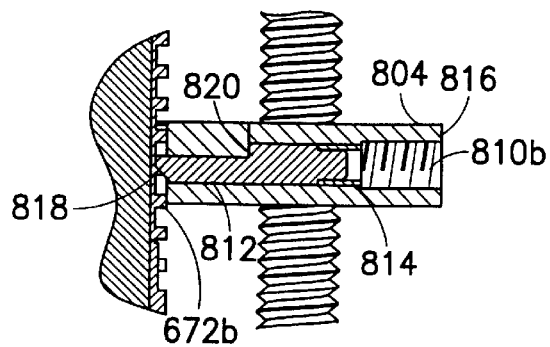
FIG. 34 is a partial section view across line 34—34 in FIG. 33 of the tubular body of the fourth embodiment of the port device of the invention.

Referring now to FIGS. 33 and 34, a fourth embodiment of a port device 800 according to the invention, substantially similar to the third embodiment 600, is shown. The tubular body 802 of the port device is provided with four sets of grooves 672a, 672b (672c and 672d not shown but located diametrically opposite 672a and 672b, respectively), rather than the threads 672, 674 of body 602 (FIG. 32). Each set of grooves 672a–d extends parallel to a respective tangent on the surface of the body and offset by ninety degrees about the body. The platform 804 includes four radial channels 810a, 810b (810c and 810d not shown) located ninety degrees apart. A ratchet pin 812 is provided in each of the channels 810a–d. A spring 814 is positioned within each channel 810a–d to bias each ratchet pin 812 toward a respective set of grooves 672a–d, and a locking collar 816 maintains the spring within the channel. The ratchet pin 812 is shaped to include a beveled edge 818 facilitating radial outward movement of the ratchet pin against the bias of the spring when the platform is moved distally over the grooves of the tubular body. In addition, the ratchet pin includes a stop 820 to limit inward radial movement. This configuration permits the platform to be readily and rapidly moved distally along the tubular body to a desired location with the ratchet pins locking within the grooves to prevent proximal movement of the platform, and thereby clamping the chest wall between the swivels 830, 832 and the feet 806a–d coupled to the platform. The feet may then be adjusted to orient the platform at an angle relative to the chest wall.

When it is desired to release the platform from about the tubular body, the feet are loosened from against the chest, and the platform is rotated approximately forty-five degrees such that the ratchet pins lie along smooth portions 822 of the tubular body. The platform may then be moved proximally relative to the tubular body without substantial resistance.

Figure 54:
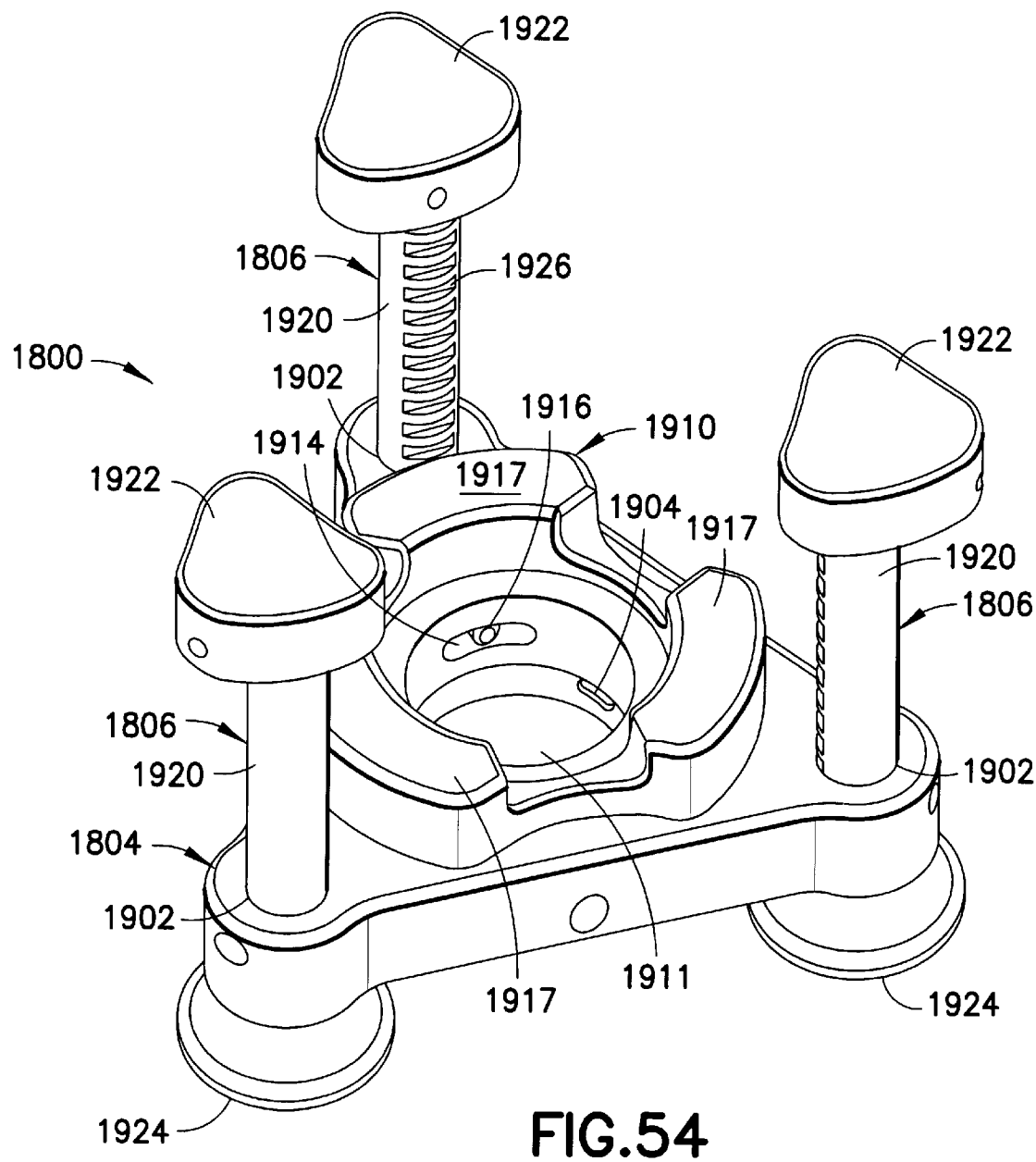
FIG. 54 is a top perspective view of a fifth embodiment of a port device according to the invention.
Figure 55:
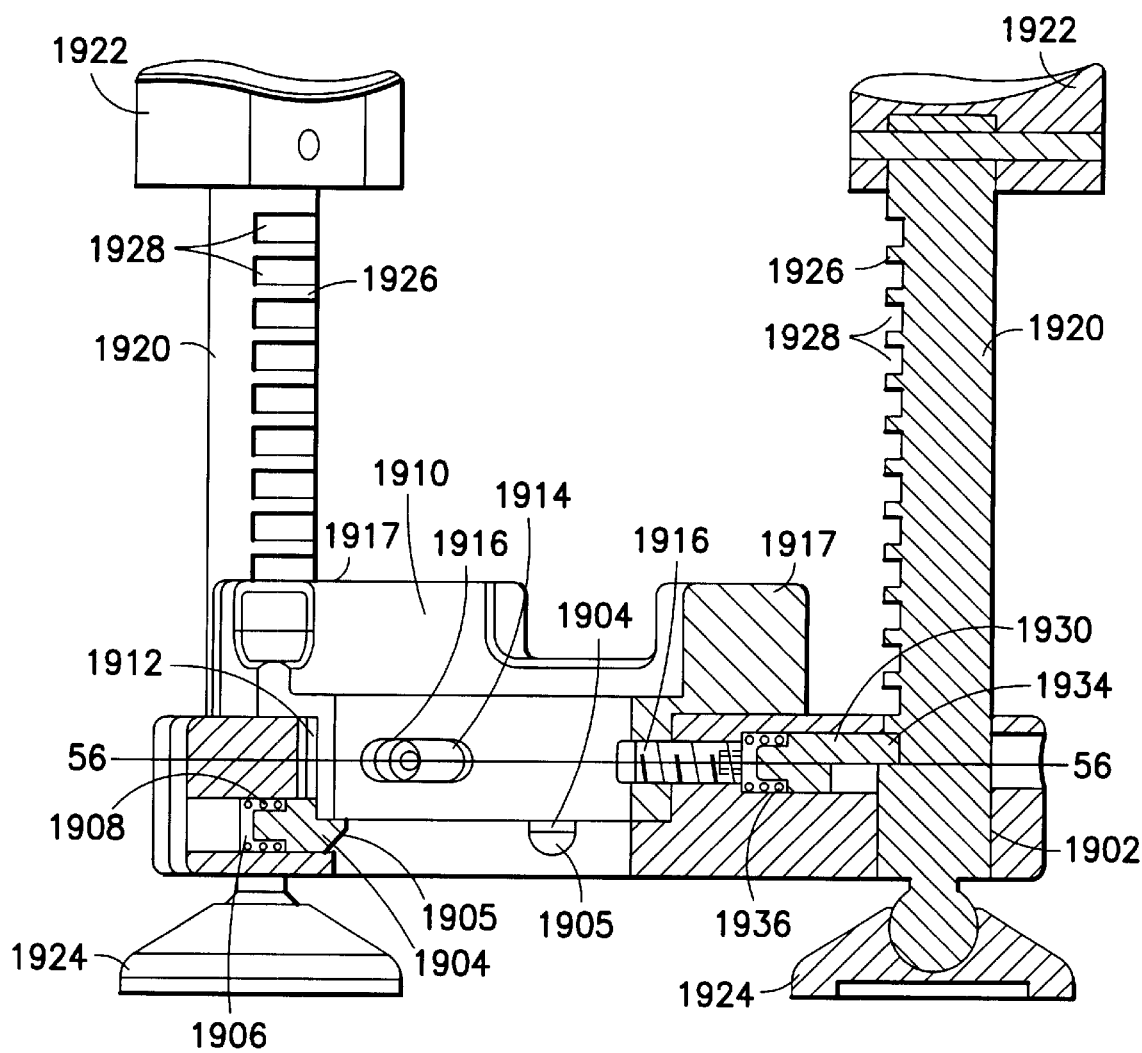
FIG. 55 is a longitudinal section view of the fifth embodiment of the port device, shown without the port tube.
Figure 56:
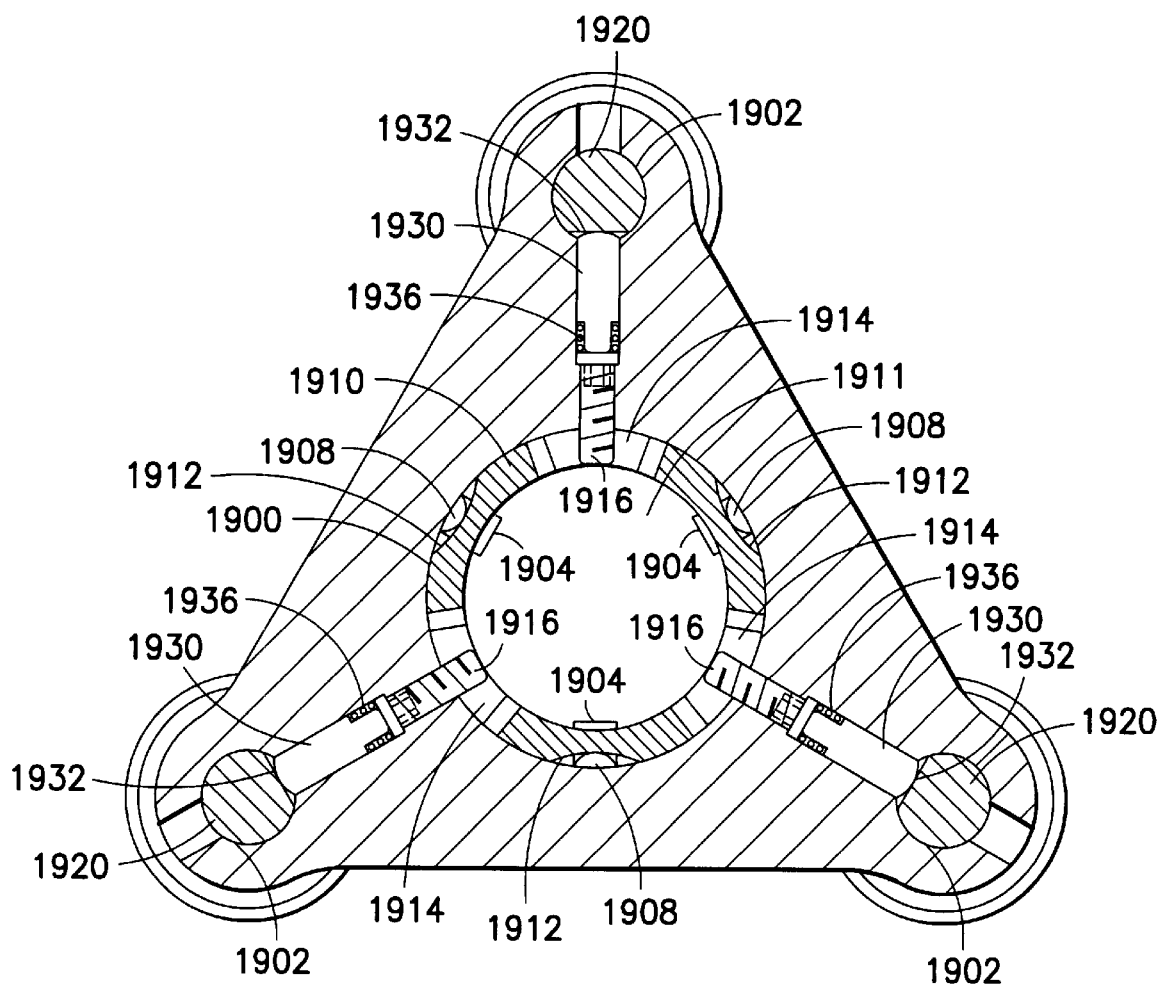
FIG. 56 is a transverse section across line 56—56 in FIG. 55 of the fifth embodiment of the port device, shown without the port tube.
Figure 57:
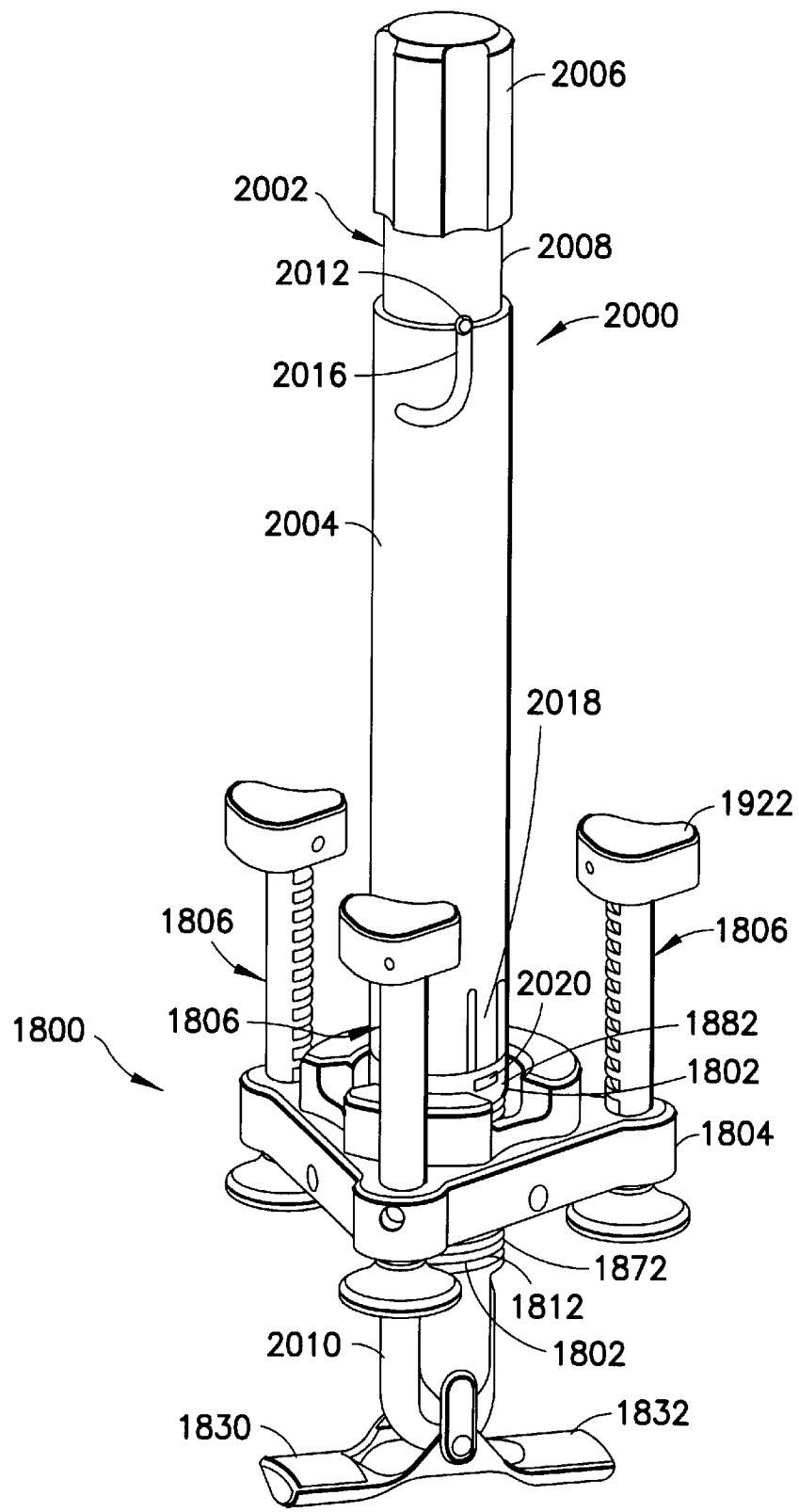
FIG. 57 is a perspective view of the fifth embodiment of the port device, shown with an introducer inserted therein for movement of the port swivels, the introducer positioned such that the swivels are in an open position.
Figure 58:
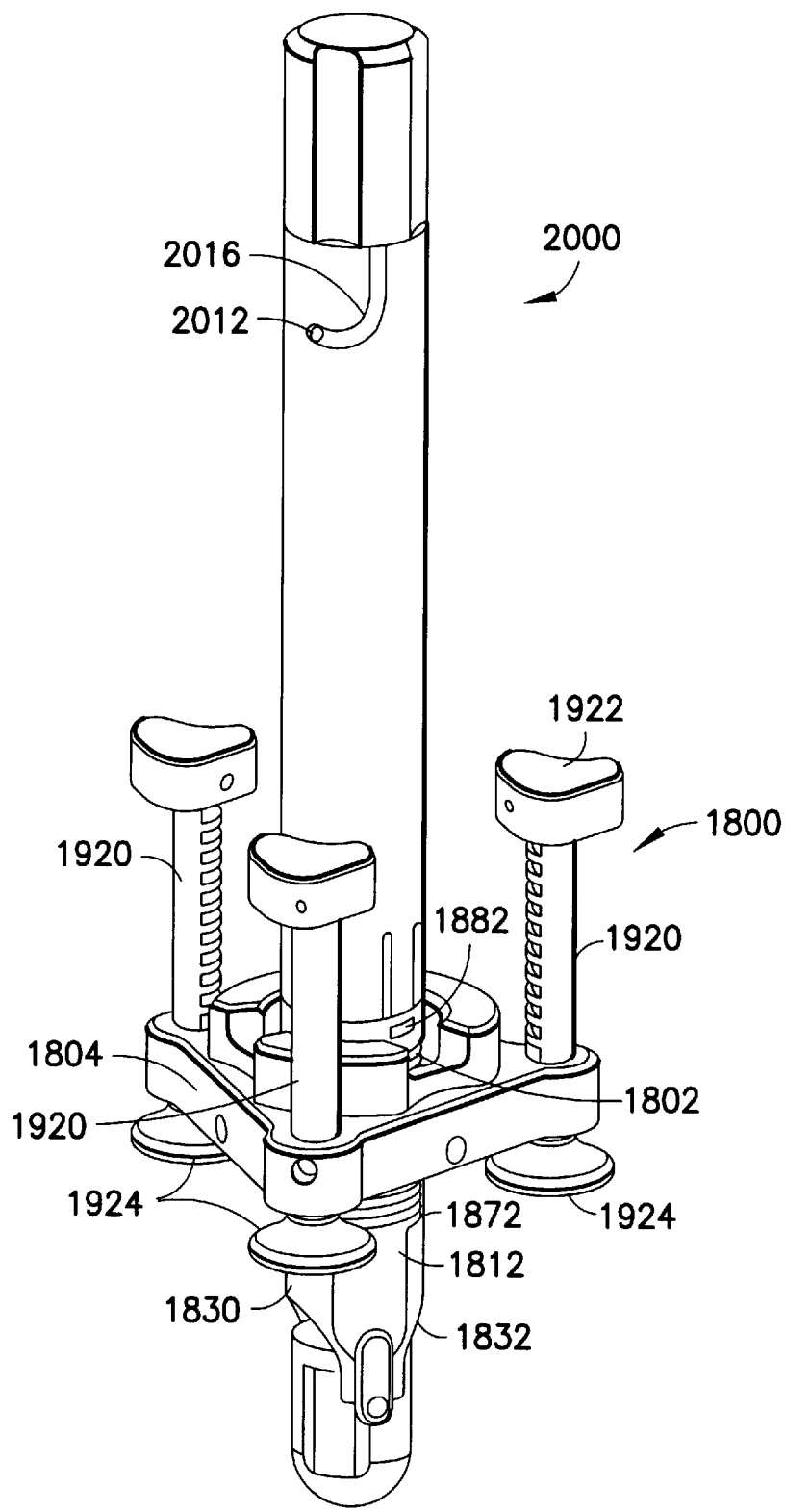
FIG. 58 is a perspective view of the fifth embodiment of the port device, shown with an introducer inserted therein for movement of the port swivels, the introducer positioned such that the swivels are in a closed position.

Turning now to FIGS. 54 through 58, a fifth embodiment of a port device 1800 according to the invention is shown. The port device 1800 includes a port tube (tubular body or port body) 1802 (FIGS. 57 and 58), a platform 1804 (FIG. 54), and a plurality of legs 1806 (FIG. 54). Referring to FIGS. 57 and 58, the port tube 1802, at a distal end, includes a pair of swivels 1830, 1832 coupled to the tube with axle members, as described above (see FIG. 2), and a proximal body 1812 having a plurality of longitudinally-spaced circumferential grooves 1872. The proximal end of the body includes preferably two diametrically opposite catches 1882 for receiving latches of an introducer, and coupling thereto, as described below.

Referring back to FIGS. 54 through 56, the platform 1804 is preferably generally triangular-shaped and includes a central opening 1900 (FIG. 56) in which to receive the port tube 1802, and three peripheral leg holes 1902 preferably located adjacent the corners of the platform in which to receive the legs 1806. Three ratchet pins 1904, each having a beveled lower edge 1905, are evenly spaced about the central opening 1900. The ratchet pins 1904 are biased by respective springs 1906 to extend radially inward into the central opening 1900. Each ratchet pin 1904 includes an upwardly extending convex boss portion 1908. A port tube release collar 1910 is provided within the central opening 1900 and includes a central passageway 1911. The ratchet pins 1904 extend into the central passageway 1911. The collar 1910 also includes a convex groove 1912 over each boss portion 1908. In addition, the collar includes a slot 1914 between each groove 1912. One peg 1916 extends through each slot 1914, and is fixed in the platform, permitting the collar 1910 to be rotated relative to the central opening 1900 a limited amount; i.e., the distance the peg 1916 may travel within the slot 1914. Moreover, the pegs 1916 couple the collar to the platform 1804 and prevent its release. When the collar 1910 is rotated relative to the platform 1804 from a first position in which the center of each groove 1912 is positioned over a respective boss portion 1908, the respective surfaces of the convex grooves contact the boss portions and move the ratchet pins 1904 against the bias of the springs 1906 to retract the ratchet pins from the central opening 1900. The collar 1910 preferably includes upper knob portions 1917 grippable by human fingers to facilitate the limited rotation of the collar 1910 relative to the platform and the resulting 'release' of the ratchet pins.

When the platform 1804 is distally forced over the port tube 1802, the grooves 1872 of the port tube 1802 contact the beveled ratchet pins 1904 and cause radial outward movement of the pins against the bias of the springs 1906. When the platform 1804 is moved a desired distance over the port tube 1802, the relative distal force is removed and the ratchet pins engage within the grooves to prevent proximal movement of the platform relative to the tube. The platform 1804 may then be released from over the port tube 1802 by rotation of the collar 1910 relative to the platform. This configuration permits the platform to be readily and rapidly moved distally along the port tube to a desired location with the ratchet pins locking within the grooves of the port tube to prevent proximal movement of the platform.

Each of the legs 1806 includes a generally cylindrical shaft 1920, an upper knob 1922 facilitating downward (distal) force to be placed on the leg, and a lower foot 1924 which is pivotable on the distal end of the shaft 1920. A portion along a length of the shaft 1920 includes a rack of teeth 1926 defined by grooves 1928 cut parallel to a tangent of the shaft. Each shaft 1920 is provided into a respective leg hole 1902 of the platform 1804. The platform includes, for each leg hole, a ratchet pin 1930 having a convex tip 1932 with a beveled upper surface 1934. The ratchet pin 1930 is biased by a spring 1936 to extend radially into the leg hole 1902. Each leg may be easily and rapidly moved distally relative to the platform 1804 by pushing the leg distally, causing the beveled upper surface 1934 to contact the teeth 1926 and be moved radially inward against the bias of the spring 1936 to permit movement of the leg 1920 through its respective leg hole 1902. However, the legs are prevented from relative proximal movement by the capture of the ratchet pin 1932 in a groove 1928 between the teeth 1926. Each leg may then be released by rotating the leg relative to the platform such that the inner surface of the groove 1928 in which the ratchet pin 1930 seats contacts the tip 1932 of the pin and moves the pin out of the leg hole. When the leg is sufficiently rotated to cause a cylindrical portion of the leg to be facing the ratchet pin 1934, the pin is prevented from entering the leg hole and cannot contact the teeth or enter the grooves, as the teeth and grooves are rotated out of the way. As such, the legs may then be freely moved proximally and distally. It will be appreciated that the legs may be independently moved relative to the platform to permit a variety of longitudinal and angular adjustments. In addition, the legs define a tripod which is extremely stable. Furthermore, the degree of adjustment and clamping ability is also facilitated by the adjustability of the platform relative to the tube.

Figure 31:
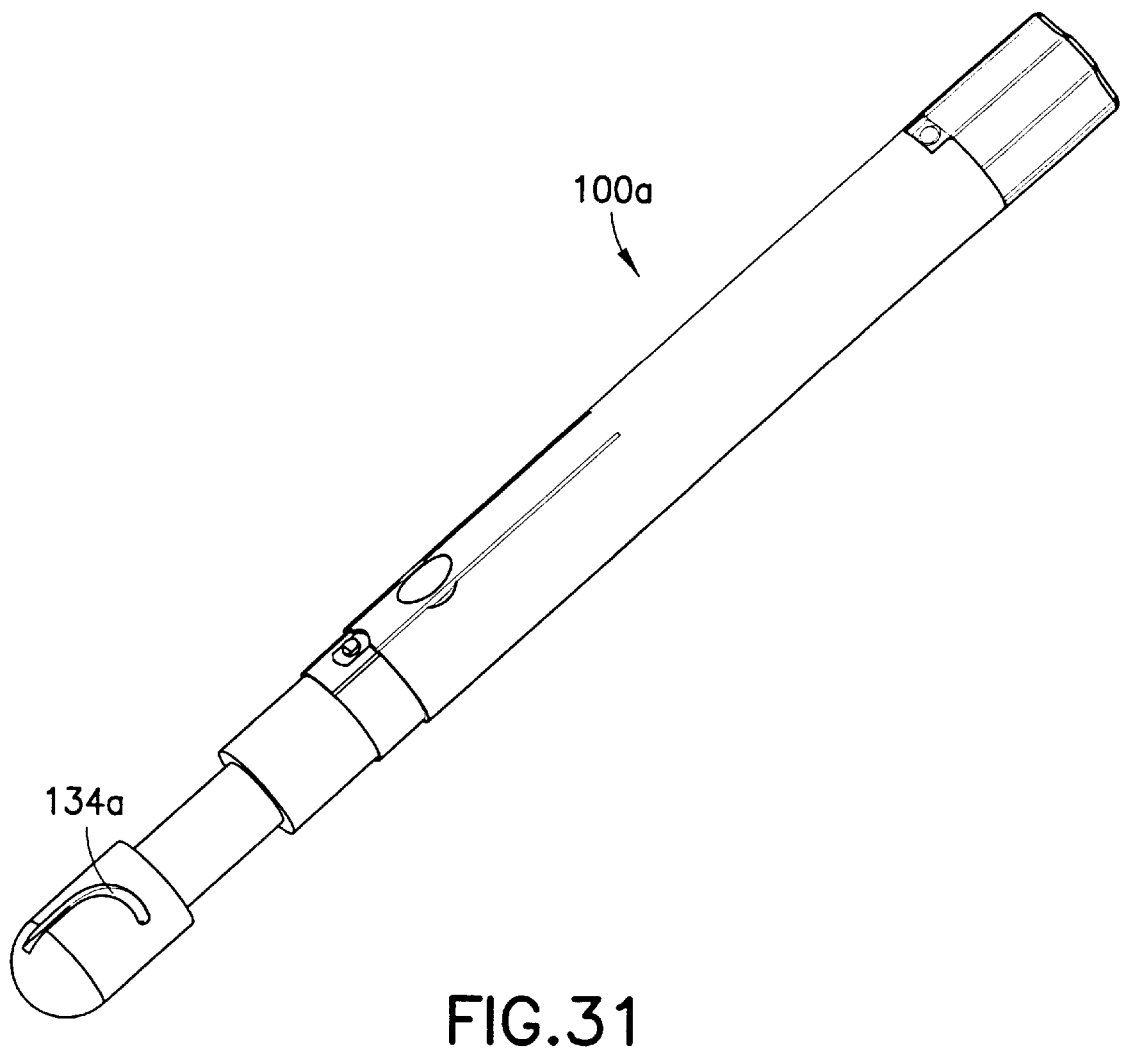
FIG. 31 is a perspective view of a second embodiment of a port introducer according to the invention.

Referring now to FIGS. 57 and 58, an introducer 2000 is coupled to the port device to aid insertion of the port device into the chest wall and to enable movement of the swivels into the clamping positions. The introducer includes a mandrel 2002 extending through a guiding sleeve 2004. The mandrel 2002 includes a handle 2006 at a proximal end, a central shaft portion 2008, and a distal actuator 2010. A pin 2012 is provided in a proximal portion of the shaft and protrudes above the surface of the shaft. The actuator 2010 includes a J-hook groove, as shown with respect to the J-hook groove 134a of the actuator 100a (FIG. 31). The sleeve 2004 includes a proximal J-hook slot 2016 and distal resilient fingers 2018 having tabs or latches 2020 adapted to engage the catches 1882 of the port tube 1802.

In operation, the swivels 1830 and 1832 of the port 1800 are first manually moved into an open configuration. Next, the sleeve 2004 of the introducer 2000 is coupled to the port 1800 by engaging the tabs 2020 of sleeve 2004 in the catches 1882 of the port tube 1802. The mandrel 2002 is then inserted through the sleeve 2004 such that the pin 2012 on the mandrel is aligned with the proximal end of the J slot 2016 of the sleeve. This causes the levers 62 (FIG. 2) of the open configuration swivels to be aligned with the distal end of the J-groove of the actuator 2010. Referring to FIG. 58, the handle 2006 is then moved distally and rotated relative to the sleeve 2004 to move the pin 2012 through the slot 2016 in the sleeve to the distal end of the slot. Consequently, the actuator is moved in a manner which causes the J-groove to guide the levers in a manner which rotates the swivels 1830, 1832 into a closed configuration.

The introducer 2000 is then maneuvered to insert the closed port tube 1802 through an opening in the chest wall. The handle is then operated in an opposite direction to open the swivels 1830, 1832 in the chest wall. The platform 1804 is then moved over the introducer 2000 and ratcheted over the port tube to clamp the chest wall between the open swivels and the feet 1924 of the legs 1920. The legs 1920 may then be ratcheted distally or released to be moved proximally relative to the platform to desirably orient the port tube relative to the chest wall. The introducer is then released by radially inwardly compressing the resilient fingers 2018 to release the tabs 2020 from the catches 1882 and then withdrawing the introducer 2000 from the port tube 1802. Endoscopic instruments may then be inserted through the port tube 1802, as discussed above.

When the procedure is complete, the introducer is again coupled to the port tube, and the platform may be released from over the port tube by releasing the ratchet engagement from the legs and port tube. The introducer is then operated to move the swivels into the closed position and the port tube is withdrawn from the chest wall.

Figure 59:
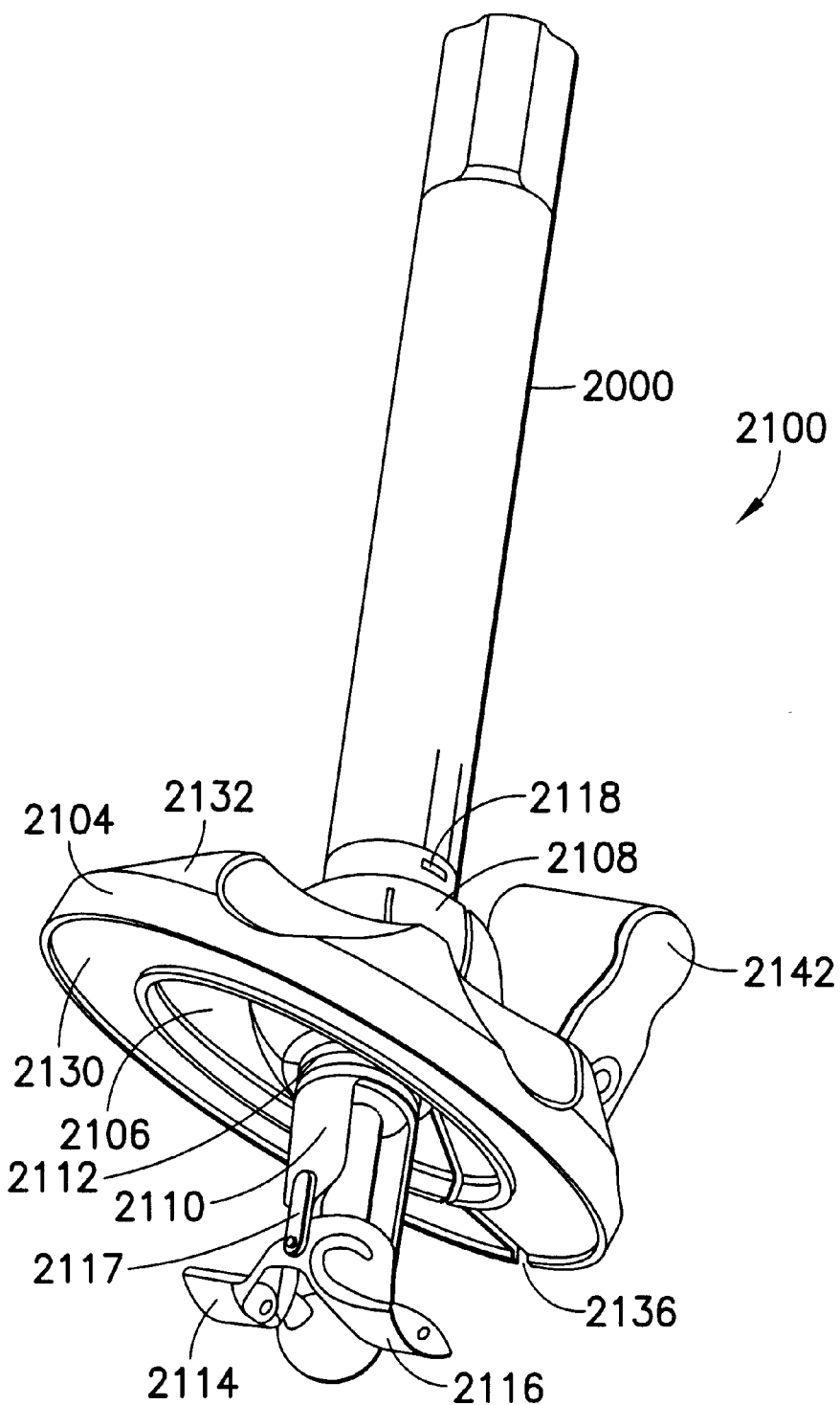
FIG. 59 is a bottom perspective view of a sixth embodiment of the port device, shown with an introducer inserted therein for movement of the port swivels.
Figure 60:
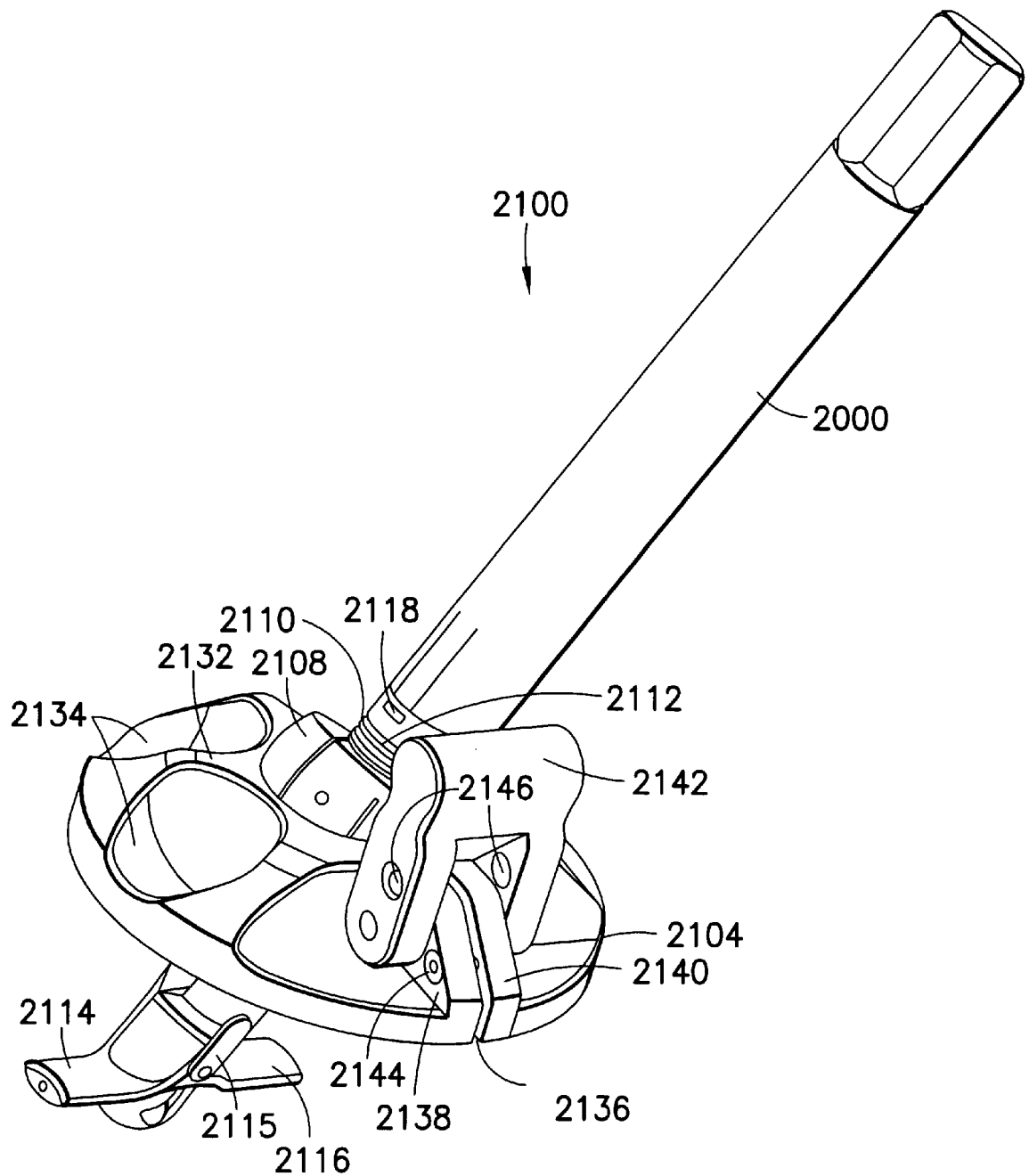
FIG. 60 is a top perspective view of the sixth embodiment of the port device, shown with an introducer inserted therein for movement of the port swivels.

Turning now to FIGS. 59 and 60, a sixth embodiment of the port device 2100 includes a base 2104 defining a socket 2106, an oblate ball element 2108 rotatable within the socket, and a tubular port body 2110 extending through the ball element 2108.

The port body 2110 includes a plurality of circumferential grooves 2112 along a portion of its length. At the distal end of the port body 2110, a pair of swivels 2114, 2116 are coupled to posts 2115, 2117 at the distal end of the port body, as described in more detail below. The proximal end of the body 2110 includes preferably two diametrically opposite catches 2118 for receiving latches of an introducer 100a (FIG. 31) or 2000 (FIG. 57), and coupling thereto, as described above with respect to the fifth embodiment.

Figure 61:
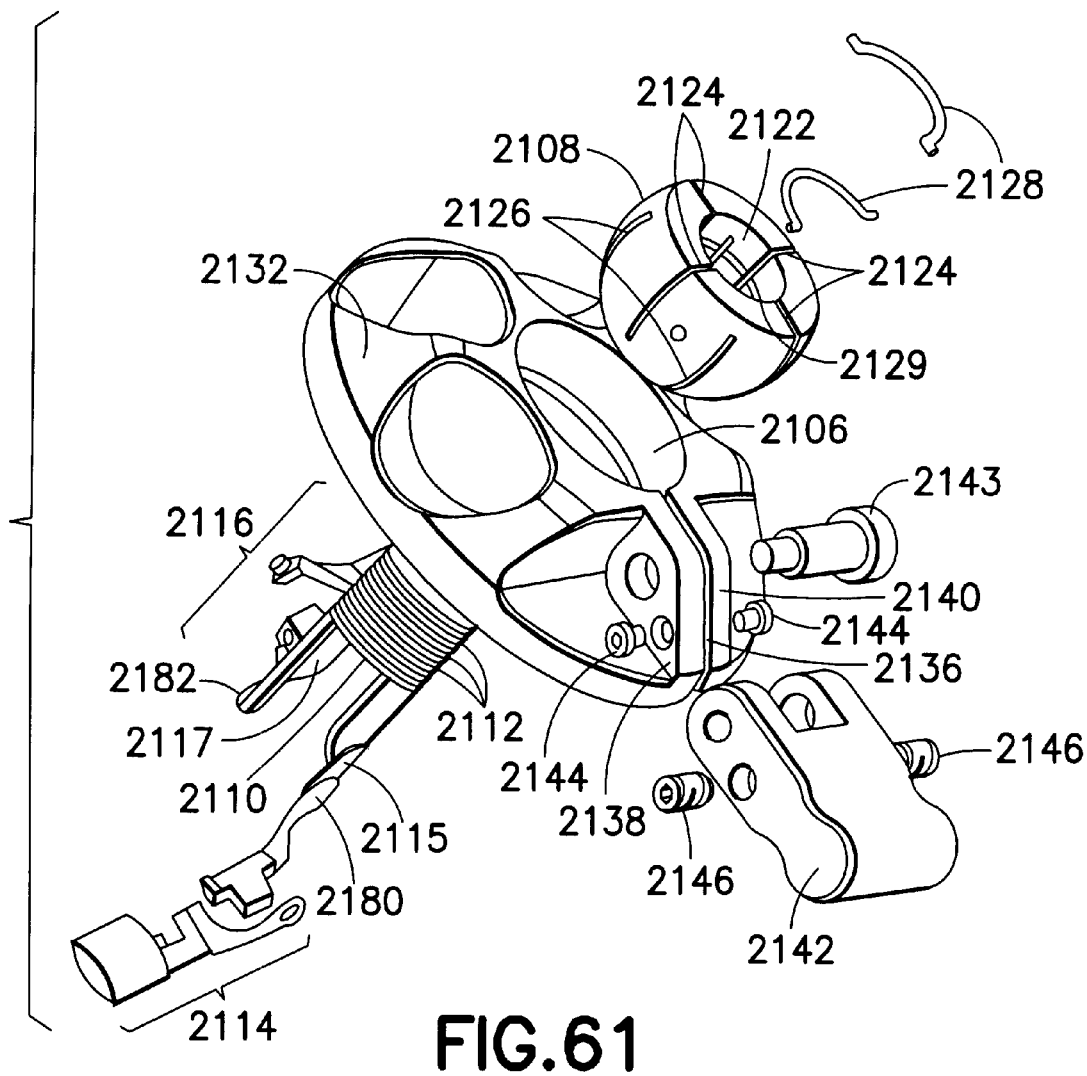
FIG. 61 is an exploded perspective view of the sixth embodiment of the port device.

Referring to FIG. 61, the oblate ball element 2108 includes a hole 2122 extending between its ends, and eight slits 2124, 2126 partially extending into the element from the ends. A first four of the slits 2124 are provided at ninety degrees separation from one another at one end of the element, and a second four of the slits 2126 (only two shown) are provided at ninety degrees of separation from one another, but offset by forty-five degrees relative to the first four slits, in the other end of the element. As such, the ball element 2108 may be compressed at the slits 2124, 2126 to reduce the diameter of the hole 2122. The ball element 2108 is also provided with two generally omega-shaped ring springs 2128 seated within channels 2129 inside the ball element such that only a small portion of the springs protrudes within the hole. As stated above, the port body 2110 extends within the ball element 2108; i.e., through the hole. When the ball 2108 is in a substantially noncompressed state (FIGS. 59 and 60), the springs 2128 function as detents with respect to the grooves 2112 in the port body. Thus, the port body 2110 can be moved longitudinally within the hole of the ball element when subject to a small longitudinal force relative to the ball element.

Figure 62:
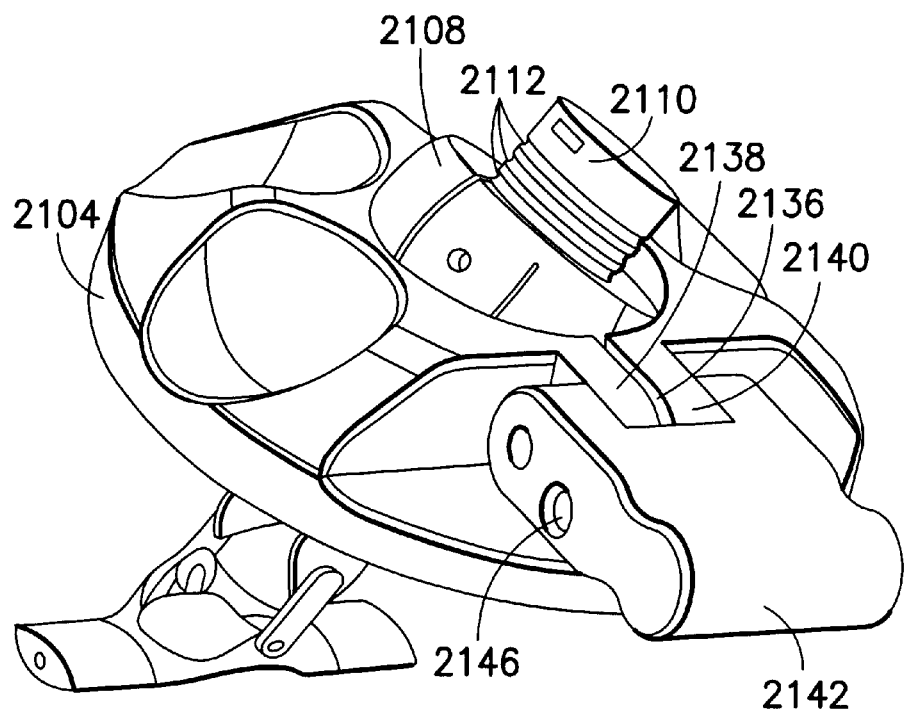
FIG. 62 is a perspective view of the sixth embodiment of the port device, shown with the port locked in a position relative to the base.
Figure 63:
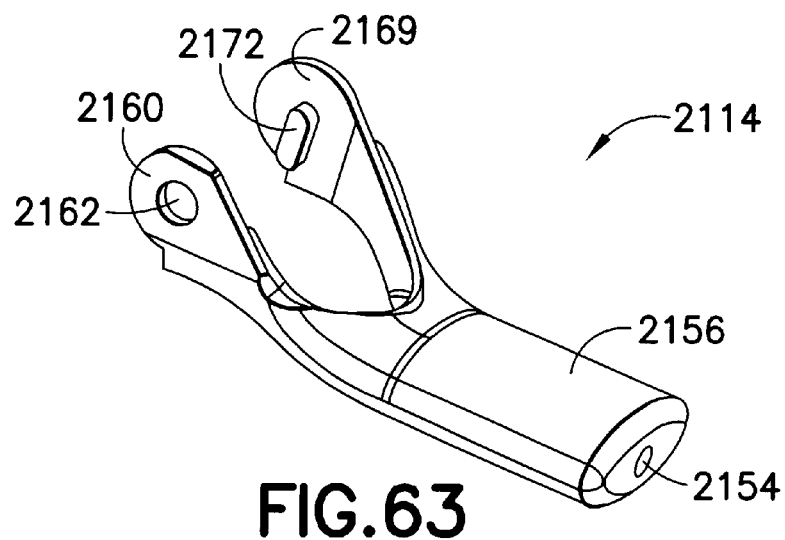
FIG. 63 is a perspective view of another embodiment of a swivel for any of the port devices.
Figure 64:
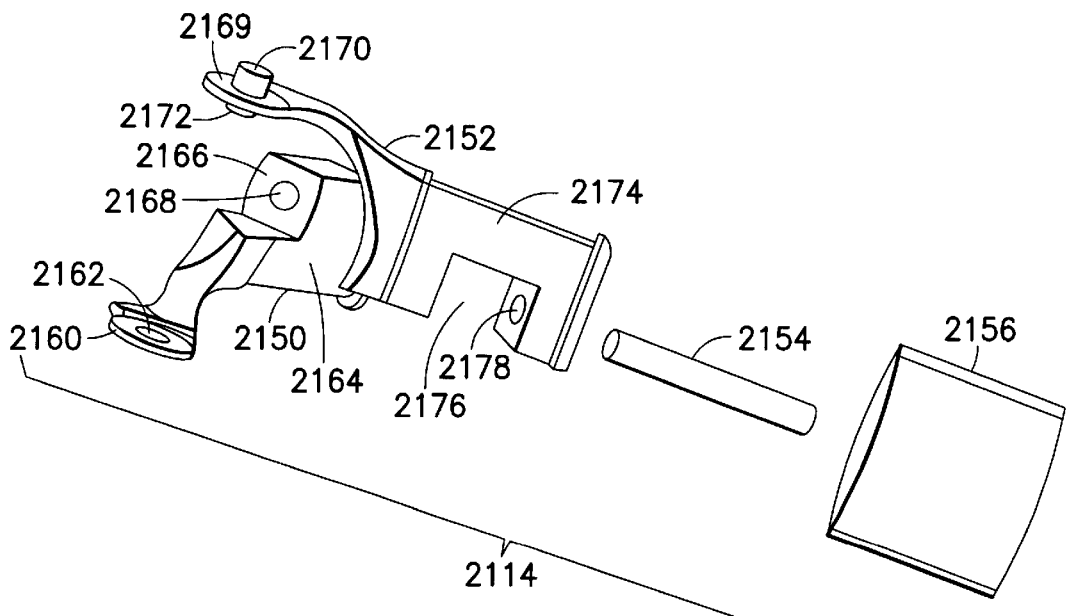
FIG. 64 is an exploded perspective top view of the swivel of FIG. 63.
Figure 65:
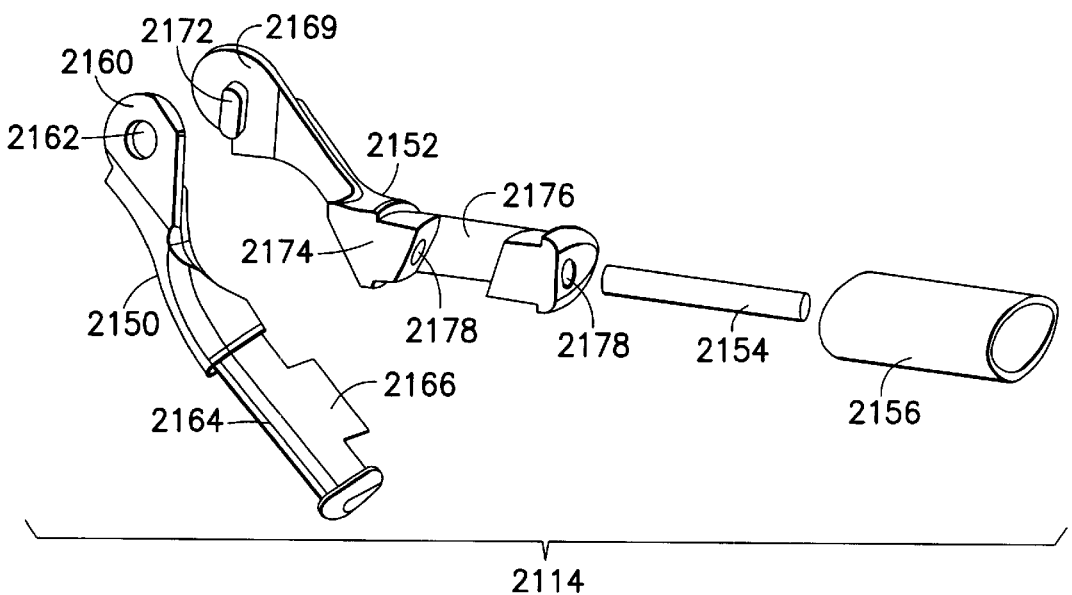
FIG. 65 is an exploded perspective side elevation view of the swivel of FIG. 63.

Referring to FIGS. 59, 60 and 61, the base 2104 includes a generally circular footprint 2130 (FIG. 59) sized to seat on the chest wall, an upper surface 2132 provided with gripping structure 2134 to facilitate manipulation of the base by hand, and the preferably centrally located socket 2106. The base 2104 also includes a small radial gap 2136 extending from the socket 2106 to its periphery. An upstanding wall 2138, 2140 is provided on each side of the gap 2136, and a generally U-shaped locking lever 2142 is pivotably coupled with a hinge pin 2143 to the base 2104 at the upstanding walls. Each wall 2138, 2140 additionally includes a preferably flat head hex-socket screw 2144 provided therein which functions as a clamping surface. The locking lever 2142 includes two inwardly extending oval head set screws 2146 which each function as a clamping cam relative to the flat head screw clamping surface. Referring to FIGS. 60, 61 and 62, when the locking lever 2142 is rotated relative to the base 2104, the oval head screws 2146 contact the flat head screws 2144 and compress the base 2104 at the upstanding walls 2138, 2140 to reduce the size of the gap 2136. The flat head screws 2144 provide a hard surface for the oval head screws 2146 to move over. Furthermore, the socket openings of the flat head screws 2146 function to lock head of the oval head screws. The ball element 2108 in the socket 2106 is thereby locked relative to the base 2104. Moreover, the ball element 2108 is compressed about the port body 2110 to interlock the springs 2128 in a groove 2112 of the port body, and thereby lock the port body 2110 relative to the ball element 2108. As such, the locking lever secures the angular and longitudinal location of the port body relative to the base.

If insufficient compression or too much compression is provided by movement of the locking lever into the locked position, the oval head screws can be adjusted to extend further or extend less from the locking lever and provide additional or less clamping force, as the case may be. In addition, as an alternative to using a flat head screw, a groove may be molded in the upstanding walls, the groove preferably being provided with a dimple in which the oval head screws may engage to lock the locking lever in the clamped position.

Referring now to FIGS. 59 through 65, the sixth embodiment of the port is shown with swivels 2114, 2116. With respect to swivel 2114 (swivel 2116 preferably being exactly the same), swivel 2114 comprises first and second interengaging swivel elements 2150, 2152, a retaining pin 2154, and a preferably elastomeric sleeve 2156. The first swivel element 2150 includes a flange 2160 having a hole 2162 and a body portion 2164 having a key portion 2166 and a bore 2168 extending through the key portion. The second swivel element 2152 includes a flange 2169 having an outer axle 2170 (sized to fit within the hole 2162 of swivel 2116) and an elongate inner swivel ear 2172 adapted to be engaged within the J-groove of the introducer 100a (FIG. 31). The second swivel element 2152 also includes a body portion 2174 having a channel 2176 sized and shaped to receive the key portion 2166 of the first swivel element 2150, and a bore 2178 extending through the body portion 2174. The channel has a radius of curvature relative to the axle 2170, and the key is formed with a radius of curvature relative to the hole 2162.

According to a preferred swivel assembly, a hole 2162 of a first element 2150 is provided on an axle 2170 of a second swivel element 2152, with the respective body portions oppositely directed. The axle 2170 is positioned within the pivot hole 2180 (FIG. 61) of the port body. A second similar assembly is made and the boss thereof is positioned within pivot hole 2182 of the port body. It is appreciated that two first swivel elements and two second swivel elements are thusly coupled to the port body, but the elements are configured as four independently rotatably parts, and are not as of yet the desired swivels. Appropriate first and second swivel elements 2150, 2152 are then rotated relative to each other such that the key portion 2166 of the first swivel element enters the channel 2176 of the second swivel element and defines the shape of the desired swivel 2114 (compare FIGS. 65 and 63). The pin 2154 is then inserted into the bores 2168, 2178 of the first and second swivel elements to lock the elements together. The sleeve 2156 is provided over the body portions of the swivel elements to complete swivel 2114 and provide a soft contact surface for contact against the inner chest wall. The same final assembly is made with respect to swivel 2116. The multi-piece swivel design provides several advantages over the single-piece swivel described above. First, the swivels may be coupled to the posts 2115, 2117 of the port body without forcing the posts apart during assembly. Second, the swivel ear 2172 may be formed as an integral part of the swivel, rather than as a separate piece when the parts are machined. It is nevertheless appreciated that the swivel ear may be formed as an integral part of a single-piece swivel when the swivel is cast.

While the port device has been disclosed with various swivel elements, it will be appreciated that other swivel elements, and means for opening the swivel elements, including springs and mechanical systems may be used as well. In addition, while particular types of connecting means for coupling devices, e.g., the introducer and surgical instruments to the port have been disclosed, it will be understood that other connecting means can be used. Also, while various means for orienting the port device relative to the heart wall have been disclosed, it will be appreciated that other such orienting means can be used was well. Furthermore, it will be appreciated that any one or more of the features of the individual port device embodiments may be incorporated into the other embodiments.

Figure 16:
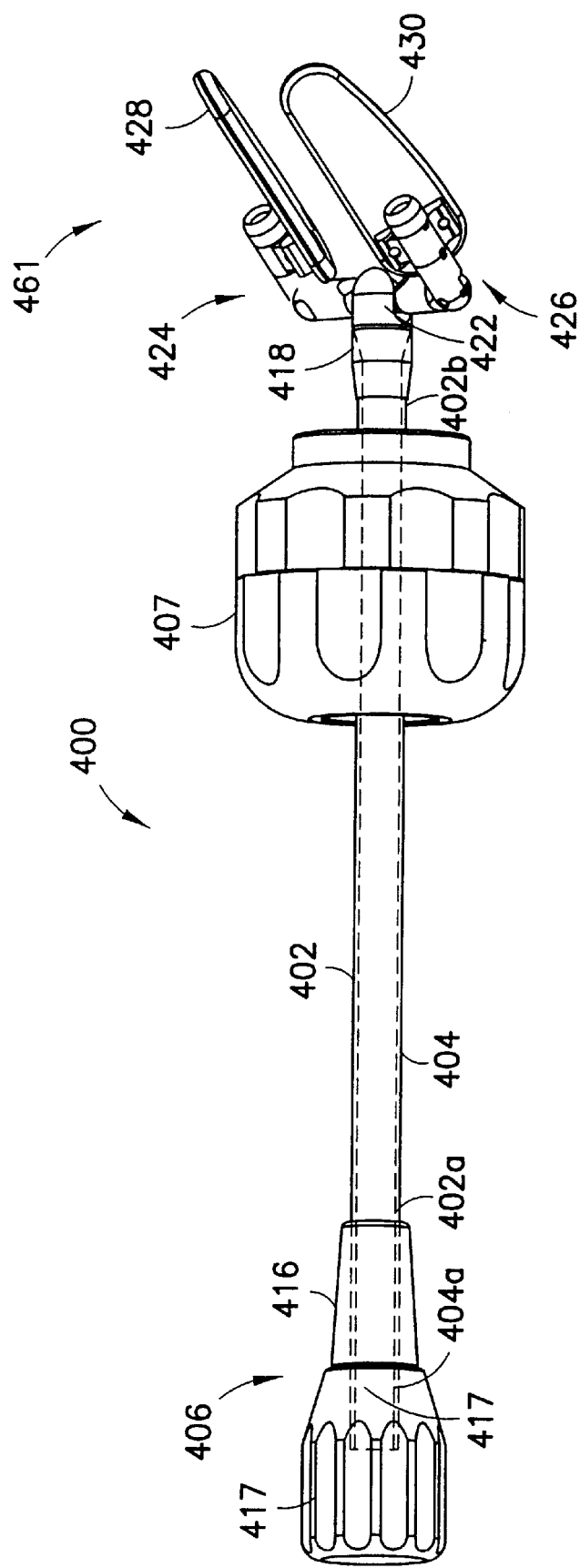
FIG. 16 is a side perspective view of a first embodiment of a heart stabilizer device according to the invention.

Turning now to FIG. 16, a first embodiment of the heart stabilizer 400 preferably includes a hollow shaft 402, a rod 404 extending through the shaft, and a proximal control handle 406 coupled to the proximal ends of the shaft 402 and rod 404 to move the rod longitudinally within the shaft, as described in more detail below. The shaft 402 and rod 404 are keyed (not shown) such that the rod cannot rotate relative to the shaft. A shaft lock 407 is provided about the shaft 402 and operates to lock the heart stabilizer 400 to a port device, such as port devices 10 (FIG. 1) and 210 (FIG. 13), and also permits locking the shaft 402 in numerous longitudinal and angular positions relative to the port device.

Figure 17:
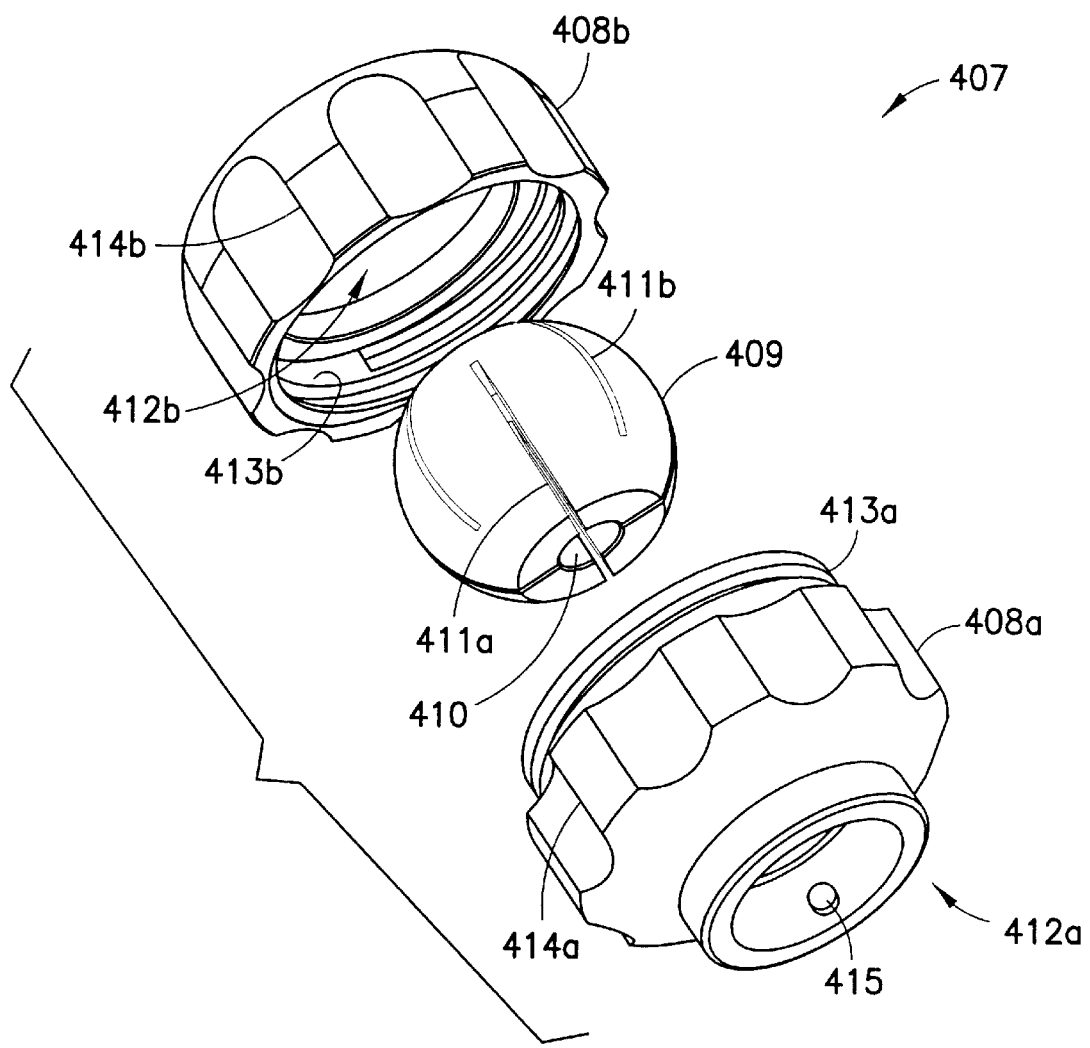
FIG. 17 is an exploded perspective view of the shaft lock of the heart stabilizer device of FIG. 16.

More particularly, referring to FIGS. 16 and 17, the shaft lock 407 includes a port connector 408a, a cap 408b, and a ball element 409 between the port connector and cap. The ball element 409 includes a shaft bore 410, a first set of diametric slots 411a in one end of the ball element, and a second set of diametric slots 411b in the other end of the ball element. The two sets of slots 411a and 411b permit radial compression of the ball element 409 to cause the diameter of the shaft bore 410 to decrease. The port connector 408a and cap 408b each include an opening 412a, 412b, a mating means 413a, 413b, e.g., threads, for mating with each other, and a finger gripping structure 414a, 414b to facilitate relative rotation of the port connector and cap about the mating means. The port connector 408a also includes a port mating structure 415, e.g., a bayonet, for mating with the female bayonet coupling 283 of a port 210 (FIG. 14). The shaft 402 extends through the shaft bore 410 and, when the port connector 408a, 408b are loosely mated with each other, the shaft and ball element 409 may be pivoted relative to the port connector and cap, and the shaft may be moved longitudinally within the bore 410 relative to the shaft lock. When the cap 408b is tightened on the port connector 408a, the ball element 409 and shaft 402 are locked in their respective positions.

Referring to back to FIG. 16, the control handle 406 includes a knob mount 416 fixedly coupled to the proximal end 402a of the shaft 402, and a knob 417 rotatably coupled to the mount 416. The knob 416 includes a threaded bore 417, and the proximal end 404a of the rod 404 is threaded, and threadably engaged within the bore of the knob 417. The rotation of the knob 417 relative to the mount 416 causes the rod 404 to move longitudinally relative to the shaft 402, as the keyed rod cannot rotate relative to the shaft.

Figure 18:
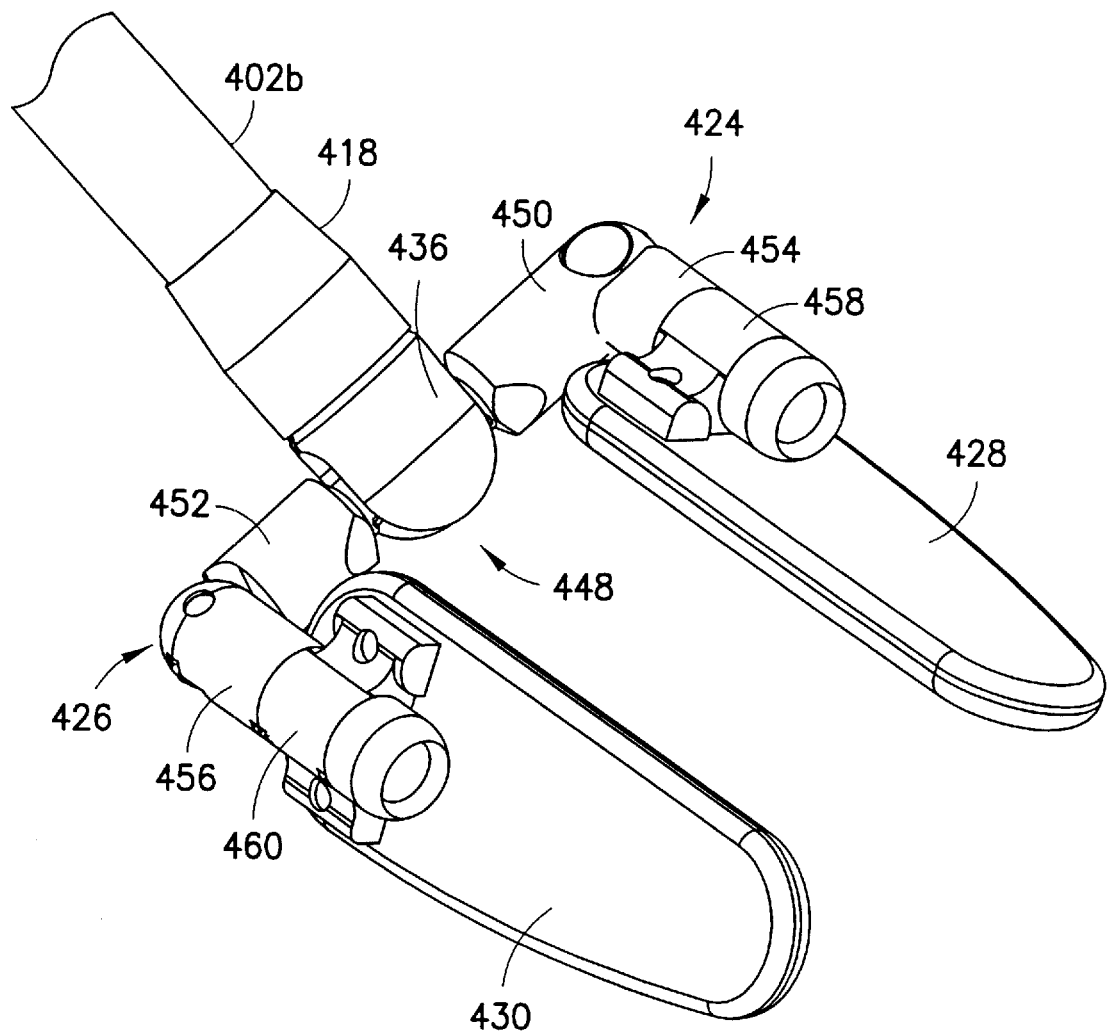
FIG. 18 is a perspective view of the stabilizing mechanism at the distal end of the heart stabilizer device of FIG. 16.
Figure 19:
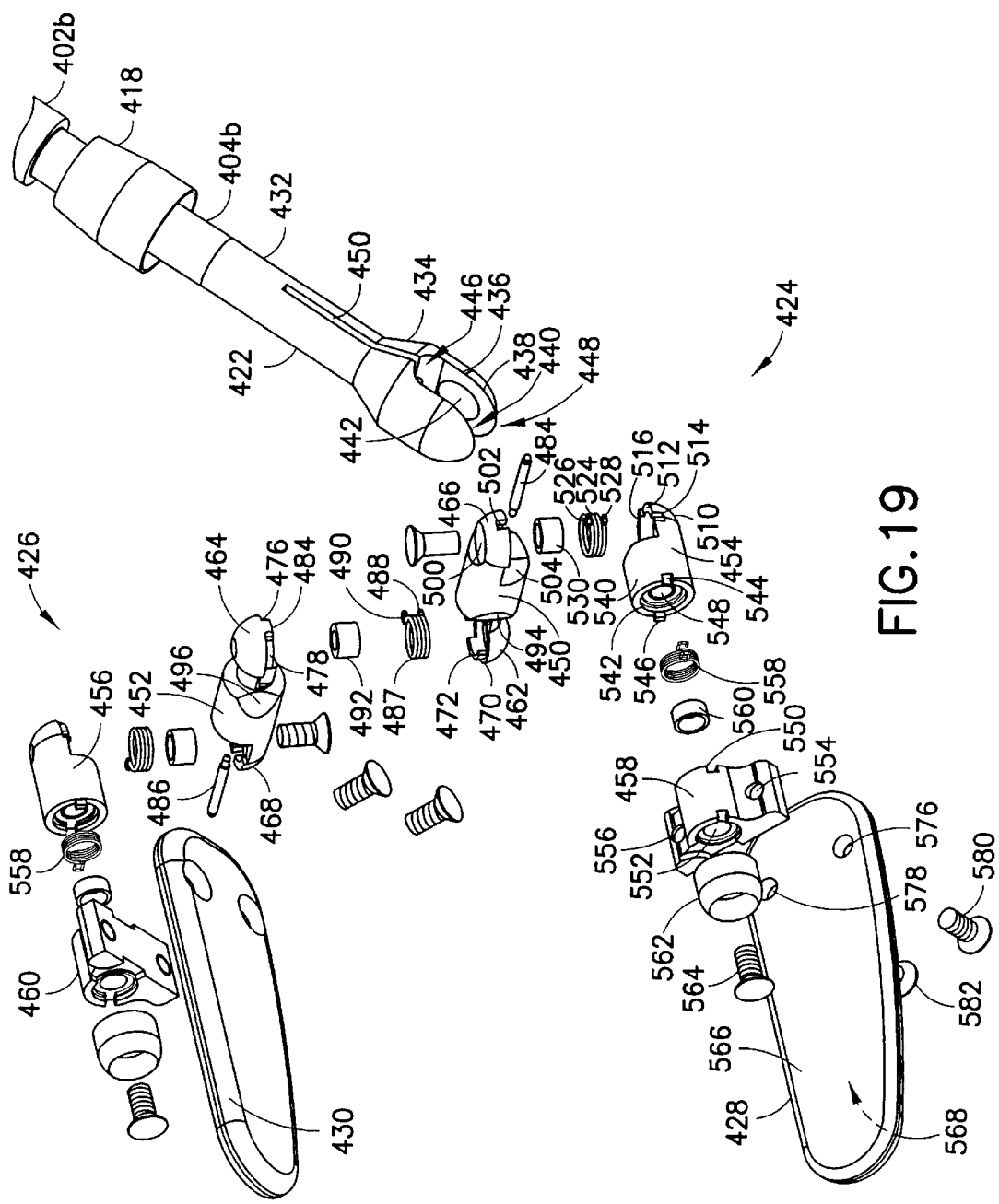
FIG. 19 is an exploded perspective view of the stabilizing assembly of the heart stabilizer device of FIG. 16.

Referring now to FIGS. 16, 18 and 19, the distal end 402b of the shaft 402 is provided with a collar 418. The distal end 404b of the rod 404 is coupled to a clevis 422. The clevis 422 includes a post portion 432 coupled to the rod 404, a frustoconical portion 434, and a U-shaped socket 436 including side walls 438, 440 with spherical concavities 442, a back wall 446, and a front opening 448 extending through an approximately 180° arc. A slot 450 extends from the back wall 446, through the frustoconical portion 434, and into the post portion 432. When the rod 404 is moved proximally relative to the shaft 402, by operation of the handle 406, the collar 418 rides against the frustoconical portion 434 of the clevis 422, causing compression of the socket 436. Conversely, when the rod 404 is moved distally relative to the shaft 402, the frustoconical portion 434 of the clevis 422 is released from the collar, permitting the socket 436 to slightly expand.

Referring to FIGS. 18 through 21, two articulating arms 424, 426 are coupled in the socket 436 of the clevis, and a rotatable stabilizing foot 428, 430 is coupled to the end of each arm. The first and second articulating arms 424, 426 each include an upper arm 450, 452, a lower arm 454, 456, and a wrist mount 458, 460. Stabilizing feet 428, 430 are coupled to the wrist mounts, 458, 460, respectively. The articulating arms 424, 426 and the feet 428, 430 together define a stabilizing assembly 461.

More particularly, each of the first and second upper arms 450, 452 includes a partly hollow, generally hemispherical shoulder 462, 464 at one end and an upper elbow portion 466, 468 at the other end. The first shoulder 462 (of the first upper arm) includes rim 470 defining a first upper cam 472, and the second shoulder 464 (of the second upper arm) includes a rim 476 defining a second upper cam 478. In addition, each of the first and second upper arms includes a pin bore 480, 482 extending longitudinally through the arms. Lock pins 484, 486, which function to limit the movement of the first and second upper arms 450, 452 relative to each other as described in more detail below, are provided within the pin bores 480, 482.

The first and second shoulders 462, 464 are oriented and configured such that they together substantially define a sphere. A shoulder spring 487 is positioned within the sphere defined by the shoulders, and the ends 488, 490 of the spring 487 are coupled to and about the rims 470, 476, respectively, with the spring 487 under helical compression to urge the upper arms 450, 452 away from each other. A spacer 492 is provided within the spring 487 to stabilize the spring within the shoulders. The shoulders together are provided in the socket 436, with each hemispherical shoulder residing partially within a respective one of the concavities 442. While the shoulders 462, 464 appear to form a ball within the socket 436, it will be appreciated that the shoulders provide additional function over a ball in that the two upper arms 450, 452 are permitted to independently rotate relative to each other at the shoulders. The spring 487 is adapted to bias the upper arms 450, 452 into an open position in which the two are in alignment; i.e., at substantially 180° relative to each other. Each upper arm 450, 452 also includes a front bevel 494, 496. As such, when the upper arms are moved against the bias of the spring 487 toward each other, an angle α as small as approximately 45°, and preferably 47°, may be defined therebetween (FIG. 20), with the bevels 494, 496 minimizing interference between the two upper arms which would otherwise limit the ability to define such a small angle α therebetween.

The description of the lower arms 454, 456 and the coupling of the lower arms to the upper arms will now be described with respect to upper arm 450 and lower arm 454 of the first articulating arm 424, with it being understood that the lower arms and their couplings of the second articulating arm 426 are each substantially the same as in the first articulating arm, but installed upside down relative to the first articulating arm.

The upper elbow portion 466 of upper arm 450 is rotatably coupled to a lower elbow portion of lower arm 454. The upper elbow portion 466 is generally hemispherical in shape and includes a countersunk screw hole 500 and a first elbow spring catch 502. The upper arm 454 is provided with a bevel 504 adjacent the upper elbow portion 466. The lower arm 454 includes a generally hollow, substantially hemispherical lower elbow portion 510 which mates with the upper elbow portion 466 of the upper arm 450. The lower elbow portion 510 includes a rim 512 defining a second elbow spring catch 514, and a lower arm cam 516 including a cam lock 518 and a cam stop 520. The elbow portion 510 also includes a threaded screw hole 522.

An elbow spring 524, under helical tension, is provided within the upper and lower elbow portions 466, 510. The elbow spring 524 includes ends 526, 528 which are coupled in the first and second elbow spring catches 502, 512, respectively, biasing the upper and lower arms toward a configuration having a relatively smaller angle therebetween. A tubular spacer 530 is provided within the elbow spring 524 to stabilize the spring within the shoulders and provide a pathway for a screw 532 which extends into the screw hole 500 and is threadably engaged in screw hole 522 to secure the upper and lower arms together in a manner which permits the lower arm to pivot relative to the upper arm.

The lower end of the lower arm includes an upper wrist portion 540 provided with a rim 542 oriented orthogonally to the rim 512, and a threaded bore 548. The rim 542 defines a first wrist spring catch 544 and a stop 546.

The wrist mount 458 includes a second wrist spring catch 550, a throughbore 552, and two threaded mounting holes 554, 556; one provided on either side of the throughbore 552. A wrist spring 558 is provided about a spacer 560 between the upper wrist portion and the wrist mount and engages the first and second wrist spring catches. The wrist spring 558 is biased to rotate the wrist mount 458 clockwise relative to the upper wrist portion 540 when viewed in the direction of the lower arm 454 toward the wrist mount 458. A wrist spring 558' in the second arm 426 rotates a respective wrist mount in an opposite direction such that the wrist mounts are urged to rotate away from each other.

A collar 562 is provided in alignment with the throughbore 552, and a screw 564 extends through the collar 562 and throughbore 552 and is secured in the threaded bore 548 of the upper wrist portion 540.

The foot 428 includes an outer surface 566, a contact surface 568, and two spaced apart bores 576, 578 which align with the threaded bores 554, 556 of the wrist mount 458. The foot 428 is coupled at its outer surface 566 to the wrist mount 458 with screws 580, 582 extending into the bores 576, 578 and threadably engaged within bores 554, 556 of the wrist mount 458.

Figure 20:
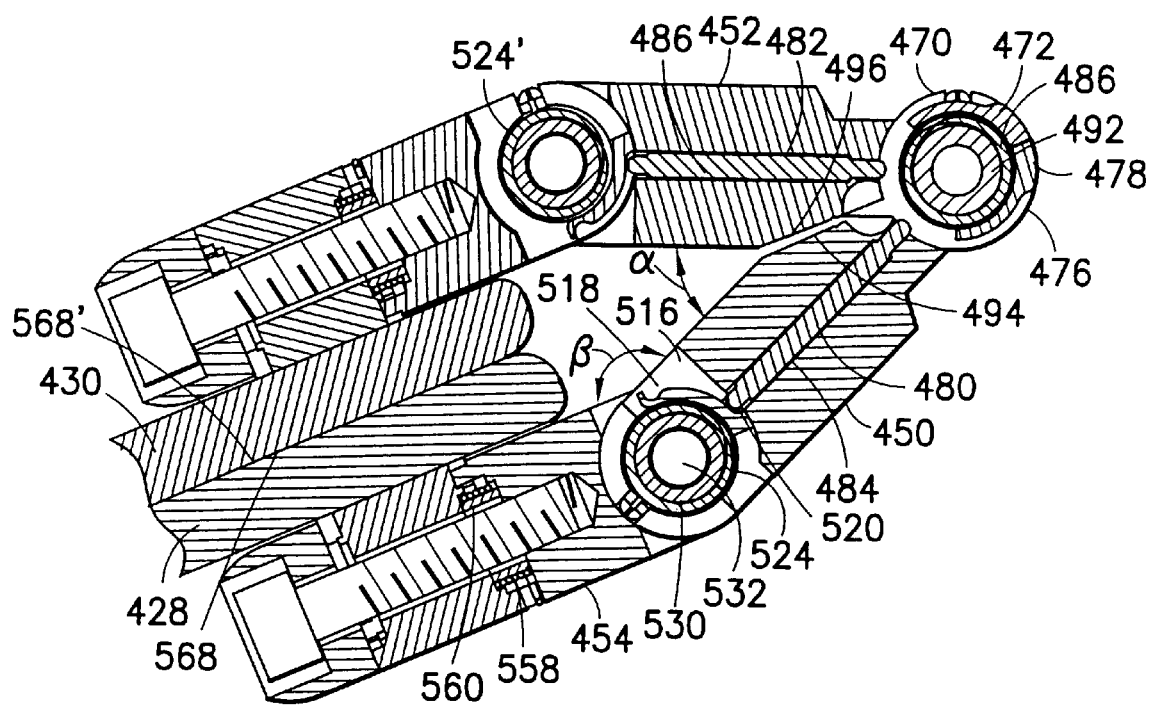
FIG. 20 is a broken longitudinal section view of the shoulders and upper arms of the stabilizing assembly of the heart stabilizer device of FIG. 16 shown in a closed position.
Figure 21:
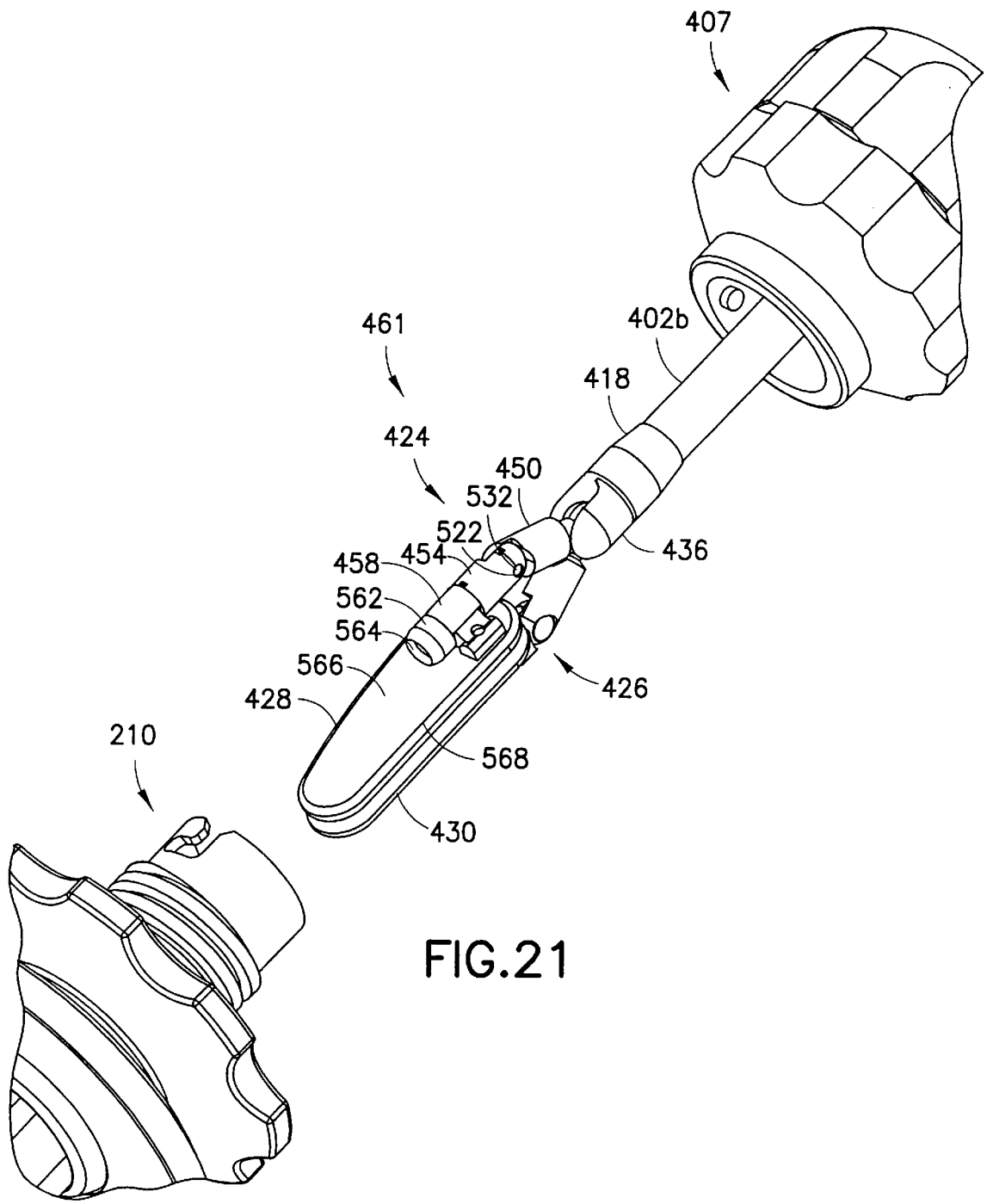
FIG. 21 is a broken bottom perspective view of the stabilizing assembly of the heart stabilizer device of FIG. 16 shown in a closed position and a port device according to the invention.

The operation of the heart stabilizer 410 and particularly the stabilizing assembly 461 will now be described, with reference numerals terminating in a prime referring to elements of the second articulating arm. Referring to FIGS. 20 and 21, the articulating arms 424, 426 and feet 428, 430 are manually folded into the illustrated configuration. That is, the upper arms 450, 452 are folded about the shoulders, and the feet 428, 430 are rotated inward toward each other such that the respective contact surfaces 568, 568' and in contact. In this configuration the upper arms 450, 452 have an angle α of approximately 47°, and the feet 428, 430 are oriented substantially parallel to the shaft 402 of the heart stabilization device 410. The handle 406 is then operated to cause the collar 418 to compress the socket 436 about the shoulders 462, 464 of the upper arms and thereby lock the upper arms 450, 452, lower arms 454, 456, and feet 428, 430 in their relative positions and present a relatively small cross-sectional area for insertion through a port 210.

Figure 22:
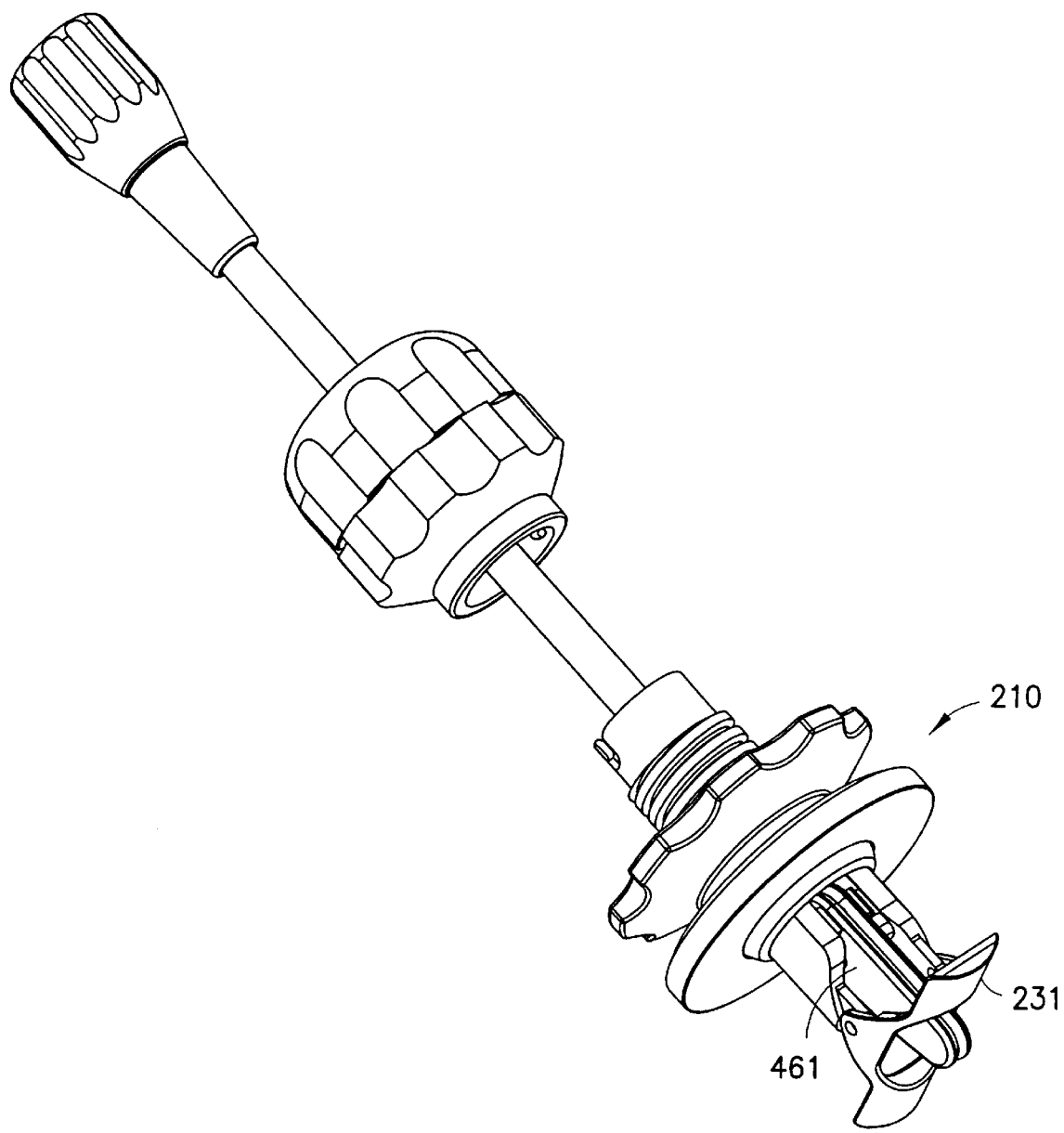
FIG. 22 is a perspective view of the heart stabilizer device, with the stabilizing assembly shown in a folded configuration and being inserted into the port device of the invention.
Figure 23:
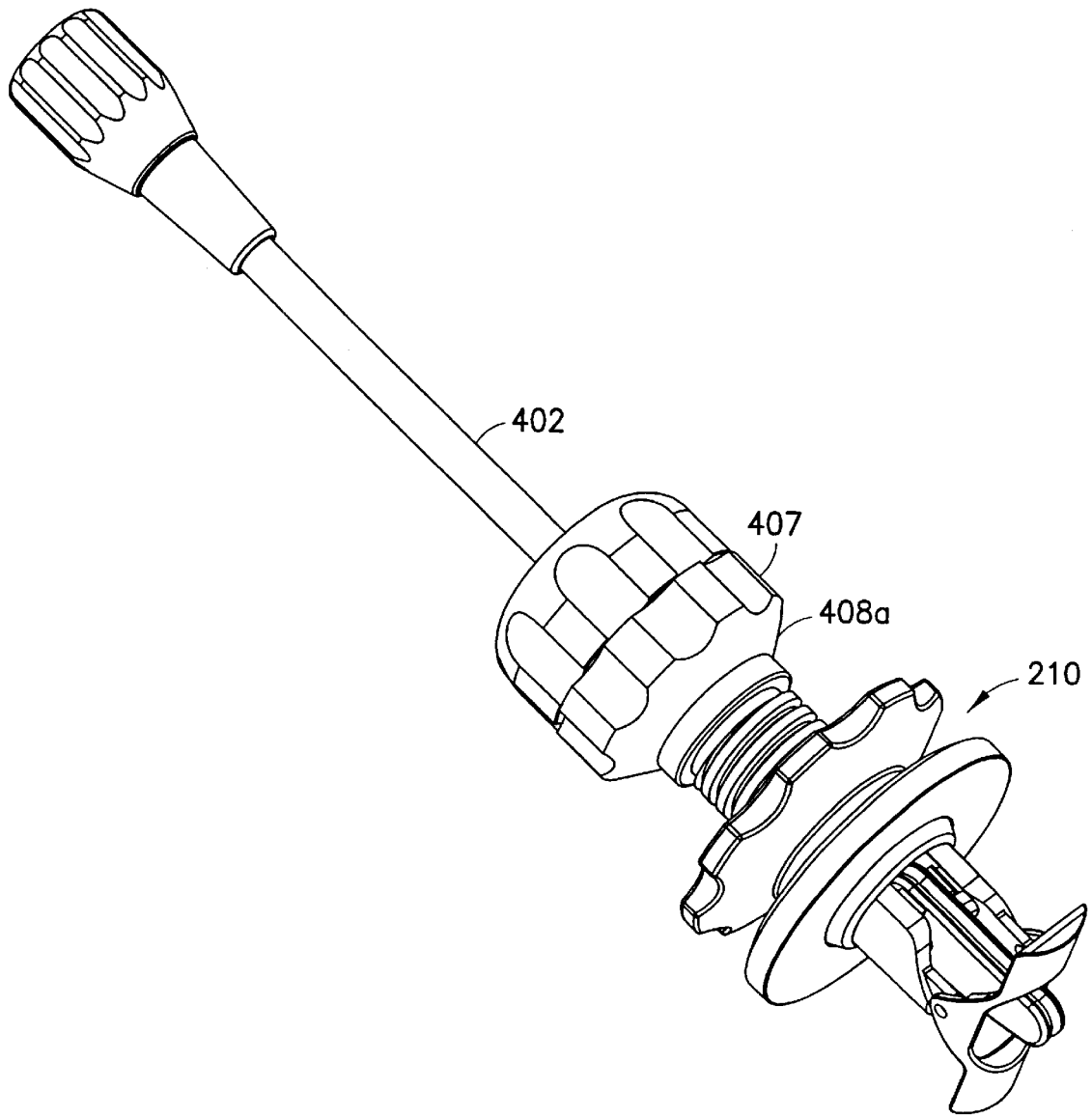
FIG. 23 is a perspective view of the heart stabilizer device, with the stabilizing assembly shown in a folded configuration and being inserted into the port device of the invention and also with a shaft lock being coupled to the port device.
Figure 24:
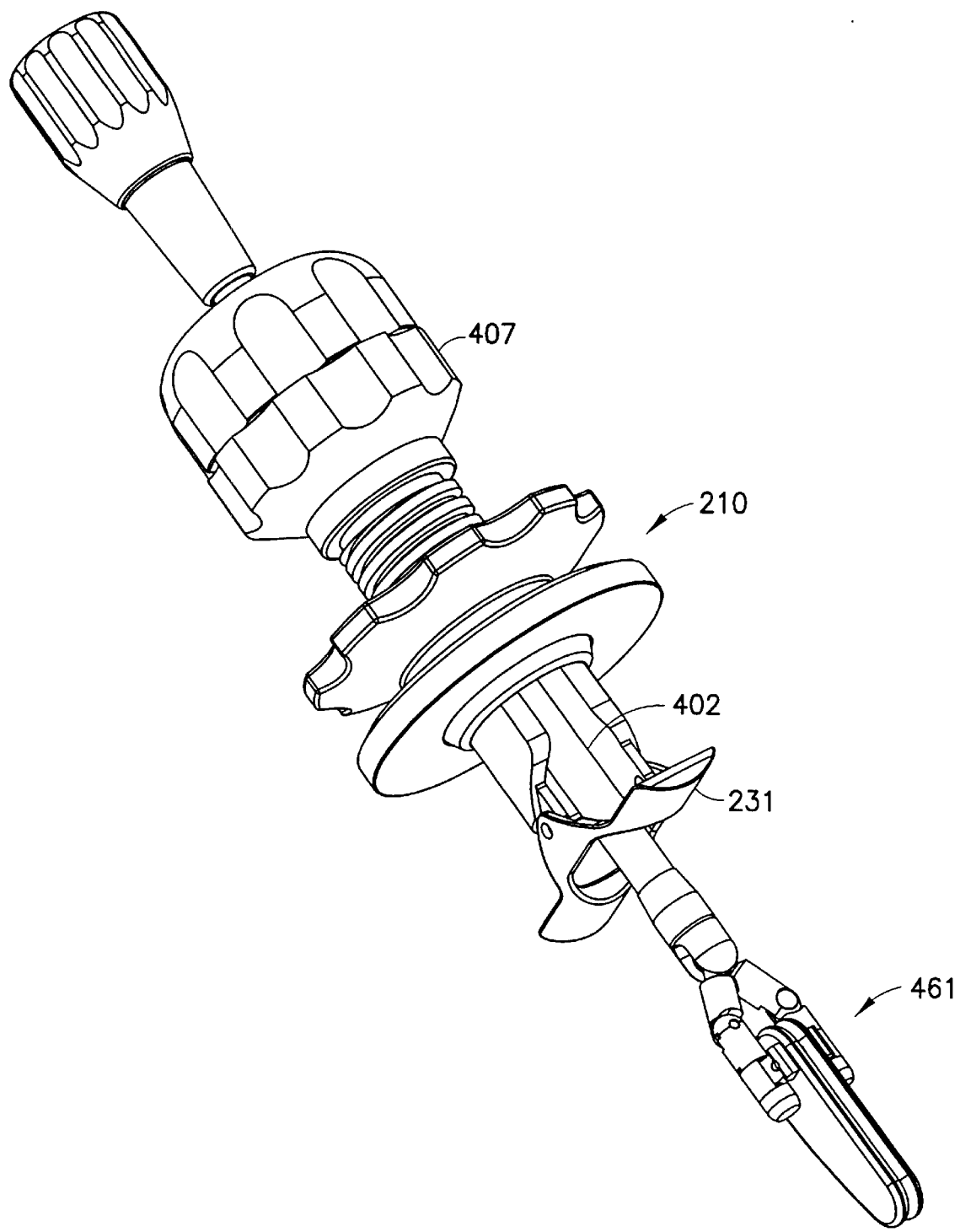
FIG. 24 is a perspective view of the heart stabilizer device, with the stabilizing assembly shown in a folded configuration and being extended through the port device of the invention.

The stabilizing assembly 461 is inserted into a port 210 (FIG. 22) which is mounted in a chest wall of a patient's body (not shown). The shaft lock 407, loosely provided about the shaft 402, is slid along the shaft 402 toward the port, and the port connector 408a of the shaft lock is then coupled to the port (FIG. 23). The shaft 402 is then moved through the shaft lock 407 until the stabilizing assembly 461 is moved beyond the swivel 231 of the port 210 to a location within the chest cavity permitting expansion of the stabilizing assembly 461 (FIG. 24). The shaft lock 407 is then tightened to retain the shaft 402 at the selected location relative to the port 210.

Figure 25:
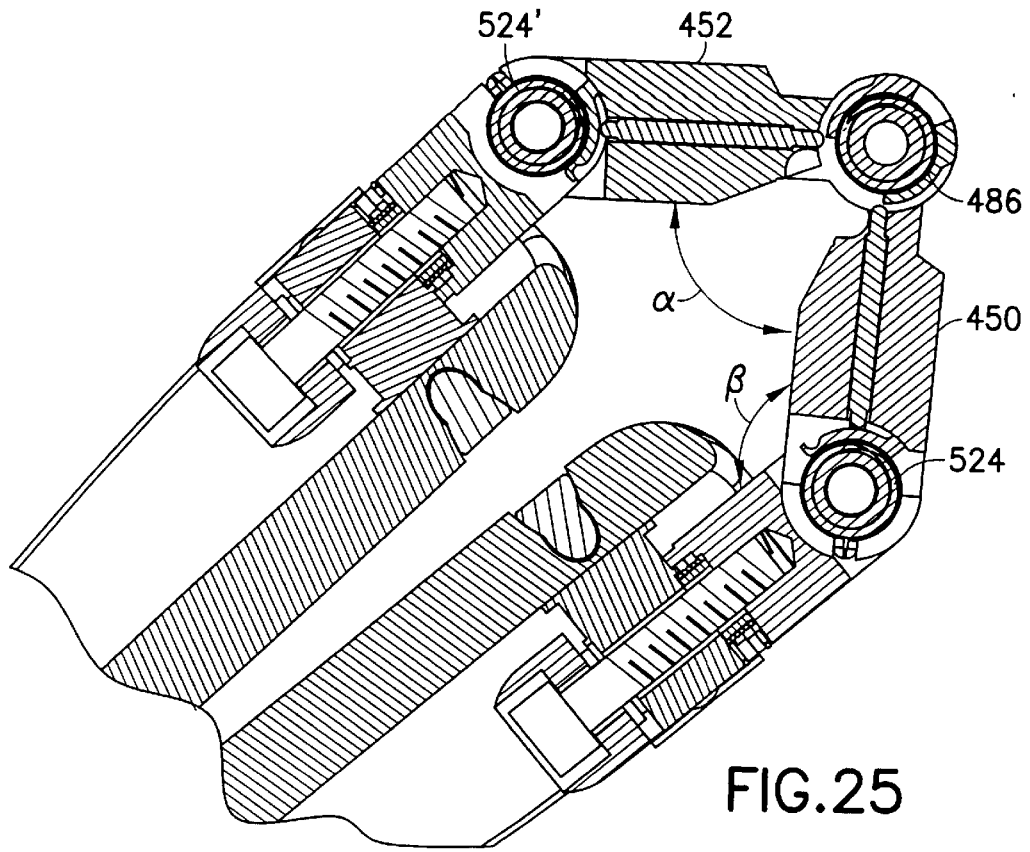
FIG. 25 is a partial longitudinal section view of the stabilizing assembly in a partially open first configuration.
Figure 26:
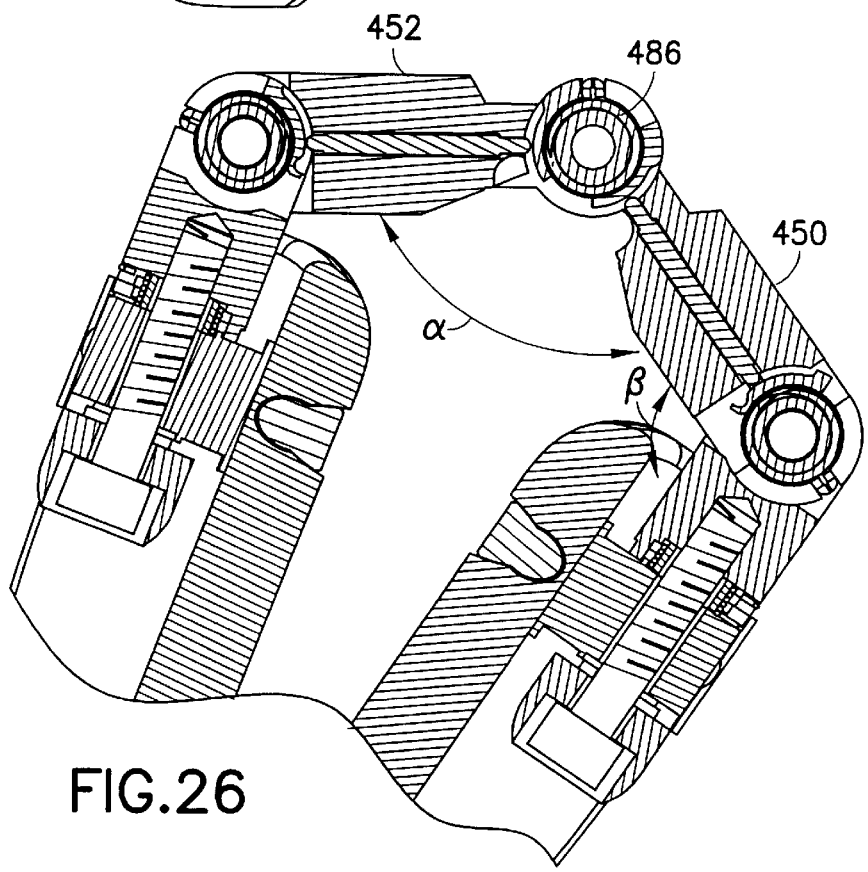
FIG. 26 is a partial longitudinal section view of the stabilizing assembly in a partially open second configuration more open that the first configuration.
Figure 27:
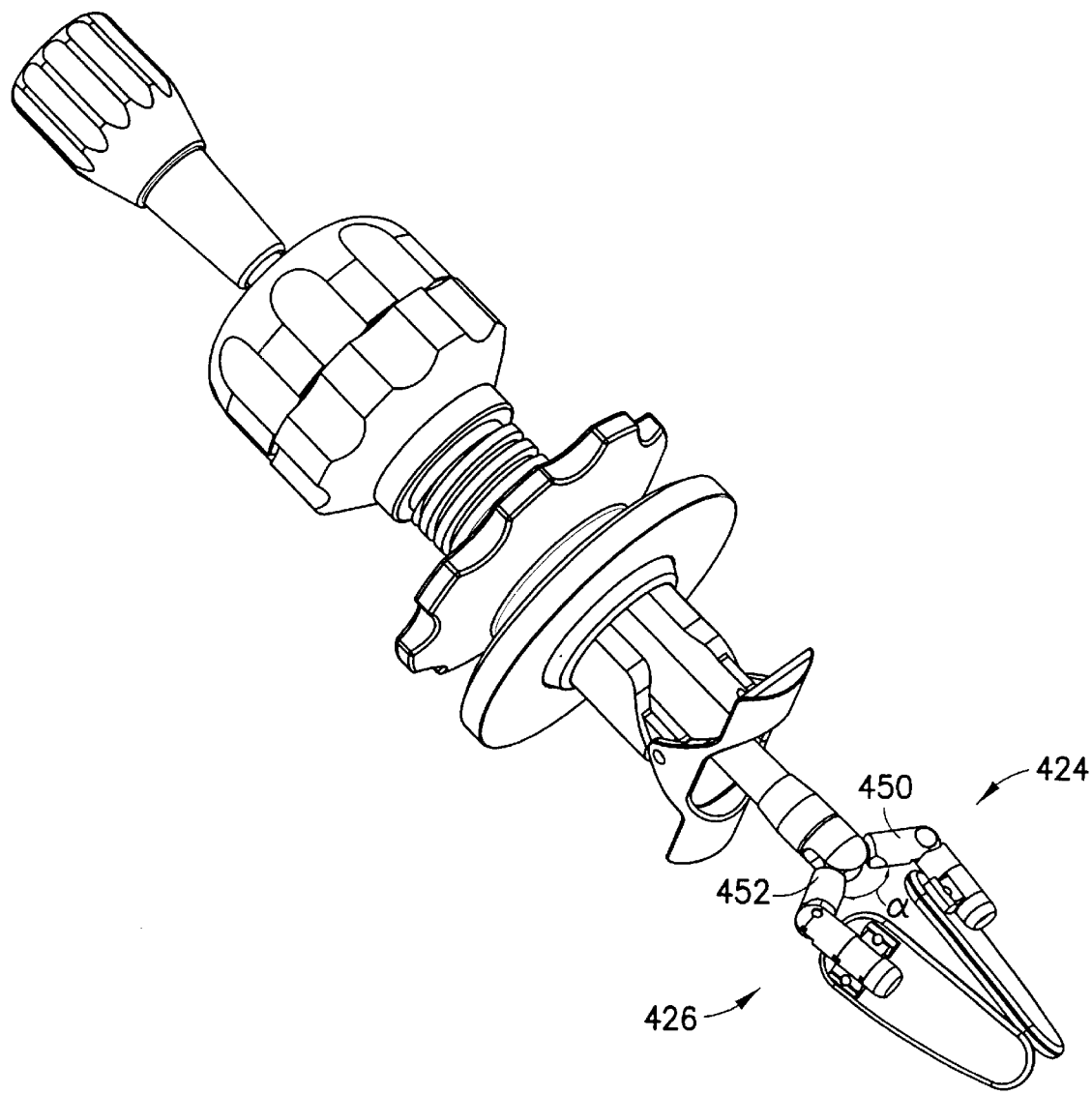
FIG. 27 is a perspective view of the heart stabilizer device, with the stabilizing assembly shown extended through the port device of the invention and in the second configuration.
Figure 28:
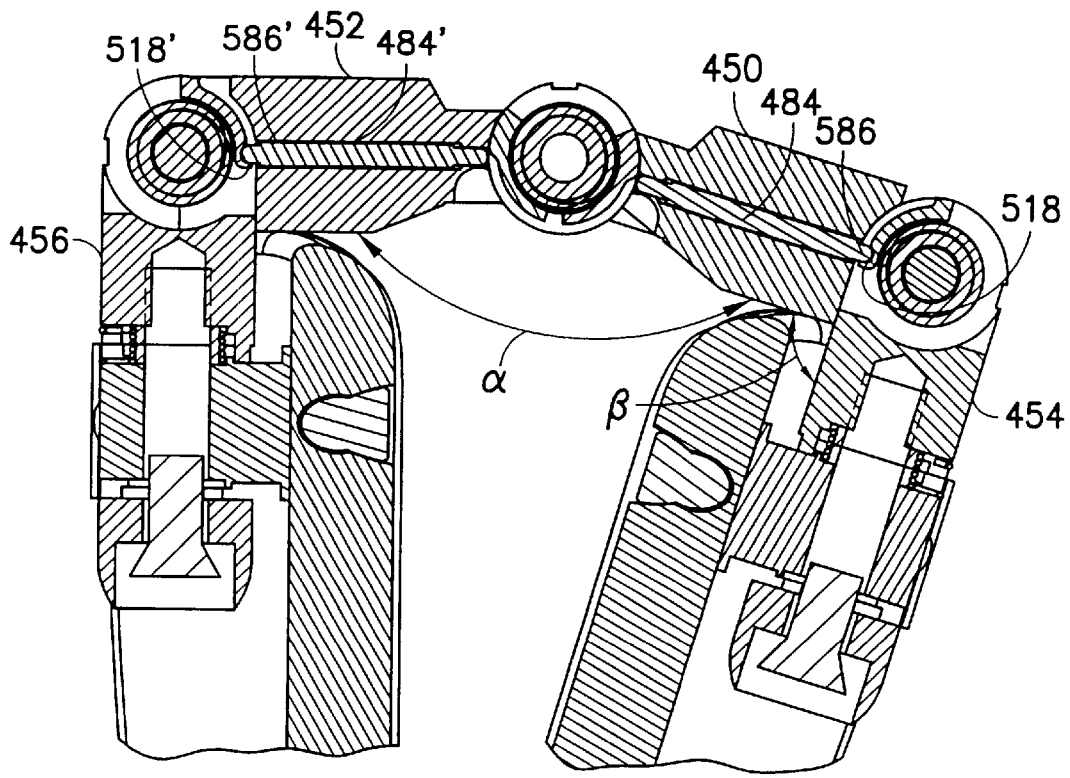
FIG. 28 is a partial longitudinal section view of the stabilizing assembly in a third configuration more open that the second configuration and in which the lock pins engage the lower arm cam locks.
Figure 29:
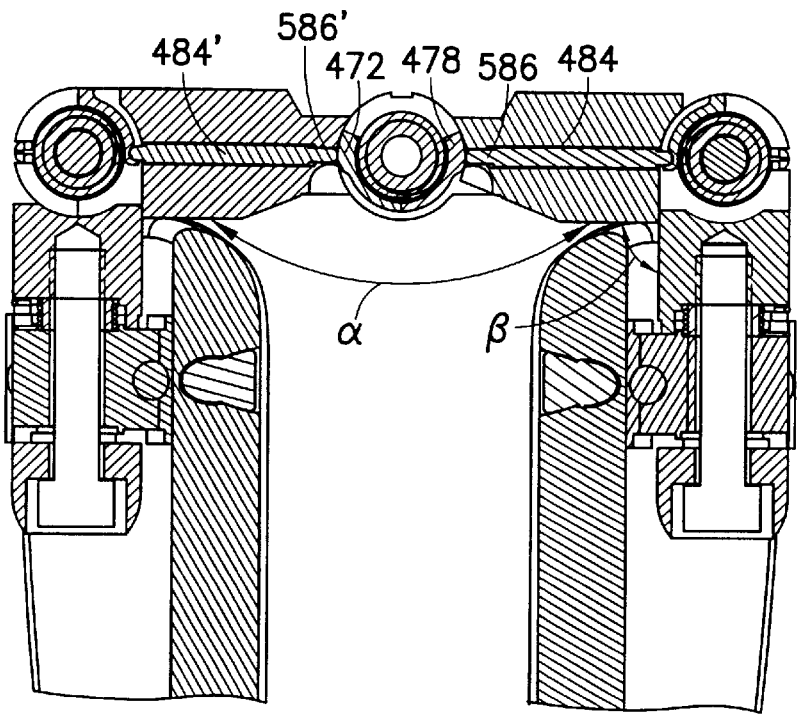
FIG. 29 is a partial longitudinal section view of the stabilizing assembly in a fully open fourth configuration in which the lower arms are locked relative to the upper arms.
Figure 30:
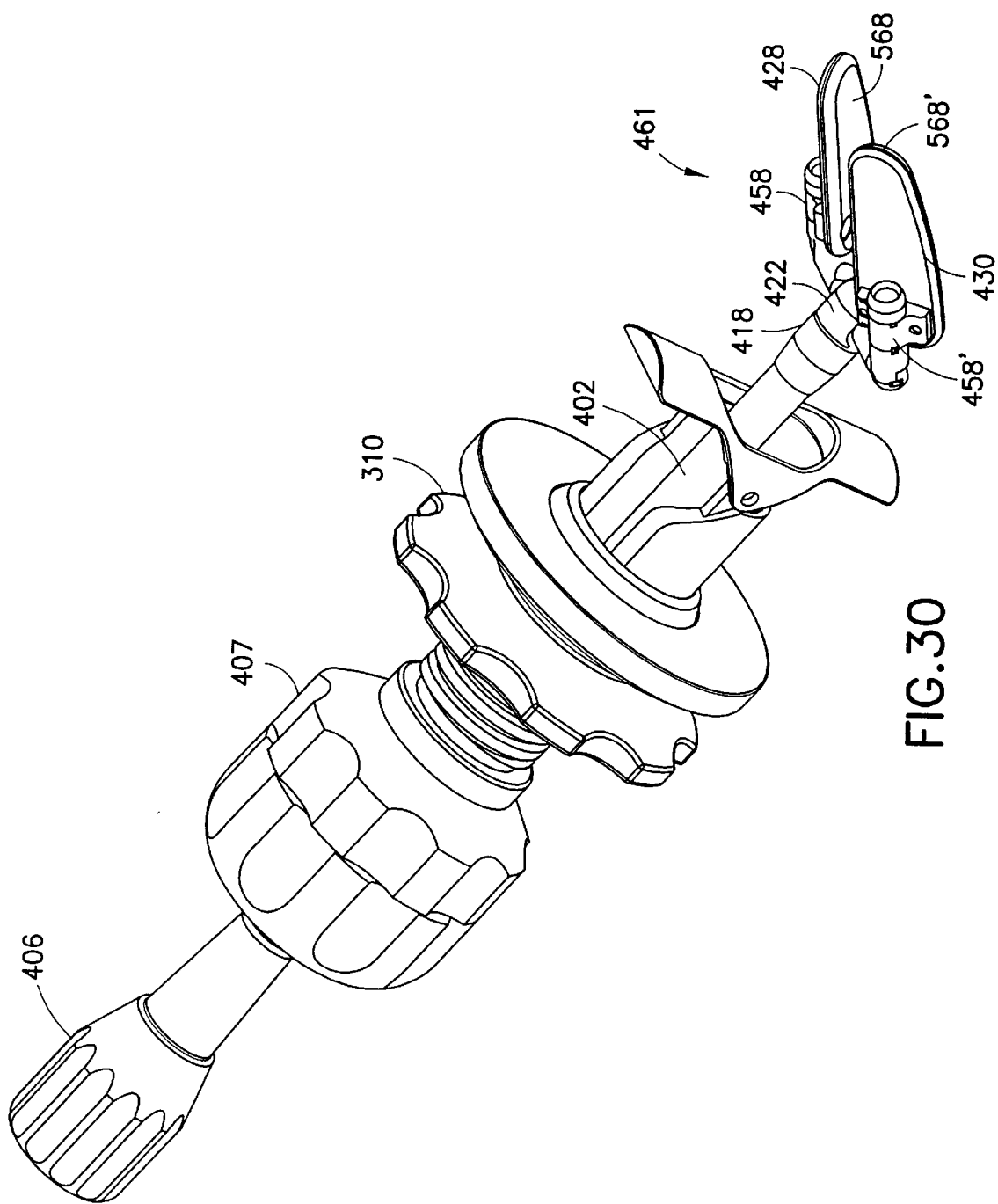
FIG. 30 is a perspective view of the heart stabilizer device, with the stabilizing assembly shown extended through the port device of the invention and in the fully open fourth configuration.

The knob 407 of the handle 406 is then operated to release the socket 422 from compression by the collar 418, thereby permitting movement of the articulating arms 424, 426 in accord with the forces of the springs and lock pins in the arms. More particularly, referring to FIGS. 20 and 25 through 27, when the socket is released, shoulder spring 487 operates to move the upper arms 450, 452 from a closed position ($\alpha$ equals approximately 47° in FIG. 20) toward a more open position ($\alpha$ equals approximately 87° in FIG. 25, and $\alpha$ equals approximately 126° in FIG. 26 and 27). In addition, elbow springs 524, 524' operate to bend the lower arms 454, 456 relative to the upper arms 450, 452 toward a smaller relative angle $\beta$. In FIG. 20, $\beta$ is approximately 156°; in FIG. 25, $\beta$ is approximately 135°; and in FIG. 26, $\beta$ is approximately 111°. Referring to FIG. 28, when $\alpha$ is approximately 163°, $\beta$ is substantially 90°, and the distal ends 586, 586' of the lock pins 484, 484' in the upper arms 450, 452 engage the cam locks 518, 518' of the elbows 510, 510' of the lower arms 454, 456. Then, as shown in FIG. 29, when the angle $\alpha$ is substantially 180°, the lock pins 484, 484' are engaged by the cams 472, 478 on the upper arms to lock the upper and lower arms at an angle $\beta$ of 90°. It is noted that $\beta$ is dependent on $\beta$ only in that as a increases, so does $\beta$ as a result of the springs in the elbow joints. The only fixed relationship between $\beta$ and $\beta$ are when the arms are fully folded, or fully deployed. It will be appreciated that this above described deployment and arm locking is automatic after the socket 436 is released from the collar 418. After deployment, the handle 406 may be operated to cause the collar to again clamp on the socket to prevent any relative movement of the upper arms which may otherwise potentially destabilize the stabilizer assembly 461.

Once the upper and lower arms are locked relative to each other, the shaft 402 (FIG. 16) may be unlocked from the shaft lock 407 and longitudinally moved such that the contact surfaces 568, 568' of the feet 428, 430 contact the heart wall. The feet are adapted to rotate at the wrist mounts 458, 460 relative to the lower arms to contour to the heart wall. The stops 546 on the lower arms (FIG. 19) preferably limit rotation of the feet to ninety degrees relative to the orientation shown in FIG. 21. The shaft 402 is again locked within the shaft lock such that the feet apply sufficient pressure against the wall of the heart to effectively immobilize motion of the heart wall between the feet such that the bypass procedure may be performed between the feet.

Furthermore, after the port off-pump coronary artery bypass procedure, when it is desired to withdraw the heart stabilizer through the port, the handle 406 may be operated to unlock the stabilizer assembly 461. The shaft of the stabilizer is then released from the shaft lock and/or the port connector of the shaft lock is released from the port, and then the stabilizer assembly is forced proximally. When the upper arms contact the port, the upper arms are forced to fold in a reverse operation to deployment, i.e., to a smaller angle $\alpha$, and release the lock pins from the cams and cam locks. As the upper arms fold about the shoulder, the contact surfaces of the feet contact each other and rotate such that the contact surfaces are substantially coplanar. This, in turn, causes the lower arms to rotate about the elbow such that an increased angle $\beta$ is provided between the upper and lower arms permitting withdrawal of the assembly through the port.

Figure 77:
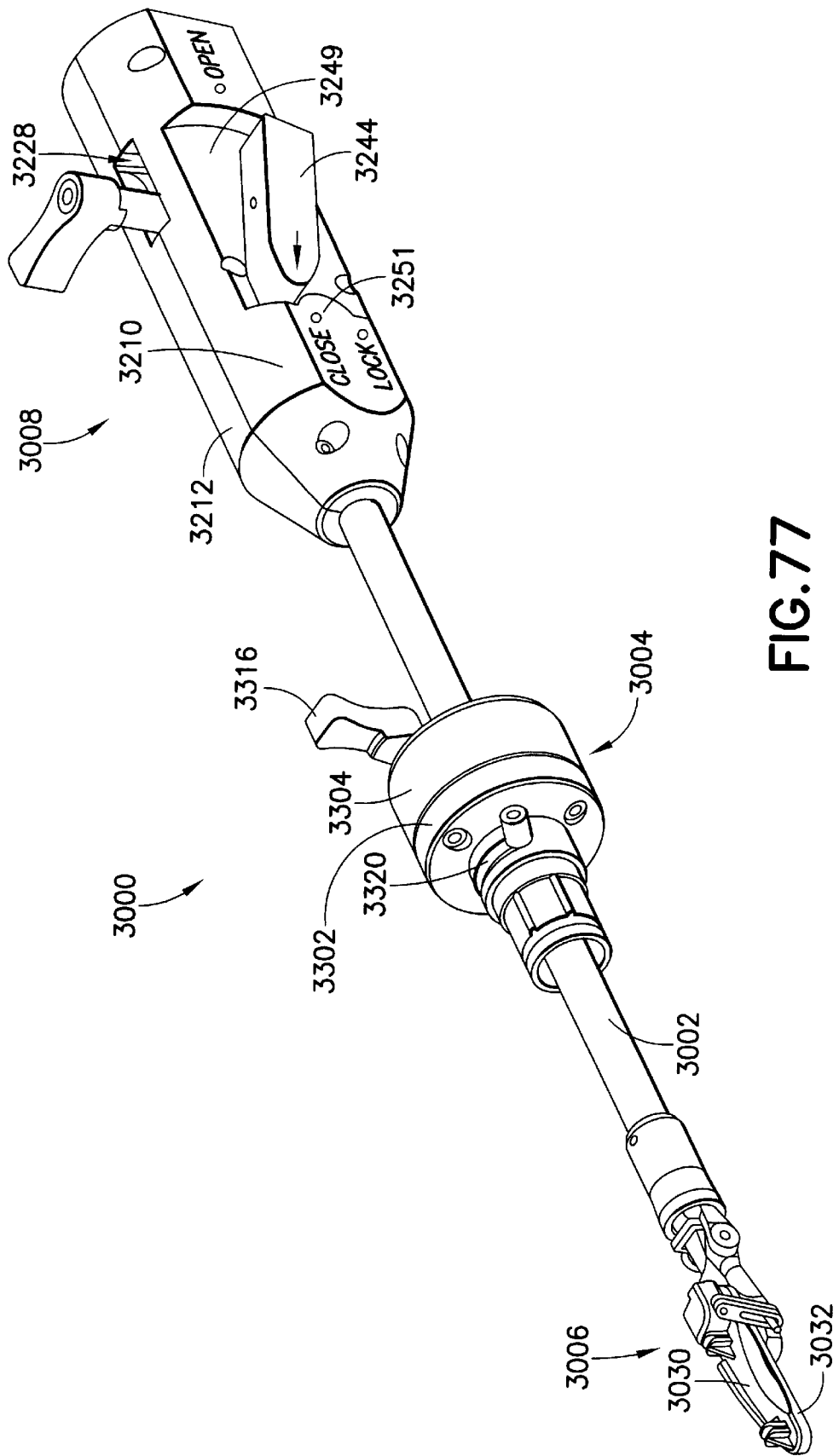
FIG. 77 is a perspective view of a second embodiment of a heart stabilizer shown in a closed configuration according to the invention.

Turning now to FIG. 77, another embodiment of the heart stabilizer 3000 is shown. The heart stabilizer 3000 includes a shaft 3002 provided with a shaft lock 3004 for coupling the heart stabilizer to a port assembly, e.g., port device 2100 (FIGS. 59 and 60) and adjusting the heart stabilizer relative thereto, a heart-contacting stabilizing assembly 3006 at the distal end of the shaft 3002, and a proximal handle assembly 3008 for controlling the stabilizing assembly 3006.

Figure 82:
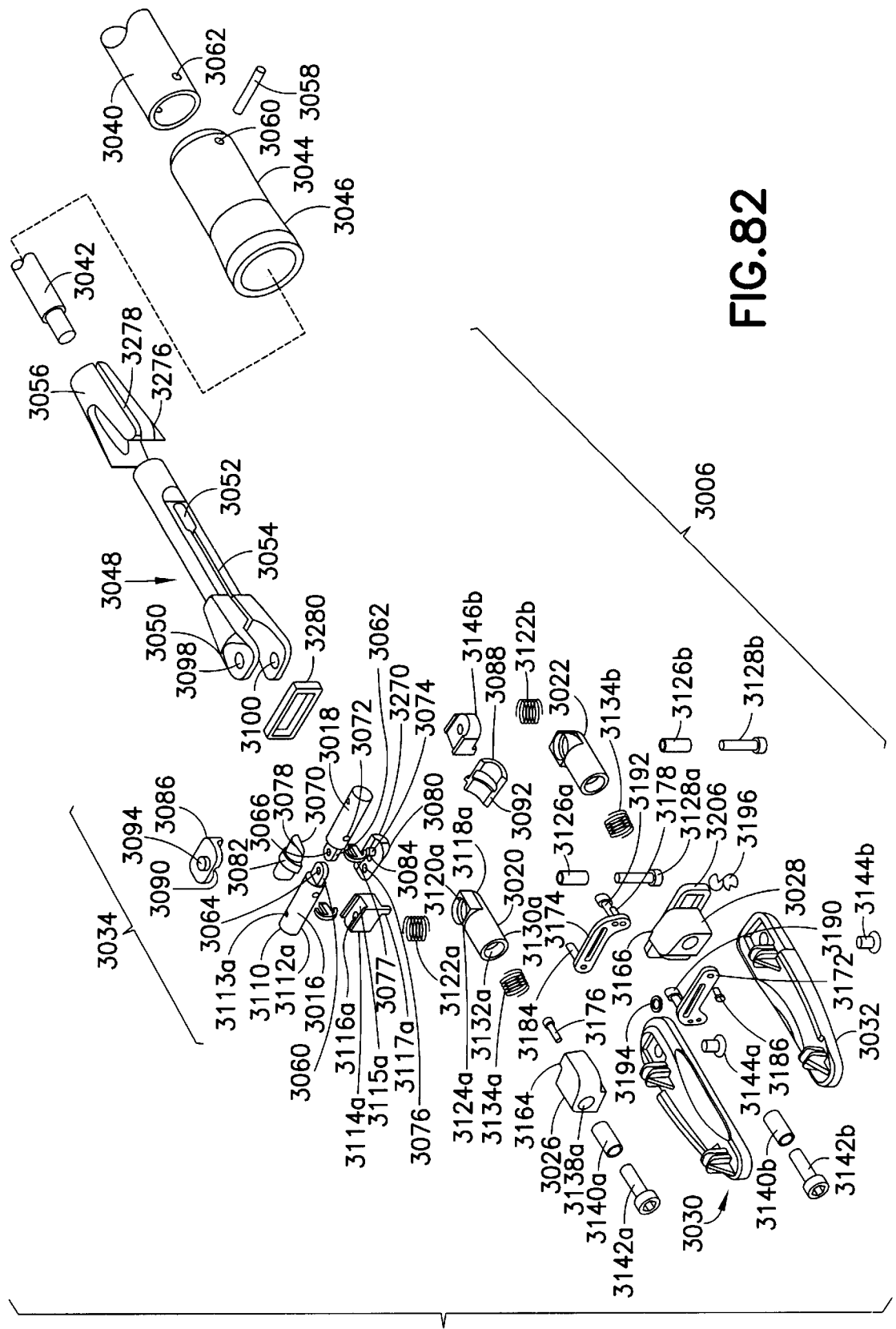
FIG. 82 is an exploded perspective view of the distal end of the heart stabilizer of the second embodiment of the invention.

Referring to FIGS. 78 through 82, the stabilizing assembly 3006 includes two arm assemblies 3012, 3014 movable between a closed position (FIG. 77) and an open position (FIGS. 78 through 81). Each arm assembly generally includes an upper arm 3016, 3018 and a lower arm 3020, 3022 articulating relative to each other, a rotational wrist mount 3026, 3028 at the distal end of the lower arm, and a foot 3030, 3032 stably coupled to the wrist mount. As described further below, the upper arms 3016, 3018 are articulable at an upper shoulder joint assembly 3034 at the distal end of the shaft 3002. Referring to FIGS. 82 and 83, the shaft 3002 includes an outer tubular member 3040 and a drawbar 3042 movable relative to the outer member. A collet closer 3044 having a flared opening 3046 is provided over the distal end of the outer member 3040, while a post 3048 having a clevis 3050 (and defining a collet) is coupled to the distal end of the drawbar 3042. The post 3048 also includes a slot 3052 and a bifurcation 3054 which extends from the slot 3052 to the clevis 3050 about which the post may be compressed. A collet cable guide 3056, discussed further below, extends over the post 3048 between the clevis 3050 and the slot 3052. A pin 3058 is provided through holes 3060 in the collet and holes 3062 in the outer tubular member (to thereby couple the collet closer 3044 to the end of the tubular member) and also through the slot 3052 in the post 3048. Movement of the drawbar 3042 within the tubular member 3040 is limited by the permitted movement of the slot 3052 over the pin 3058.

Referring to FIG. 82, the shoulder joint assembly 3034 at which the upper arms articulate is assembled as follows. The upper arms 3016, 3018 of arms 3012, 3014 each includes a proximal flange 3060, 3062 having a hole 3064, 3066. The flanges 3060, 3062 are positioned between upper and lower hinge elements 3070, 3072. The hinge elements 3070, 3072 each have a post 3074 which extends through one of the holes 3064, 3066 of the flanges and into a hole 3076 on the other of the hinge elements, and a rear wall 3077 such that the upper arms are rotatable between the hinge elements forward of the rear wall. The hinge elements 3070, 3072 each have an outer surface portion 3078, 3080 defined by radii about a line, and a protruding track 3082, 3084 along the surface portion 3078, 3080. The hinge elements 3070, 3072 are surrounded on the top and bottom by rotational guide elements 3086, 3088 which each include an inner radial channel 3090, 3092 through which the tracks 3082, 3084 of the hinge elements 3070, 3072 can be moved. The guide elements 3086, 3088 also include upper and lower post portions 3094 which extend into mounting holes 3098, 3100 in the clevis 3050. As such, the upper arms 3016, 3018 can be rotated from a proximal orientation in which the upper arms are substantially transverse to the shaft 3002 to a relatively distal orientation relative to the hinge elements 3070, 3072. The hinge elements can be rotated through the channels 3090, 3092 of the guide elements 3086, 3088 in the plane of the shaft (preferably by more than 180°); i.e., back movement (e.g., dorsiflexion) and forward movement (e.g., plantar flexion), and the guide elements can be rotated left to right in the clevis 3050. The arms 3012, 3014 of the stabilizing assembly 3006 are thereby provided with an extremely high degree of maneuverability relative to the shaft 3002.

It should be appreciated from FIGS. 78 through 82, that the arms 3012, 3014 are substantially similar except that they are provided in a mirrored configuration. As such, each element of one arm has a corresponding element on the other arm. Thus, for purposes of clarity, arm 3012 will now be described in greater detail with reference numerals relating thereto having an 'a' at the end of the numeral, with the understanding that arm 3014 has like elements with parts indicated with a 'b' at the end of the numeral.

The outer end 3110 of upper arm 3016 includes a lower flat portion 3112a and a hole 3113a extending therethrough. An offset 3114a includes a channel 3115a in which the flat portion 3112a of the upper arm 3016 is seated, a hole 3116a, and a stop 3117a. The upper end 3118a of the lower arm 3020 includes an elbow socket 3120a in which a first coil spring 3122a is provided, and a hole 3124a. A screw shoulder 3126a is inserted through hole 3124a and into the center of the first coil spring 3122a, and a screw 3128a is inserted through the shoulder 3126a, through hole 3116a, and thread into hole 3113a. The offset 3114a operates to lower the pivot point of the lower arm 3020 relative to the upper arm 3016, while ends of the first coil spring 3122a are coupled to the offset 3114a and lower arm 3020 to urge the upper and lower arms to pivot relative to each other into an obtusely-angled configuration. The stop 3117a limits the amount by which the upper and lower arms can relatively pivot.

The lower end 3130a of the lower arm 3020 includes a wrist spring socket 3132a in which a second coil spring 3134a is provided, and a screw hole (not shown) extending further into the lower arm 3020. The wrist mount 3026 includes a socket portion (not shown) and a hole 3138a extending through the socket portion. A screw shoulder 3140a extends through the hole 3138a and the second spring 3134a, and a screw 3142a then extends through the shoulder 3140a and is thread within the screw hole at the lower end 3130a of the lower arm 3020 to rotatably couple the wrist mount 3026 to the lower arm 3020.

Referring to FIGS. 78 through 80 and 82, the foot 3030 is stably mounted to a lower portion of the wrist mount 3026 with a screw 3144a such that rotation of the wrist mount relative to the lower arm 3020 rotates the foot by the same relative degree. The foot 3030 has an upper surface 3146a and a lower sole 3148a. The upper surface 3146a includes proximal and distal holds 3150a, 3152a for vessel loops or other material (e.g., suture) used in a surgical procedure on the heart. The lateral side of the foot 3030 includes an upstanding stiffening rib 3154a to increase foot rigidity and stability, and the medial side of the foot is provided with a scalloped contour 3156a to increase angular clearance between the two feet 3030, 3032. The sole 3148a of the foot is provided with a plurality of alternating short spikes 3158a and holes 3160a (FIG. 86). The spikes 3158a and holes 3160a are arranged such that when the stabilizing assembly 3006 is in a closed position, with the soles 3148 of the two feet 3030, 3032 positioned together (FIG. 77), the spikes 3158a of one foot enter the holes 3160b on the other foot, and vice versa, such that the soles 3148a, 3148b of the feet are substantially flush.

Referring to FIGS. 78 through 82, when the upper arms 3016, 3018 are relaxed, the feet 3030, 3032 are urged into the closed position by the following mechanism. Each wrist mount 3026, 3028 includes a lever portion 3164, 3166 provided with a hole (not shown). A cross slide 3172, 3174 is rotatably coupled to each lever portion 3164, 3166 at the respective holes with wrist pins 3176, 3178. Each cross slide 3172, 3174 includes an elongate slot 3180, 3182 and a pin 3184, 3186. The pin 3184 of a first cross slide 3172 is slidably movable within the slot 3182 of the second cross slide 3174, and the pin 3186 of the second cross slide is slidably movable within the slot 3180 of the first cross slide 3172. A lateral portion of each cross slide also is provided with a proximally extending post 3190, 3192 which carries a band hook 3194, 3196. A resilient band 3206 is stretched between the band hooks, and the band 3206 urges the wrist mounts 3026, 3028 toward each other.

The controlled movement of the stabilizing assembly 3006 into various configurations will be described after the following description of the proximal handle assembly 3008.

Turning now to FIGS. 77 and 83, the proximal handle assembly 3008 includes upper and lower handle pieces 3210, 3212 which together define a shaft bore 3213 in which the proximal end of the shaft 3002 is seated, and a control cavity 3214 having a yoke portion 3215, a circular cam area 3216, and a pivot slot 3218 proximal the circular area. A transverse slot 3228 is provided in the handle pieces at the location of the pivot slot 3218, and tracks 3224, 3226 are provided at lateral portions of the slot 3228. In addition, cable guide pathways 3220, 3222 are defined at the lateral sides of the control cavity 3214 and extend between the shaft bore 3213 and the tracks 3224, 3226.

Figure 84:
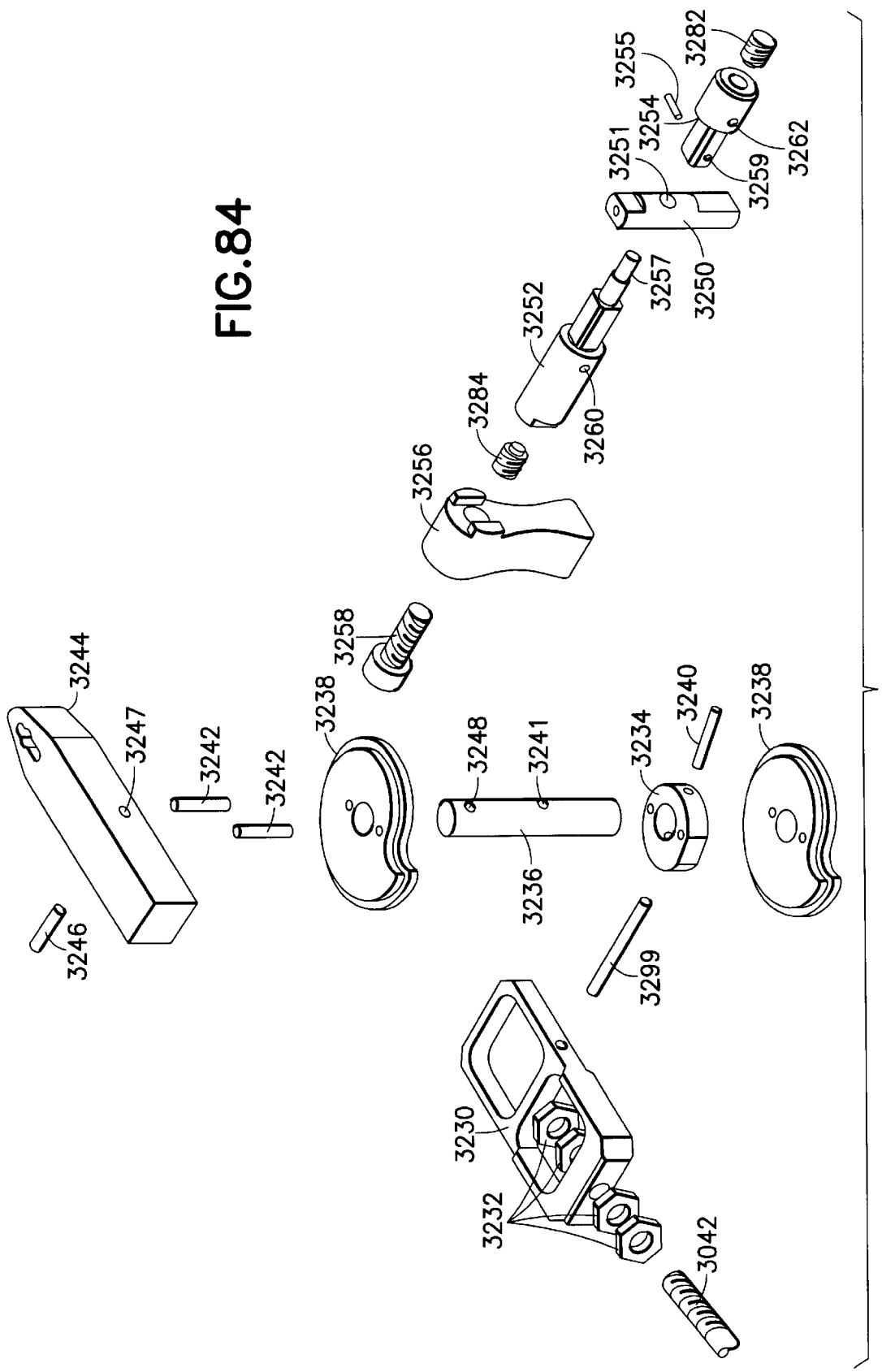
FIG. 84 is an exploded perspective view of the control and actuation assemblies of the heart stabilizer of the second embodiment of the invention.

Referring to FIGS. 83 and 84, within the cavity 3214, an actuation assembly and a control assembly are provided. The actuation assembly includes a yoke 3230 generally having a frame in the shape of a 'FIG. 8'. The proximal end of the drawbar 3042 extends into a distal portion of the yoke 3230 and a plurality of fasteners 3232 stably couple the drawbar to the yoke. An inner cam 3234 is provided within the rear portion of the yoke 3230. A cam axle 3236 extends through the inner cam, and outer cams 3238 are provided above and below the inner cam outside the yoke 3230. The inner cam 3234 is rotatably fixed to the cam axle 3236 with a dowel pin 3240, and the outer cams 3238 are rotatably fixed to the inner cam 3234 with additional pins 3242. A lever 3244 is fixedly coupled to a portion of the cam axle 3236 extending outside the upper handle 3210 (e.g., with a pin 3246 extending through holes 3247, 3248 in the lever 3244 and the cam axle 3236, respectively). Referring to FIG. 77, the upper handle 3210 includes a lever channel 3249 in which the lever 3244 can be rotated with the cam axle 3236. The lever channel 3249 indicates three positions at which the lever 3244 can be located ('closed', 'open', and 'locked', although the lever can be located at other intermediate positions), and defines a stop 3251 for the 'closed' and 'locked' positions.

Figure 78:
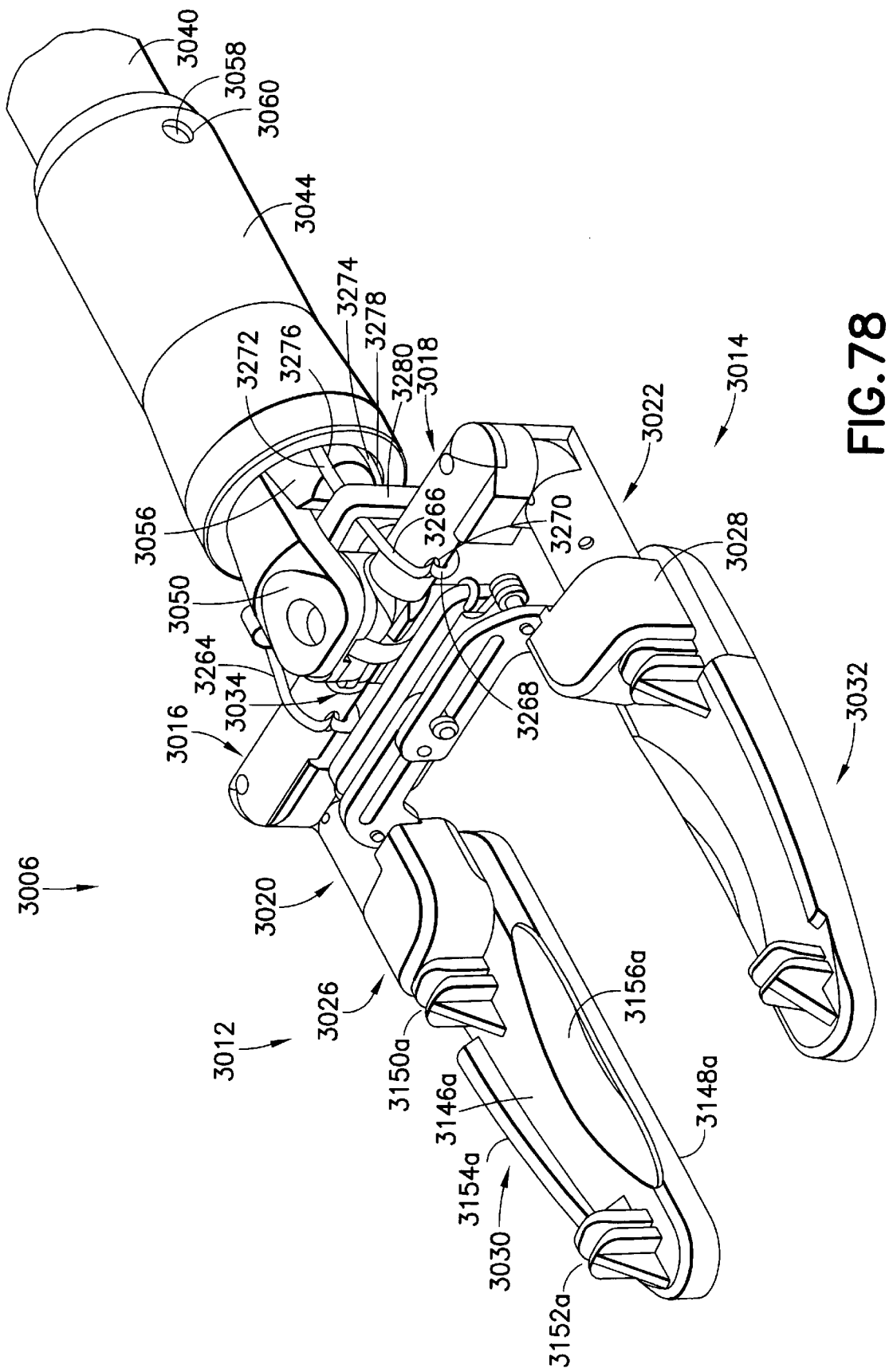
FIG. 78 is an enlarged perspective view of the distal end of the heart stabilizer of the second embodiment of the invention.
Figure 79:
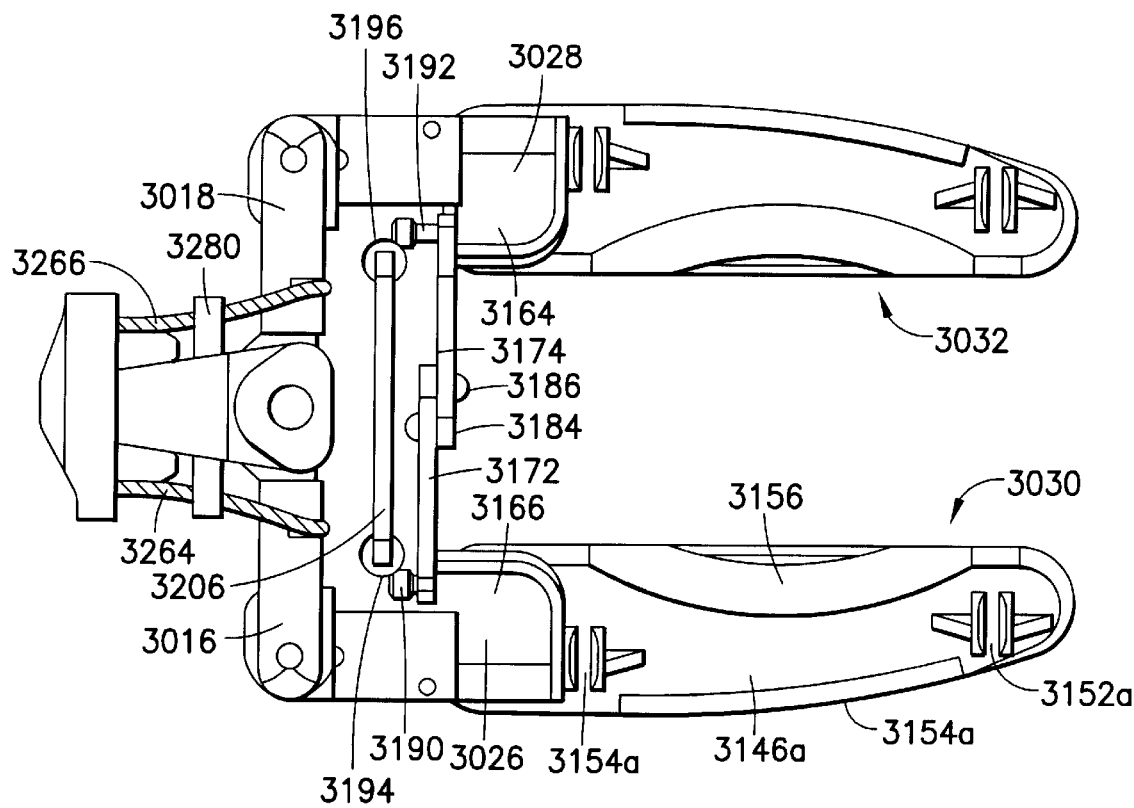
FIG. 79 is an enlarged top view of the distal end of the heart stabilizer of the second embodiment of the invention.
Figure 80:
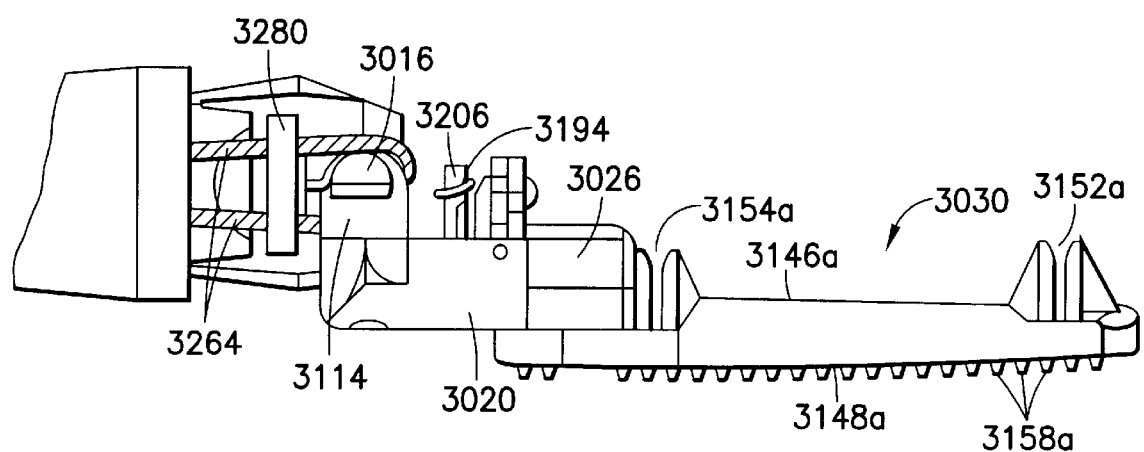
FIG. 80 is an enlarged side elevation view of the distal end of the heart stabilizer of the second embodiment of the invention.

Referring back to FIGS. 83 and 84, the control assembly includes a joystick axle 3250 rotatable within the pivot slot 3218, male and female crossbar members 3252, 3254 rotatably coupled to the joystick axle 3250, and a joystick 3256 coupled to the male crossbar member 3252, preferably with a screw 3258. The male crossbar member 3252 extends through a hole 3251 in the joystick axle 3250 and the female member 3254 is provided over the end of the male member; a dowel pin 3255 positioned through pin holes 3257, 3259 secures the crossbar members 3252, 3254 together. Each of the male and female crossbar members 3252, 3254 includes a preferably diametric cable hole 3260, 3262. Two cables 3264, 3266 operate to translate movement of the joystick 3256 into movement of the stabilizing assembly. As seen in FIG. 78, for each cable, e.g., cable 3266, a loop portion 3268 is coupled through a hole 3270 in an upper arm 3018 of the stabilizing assembly 3006. Cable portions 3272, 3274 extend from the loop 3268 about upper and lower portions of the respective upper arm 3018 (FIG. 78), through respective guide slots 3276, 3278 in the collet cable guide 3056 (FIG. 82), through the tubular member 3040, and into the respective cable pathway 3222 (FIG. 83). Just proximal the upper arms 3016, 3018 and distal of the collet cable guide 3056, an elastic band 3280 is provided about the cables 3264, 3266 for cable management (FIGS. 78 through 80). In addition, a handle cable guide 3281 (FIG. 83) is provided between the upper and lower handle pieces 3210, 3212 and about the control cavity 3214 to guide the cables 3264, 3266 from the tubular member 3040 to the cable pathways 3220, 3222. The ends of cable 3266 extend about upper and lower portions of the female crossbar 3254 and are locked within the cable hole 3262 of the crossbar, preferably with a set screw 3282, while the ends of cable 3264 extend about upper and lower portions of the male crossbar 3252 and are locked within the cable hole 3260 of the crossbar with another set screw 3284.

The heart stabilizer 3000 is operated as follows. When the lever 3244 is oriented in the 'closed' position, as shown in FIGS. 77 and 83, the inner and outer cams 3234, 3238 are substantially inactive, such that the control member 3042 and cables 3264, 3266 are in a relaxed state. As such, the stabilizing assembly 3006 is permitted to move in accord with the biases of the coil springs 3122a, 3122b and 3134a, 3134b and the resilient band 3206 in the stabilizing assembly. First coil springs 3122a, 3122b urge the lower arms 3020, 3022 to rotate into an oblique angle relative to the upper arms 3016, 3018 so that the arms are forced into an outstretched configuration, and second coil springs 3134a, 3134b urge the wrist mounts 3026, 3028 to rotate into an orientation in which the soles 3148a, 3148b of the feet 3030, 3032 face each other. The resilient band 3206 pulls the wrist mounts 3026, 3028 together such that the soles of the feet contact one another. These forces cause the stabilizing assembly 3006 to assume a narrow profile suitable for insertion through a port, e.g., the tubular body of the above described port device.

Figure 85:
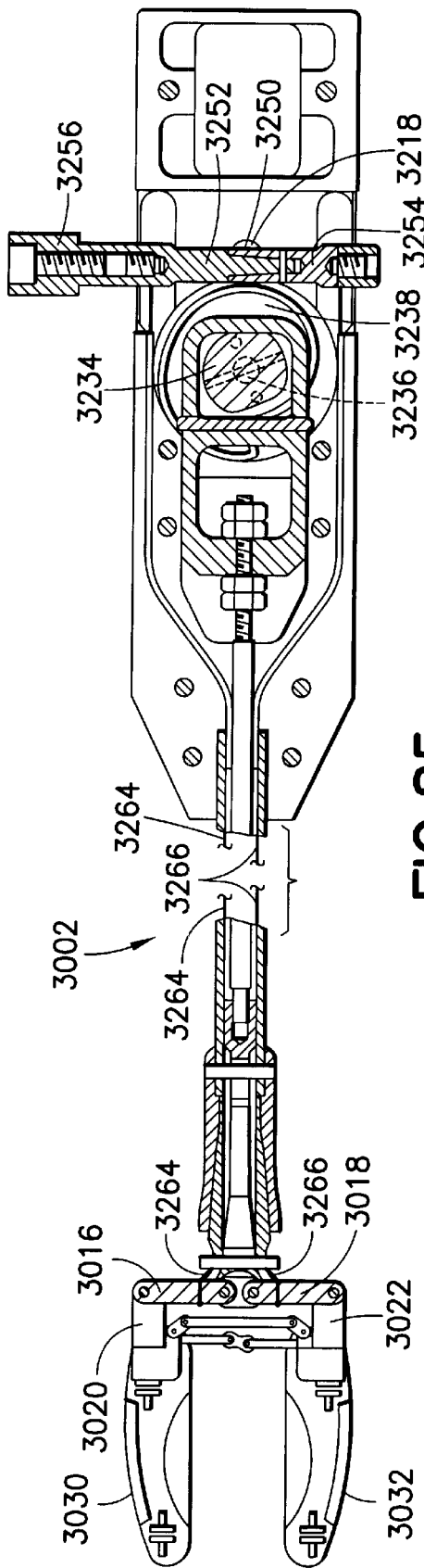
FIG. 85 is a longitudinal top section view of the heart stabilizer of the second embodiment of the invention, shown in an open configuration.

When the lever 3244 rotates on the cam axle 3236 into the 'open' position, as shown in FIGS. 85 (and by the position of the lever in FIG. 86), the outer cams 3238 are rotated to contact and move the joystick axle 3250 proximally within the pivot slot 3218, while the inner cam 3234 remains inactive (i.e., does not cam against a surface) in its new rotational position. Such proximal movement of the joystick axle 3250 causes the crossbars 3252, 3254 to move proximally and place tension on the cables 3264, 3266 sufficient to overcome the bias of the first coil springs 3122a, 3122b (FIG. 82) and cause the upper arms 3016, 3018 to rotate in the shoulder joint assembly 3034 (FIG. 78) and assume a substantially transverse orientation relative to the shaft 3002 (FIG. 85). The lower arms 3020, 3022 simultaneously rotate relative to the upper arms 3016, 3018 to extend substantially parallel to the shaft 3002, maintained in parallel alignment by the sliding interengagement of the slides 3172, 3174 and limited to a position substantially perpendicular to the upper arms by stops 3117a, 3117b (FIGS. 79 through 82 and 85). Referring to FIG. 81, when the arms 3012, 3014 are thusly deployed into the 'open' position, the soles 3148, 3148b of the feet 3030, 3032 are angled relative to each other as indicated by angle φ, which is preferably between 135° and 170°.

With the arms 3012, 3014 in the 'open' position, the joystick 3256 may be manipulated to steer the stabilizing assembly 3006 into a desired orientation relative to the shaft. Pivoting the crossbar (the assembly of crossbars 3252, 3254) on the joystick axle 3250 pulls one cable more than the other cable and functions to move the feet 3030, 3032 left and right relative to the shaft. For example, referring to FIG. 88, cable 3264 is pulled back further than cable 3266 causing the feet 3030, 3032 to be directed to the right of the shaft 3002. The extent by which the feet 3030, 3032 may be directed is infinitely adjustable between the proximal and distal throw of the crossbar through the transverse slot 3228 of the handle pieces 3310, 3312. Furthermore, rotation of the crossbar (members 3352, 3354) about its longitudinal axis causes one end of each cable to be pulled relative to the other end of the same cable such that the stabilizing assembly 3006 rotates between back (e.g., dorsiflexion) and forward (e.g., plantar flexion) positions. FIG. 86 illustrates a back 'dorsiflexion' position. Therefore, by both pivoting and rotating the joystick 3256, the feet 3030, 3032 may be steered into a desired orientation.

Figure 88:
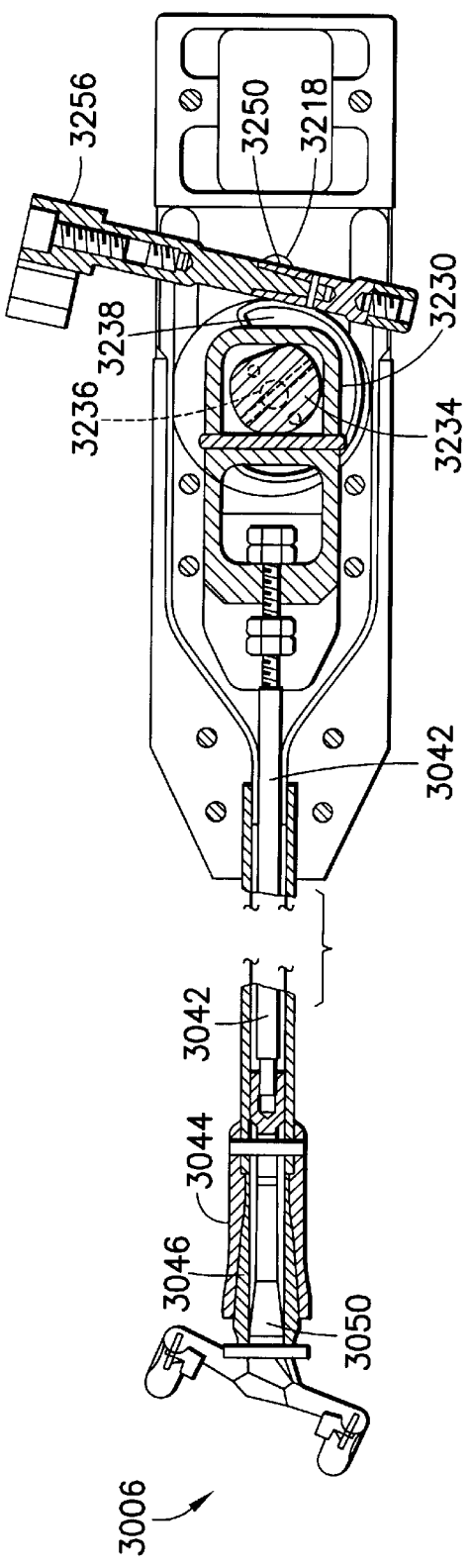
FIG. 88 is a longitudinal top section view of the heart stabilizer of the second embodiment of the invention, shown with the stabilizing assembly in a rotated position and in a locked configuration.

Referring to FIG. 87, once the desired orientation is attained, the lever 3244 is rotated in the channel into the 'locked' position against stop 3251. Referring to FIG. 88, in the 'locked' position, the cam axle 3236 is rotated such that the inner cam 3234 forces the yoke 3230 to move proximally which, in turn, causes the control member 3042 to pull the clevis 3050 into the flared end 3046 of the collet closer 3044 and thereby compress the clevis 3050 to immobilize the shoulder joint assembly 3034 (FIGS. 78, 82 and 88). A hardened dowel pin 3299 may be used provided for contact by the inner cam 3234 to prevent galling if a relatively softer yoke material is used. In addition, in the 'locked' position, the outer cams 3238 force the joystick axle 3250 back against the rear of the joystick pivot slot 3218 to substantially immobilize movement of the joystick 3256 and take up any slack in the cables 3264, 3266 created by proximal movement of the stabilizing assembly 3006 relative to the shaft 3002. As such, in the 'locked' position, the stabilizing assembly 3006 is stable and can be contacted against heart tissue to apply force sufficient to substantially immobilize heart tissue between the feet. It will be appreciated that the spikes 3158a, 3158b on the feet 3030, 3032 provide traction for the feet on the heart surface.

Referring now to FIGS. 77 and 89, a shaft lock 3004 is provided about the shaft 3002 to lock the heart stabilizer 3000 to one of the previously described port devices, and also permit adjustment of the heart stabilizer relative to the port device once the heart stabilizer is locked to the port device. The shaft lock 3004 includes a base 3302 and a cap 3304 together defining a socket 3306, and a slotted oblately spherical collet 3308 within the socket. The shaft 3002 of the heart stabilizer 3000 extends through the collet 3308 (FIG. 77). The base 3302 and cap 3304 are coupled together with screws 3310, 3312, 3314 such that the collet 3308 is not compressed within the socket 3306. One of the screws 3314 extends through the base 3302 and cap 3304, and is provided at its end with a locking lever 3316 having a cam surface 3318. When the lever 3316 is positioned such that the cam surface 3318 is not in a camming position (described below), the shaft 3002 is slidable through the collet 3308, and the collet is rotatable within the socket, e.g. ±5° relative to the longitudinal axis of the coupling assembly 3300. When the lever 3316 is rotated, the cam surface 3318 rides over the top of the cap 3304 into a camming position and forces the cap 3304 and base 3302 together to compress the collet 3308 and lock the shaft 3002 in its angular and longitudinal position relative to the base and cap.

The base 3302 also includes a distal end provided with a slit tubular portion 3320 and two helical peg slots 3322. A cam bushing 3324 is provided in the tubular portion 3320, and cam lever pegs 3326 extend into the peg slots 3322. The cam lever pegs 3326 are secured to the cam bushing 3324 with screws 3328 which enter holes 3330 in the cam bushing 3324. The cam bushing 3324 has a flared end 3332 which is positioned distally of the tubular portion 3320 when in an unlocked configuration.

In use, the stabilizing assembly 3006 of the heart stabilizer is passed into and through the tubular body of a port device, and the cam bushing 3324 and the tubular portion 3320 are inserted into the proximal end of the tubular body of the port device. The cam lever pegs 3326 are then manually rotated within the peg slots 3322 to cause the cam bushing 3324 to be withdrawn into the slit tubular portion 3320 and expand the slit tubular portion sufficiently to lock the shaft lock 3004 and, hence, the heart stabilizer 3000 to the port device.

According to various embodiments of the heart stabilizer, the feet of the stabilizer may be further adapted to facilitate immobilization of the heart wall between the feet. In addition to compressive forces, the feet may be adapted to apply suction, chemical agents, electrical current, or thermal cooling to enhance the heart wall immobilization.

In addition, while various means for opening, and limiting the extent of opening, of the stabilizing assemblies of the heart stabilizer have been disclosed, it will be appreciated that other means providing the same function may be used. Moreover, while particular preferred angles between the elements of the stabilizing assemblies have been disclosed, it will be appreciated that other preferred angles can be used, with angles other than those disclosed causing engagement of the cams to lock the arms.

Figure 37:
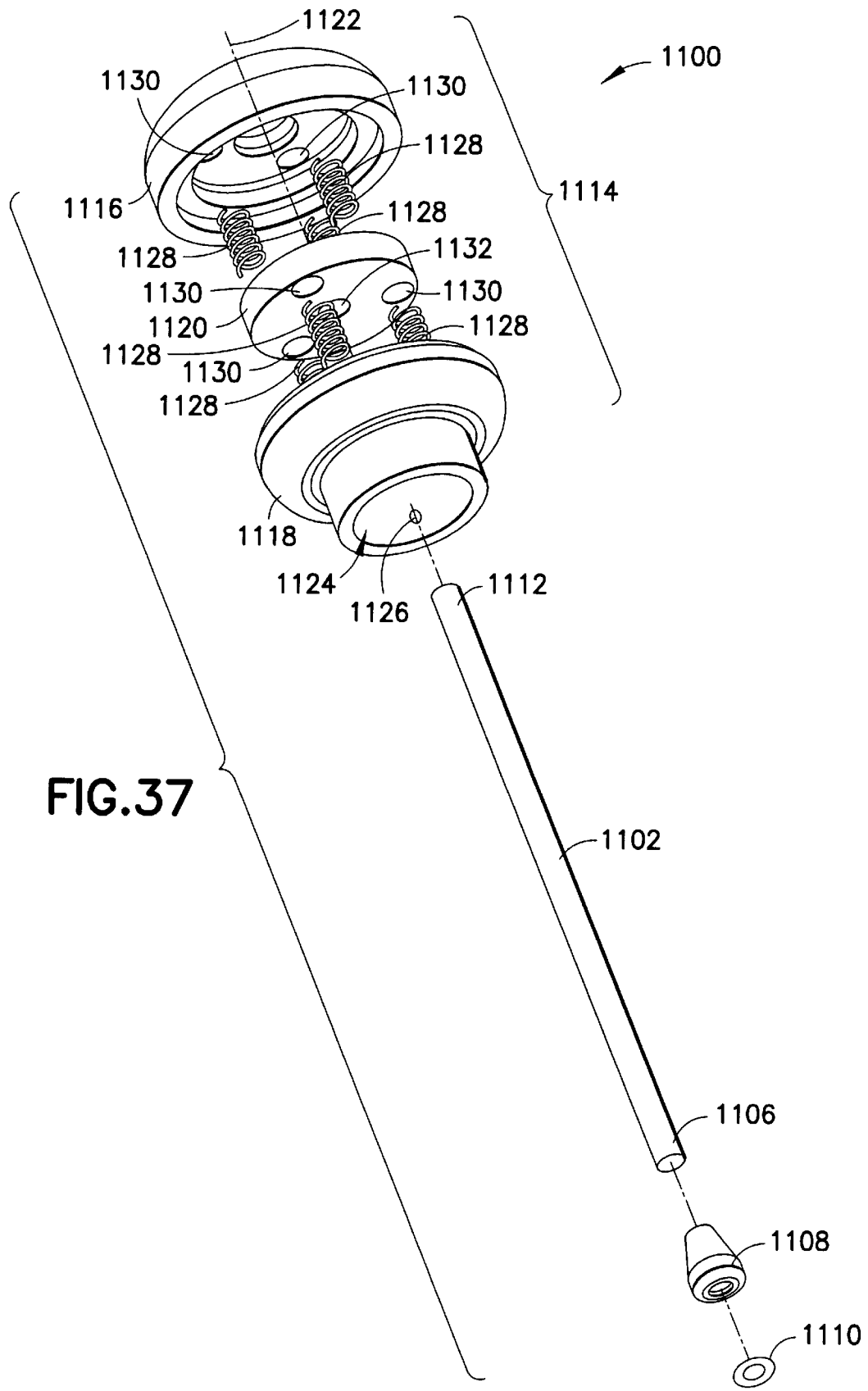
FIG. 37 is an exploded view of the first embodiment of the instrument stabilizer.

Referring now to FIGS. 35 through 37, a first embodiment of an instrument stabilizer 1100 is shown. The instrument stabilizer 1100 includes a cannula 1102 through which an endoscopic instrument, e.g, a laparoscopic instrument, can extend. Endoscopic instruments, in general, are instruments which are extendable through a scope, or operated in conjunction with a scope, used to view the inside of a body cavity. The distal end 1106 of the cannula 1102 is provided with a tapered ferrule 1108 including an O-ring 1110 adapted in size to contact an endoscopic instrument extending therethrough. The proximal end 1112 of the cannula 1102 is coupled to a proximal housing 1114 of the instrument stabilizer.

The proximal housing 1114 includes an upper shell 1116 and a lower shell 1118, and a disk 1120 stabilized therebetween. The upper shell 1116 includes a central opening 1122 through which an endoscopic instrument may extend. The lower shell includes a relatively larger central opening 1124, and optionally includes a mating structure, e.g., a nub 1126, adapted to couple the housing 1114 to a mating structure on one of the above described ports, or another port. The disk 1120 is preferably stabilized with preferably three equally-spaced springs 1128 provided on either side of the disk. To maintain the springs 1128 in their relative positions, each side of the disk and the corresponding interior surfaces of the upper and lower shells include recesses 1130 into which the ends of the springs are provided. The upper and lower shells 1116, 1118 are then coupled together about the disk 1120, e.g., via sonic welding, a threaded coupling, or a plurality of fasteners such as screws. The disk 1120 includes a central opening 1132 in which the proximal end 1112 of the cannula 1102 is fixed, e.g., by interference fit or gluing. Alternatively, the cannula 1102 may be snugly fit within the central opening 1132 and permitted to move longitudinally therein to adjust the extension of the distal end 1106 of the cannula relative to the housing 1114.

Figures 38, 39:
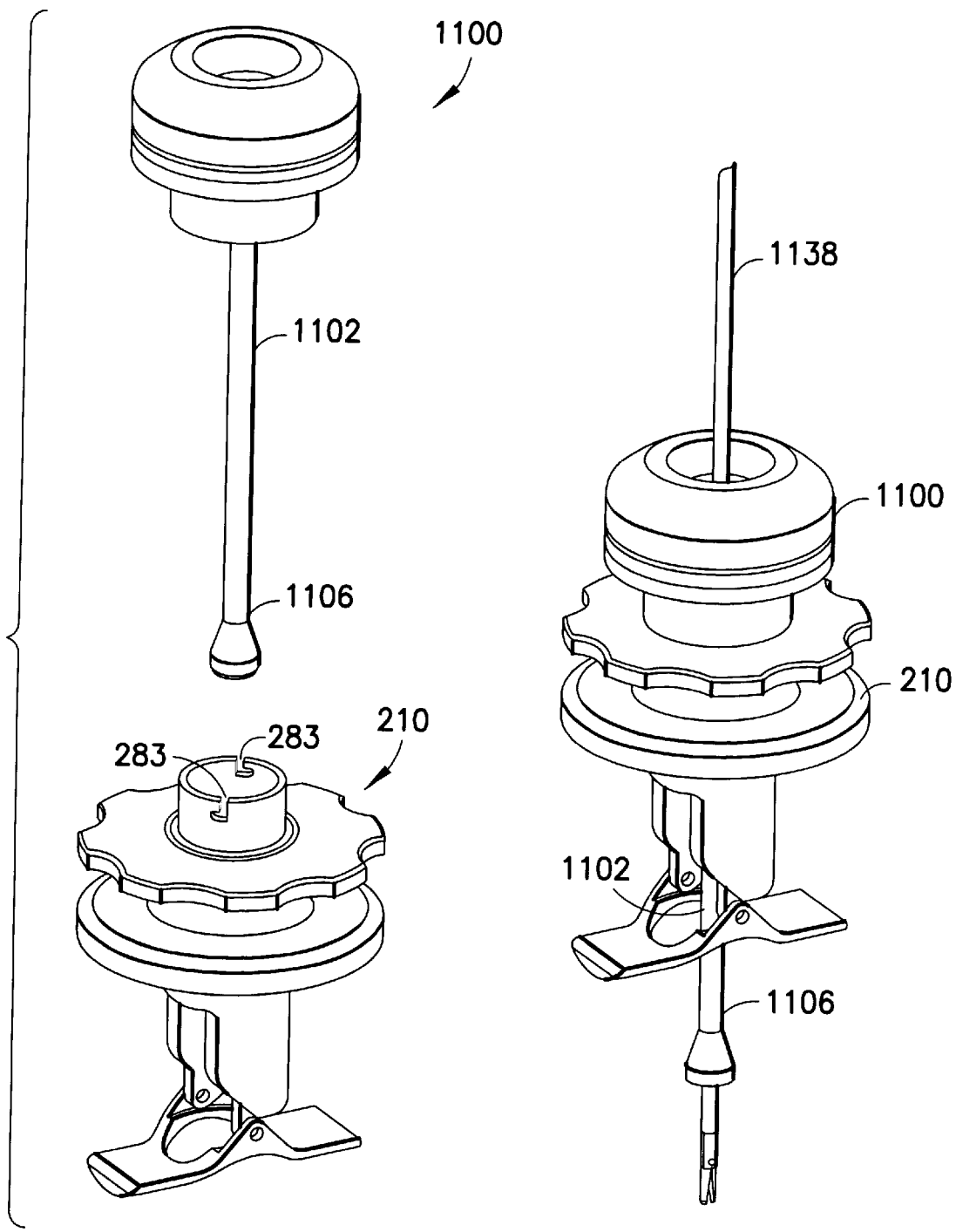
FIG. 38 is an exploded perspective view of the first embodiment of the instrument stabilizer aligned with a port device according to the invention.
FIG. 39 is a perspective view of the first embodiment of the instrument stabilizer coupled to a port device, and a surgical instrument extending through the instrument stabilizer and port device.

Turning now to FIGS. 38 and 39, the instrument stabilizer 1100 may be inserted through a port, e.g., port 210, provided in the body of a patient. The distal end 1106 of the cannula 1102 is extended through the port and the mating structure 1126 (FIG. 35) may then be coupled to the mating structure 283 on the port thereby rigidly fixing the instrument stabilizer and the port together (FIG. 39). An endoscopic instrument 1138 may then be inserted through the opening in the upper shell and through the cannula. As the endoscopic instrument 1138 exits the distal end of the cannula 1102, the instrument contacts the O-ring 1110 thereby creating an interference between the instrument and the O-ring such that a slight resistance to movement of the endoscopic instrument is provided. The spring-stabilized disk 1120, in conjunction with the body tissue, operates to stabilize lateral movement of the endoscopic instrument 1138, while the O-ring 1110 operates to stabilize longitudinal movement of the instrument 1138. As a result, slight forces, e.g., hand tremors, to which the endoscopic instrument is subject are damped. Moreover, as the contact between the O-ring and the instrument is preferably located at the distal end of the cannula, an effective fulcrum for the instrument is provided relatively close to the surgical site, facilitating direction of the instrument and reducing muscle fatigue.

Figures 40, 41:
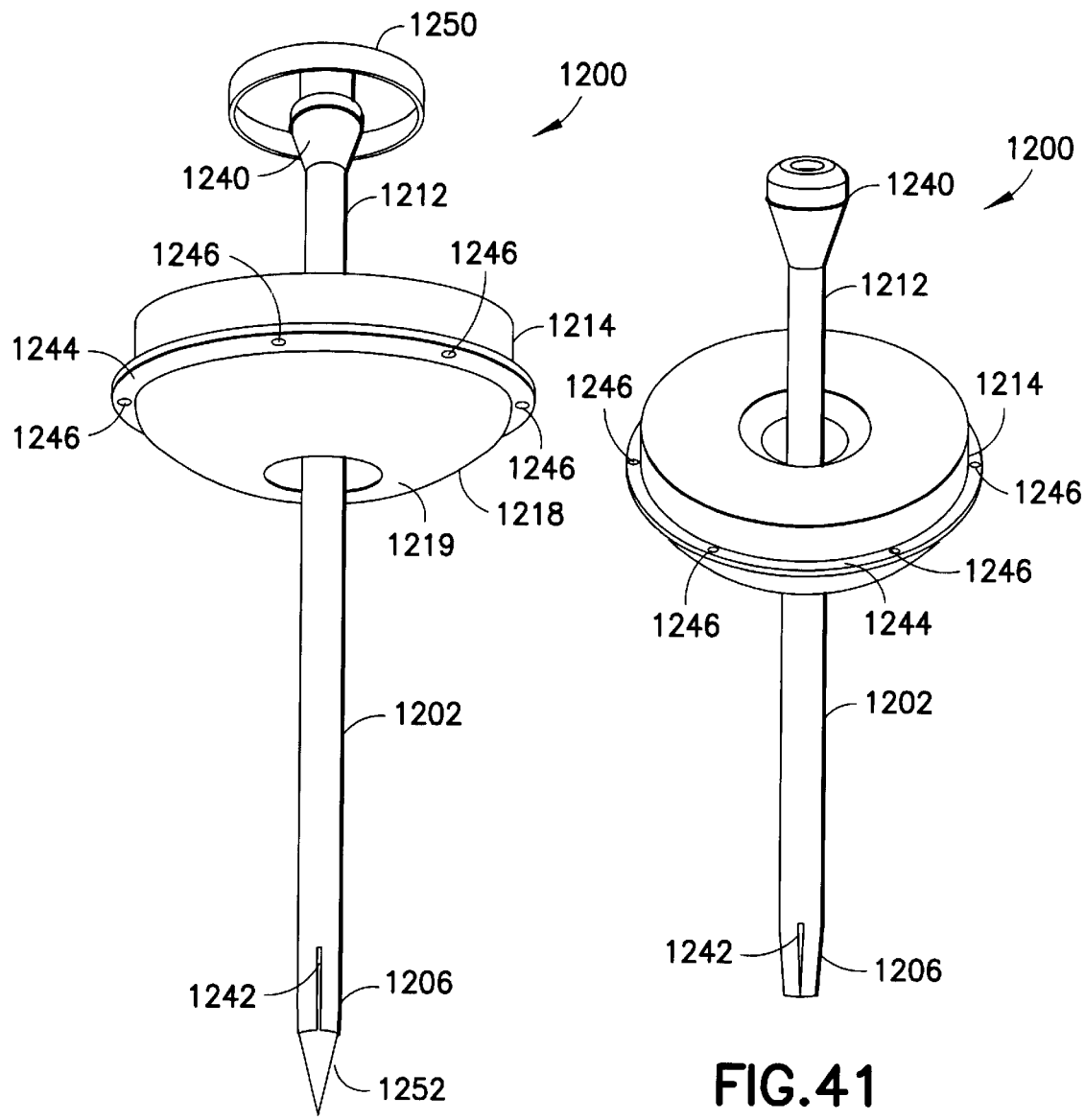
FIG. 40 is a lower perspective view of a second embodiment of the instrument stabilizer of the invention, shown in with a puncture rod extending within the stabilizer.
FIG. 41 is an upper perspective view of the second embodiment of the instrument stabilizer of the invention.

Referring now to FIGS. 40 and 41, a second embodiment of an instrument stabilizer 1200 according to the invention is shown. The instrument stabilizer 1200 includes a cannula 1202 and a housing 1214 having a stabilized disk 1220, as described with respect to the first embodiment. The cannula 1202 is preferably interference fit within an opening in the disk 1220 such that the cannula may be slid relative thereto, yet maintains its relative position unless subject to a sufficient relative longitudinal force. The proximal end 1212 of the cannula is provided with a ferrule 1240. In addition, the distal end 1206 of the cannula, rather than being provided with a ferrule and grommet (as in the first embodiment), is provided with a taper. The distal end 1206 may be tapered by providing one or more slits 1242 in the distal end and compressing the end about the slit or slits. The taper is sufficient to result in close contact between the cannula and an instrument extending through the cannula.

Referring to FIG. 40, in accord with one preferred aspect of the second embodiment, a puncture rod 1250 may be positioned within the stabilizer 1200 such that a sharp, boring tip 1252 of the puncture rod extends out the distal end of the cannula. Then, when it is desired to use the instrument stabilizer, the puncture rod tip and stabilizer are punctured through the tissue of the patient, and the puncture rod is then removed leaving the stabilizer in place. This permits quick and easy insertion of the stabilizer, creates only a relatively small entry hole, and does not necessitate the use of a port. As an alternative to a sharp tipped puncture rod, the puncture rod may include a blunt cautery tip, which permits cautery current to be applied to cut through the chest wall, but is sufficiently blunt to be relatively atraumatic when cautery current is not applied.

Referring to FIGS. 40 and 41, in accord with another preferred aspect of the second embodiment, a flange 1244 is provided about the circumference of the housing 1214. The flange includes a plurality of preferably evenly spaced-apart suture holes 1246. The suture holes 1246 provide locations at which the instrument stabilizer may be sutured directly to the patient. Other means for coupling the instrument stabilizer directly to the patient may also be used. For example, the lower surface 1219 of the lower shell 1218 is preferably convex and may be provided with an adhesive capable of temporarily adhering the instrument stabilizer to the skin of the patient. As yet another example, the lower shell 1218 may be adapted to apply a vacuum against the skin of the patient. Portions of the lower shell 1218 may be selectively coupled to the skin through the use of several suction zones (e.g., four, each extending through a quadrant of the lower shell) which can be individually selected to apply suction. As such, the stabilized disk is then clearly able to operate in conjunction with the damping properties of the flesh of the patient to dampen errant movement applied to an endoscopic instrument extending through the stabilizer 1200.

Figure 42:
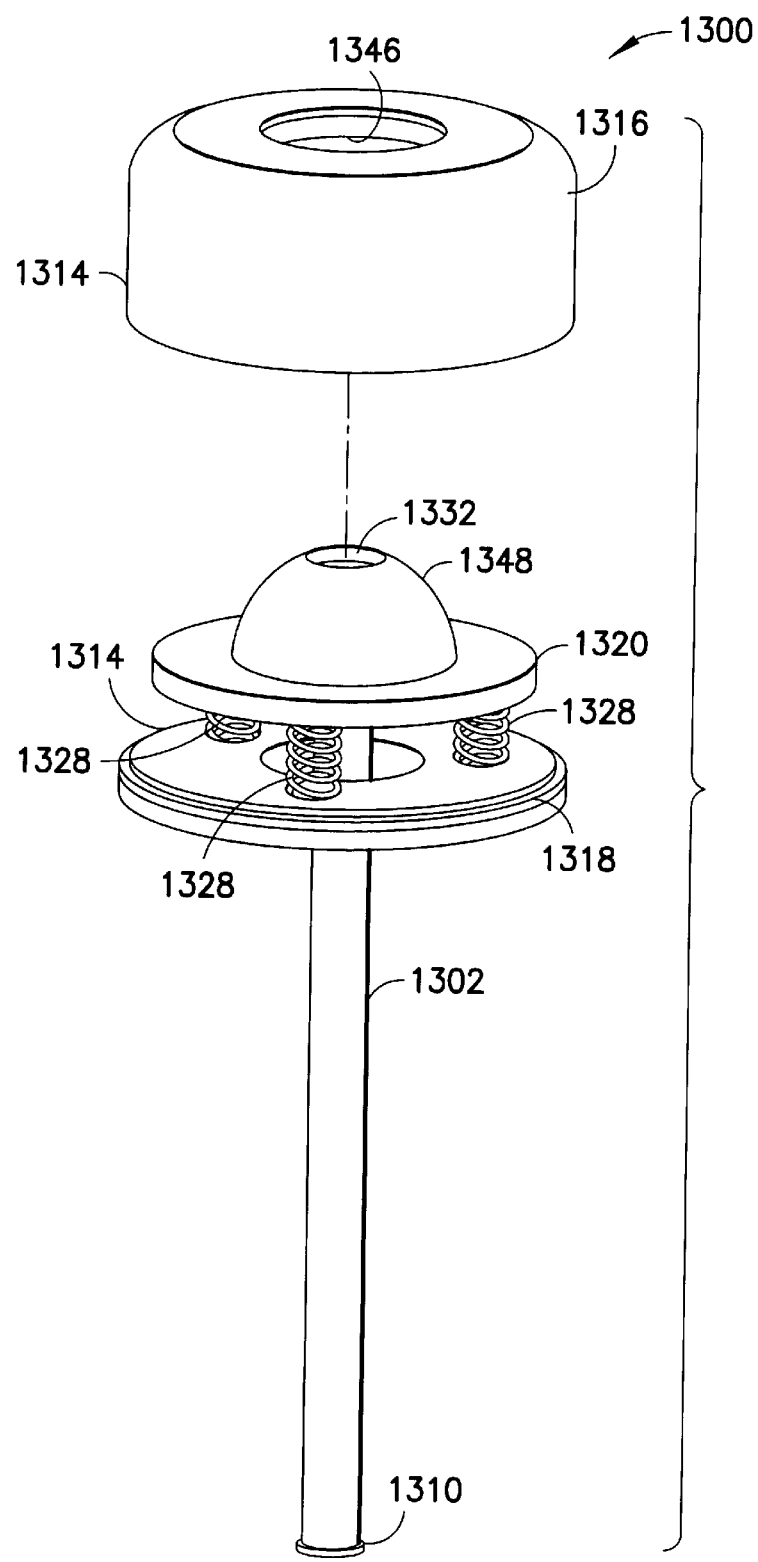
FIG. 42 is an exploded view of a third embodiment of the instrument stabilizer of the invention.

Turning now to FIG. 42, a third embodiment of an instrument stabilizer 1300, substantially similar to the first embodiment, is shown. The third embodiment includes a single set of springs 1328 located between the lower shell 1318 and the lower side of the disk 1320. The upper shell 1316 includes a concave, preferably hemispherical interior surface 1346. The upper side of the disk 1320 is provided with a hemispherical portion 1348. A central opening 1332 extends through the disk 1320 including the hemispherical portion 1348 of the disk. The hemispherical portion 1348 is forced by the springs against the concave interior surface 1346 of the upper shell. The cannula 1302 is provided with a distal bushing 1310 having an opening (not shown) sized to be in close contact with an instrument extending through the cannula. As the instrument is moved relative to the housing 1314, the hemispherical portion 1348 of the disk 1320 articulates relative to the interior surface 1346 of the upper shell 1316. However, movement of the instrument is damped by the springs 1328.

Figure 43:
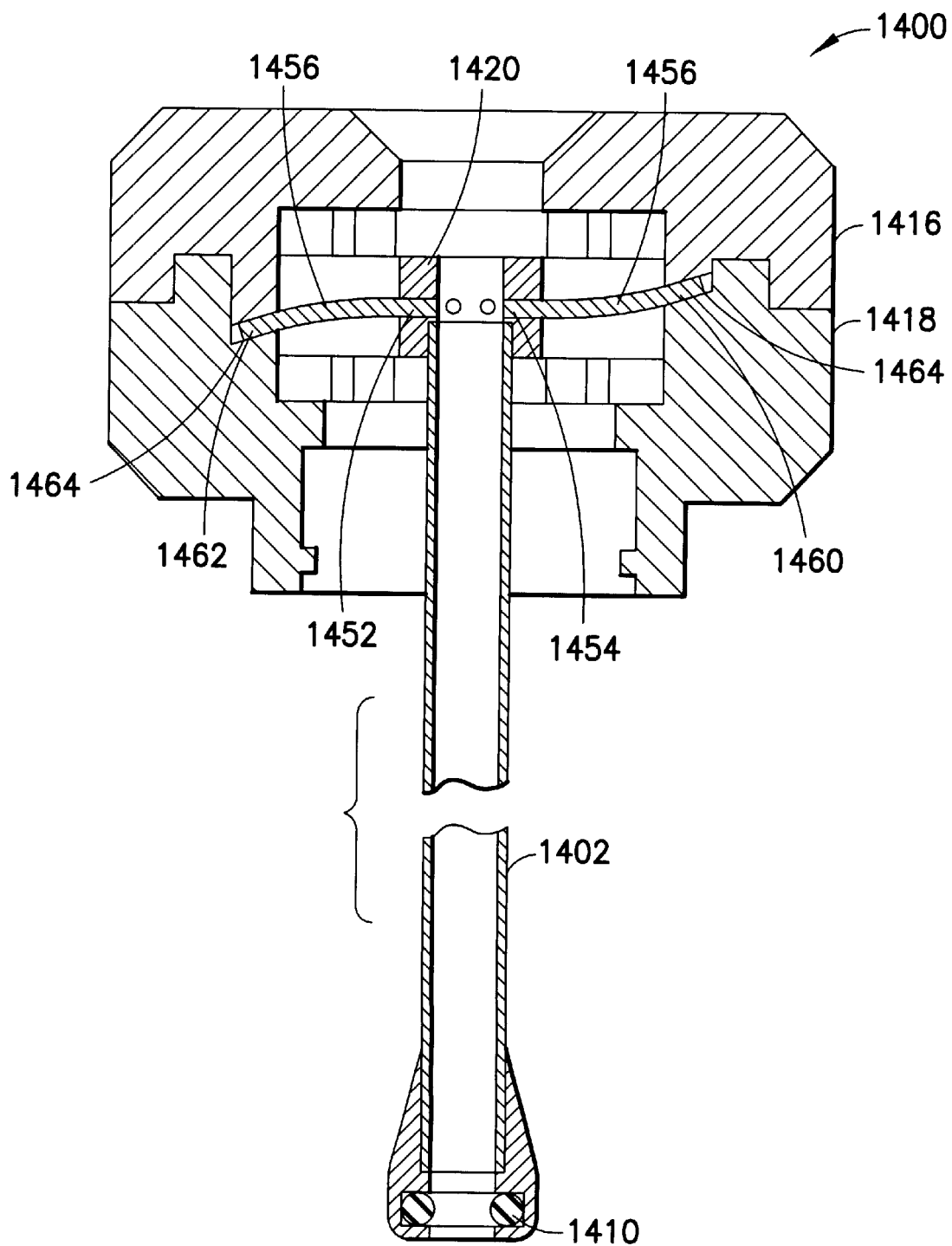
FIG. 43 is a longitudinal section view of a fourth embodiment of the instrument stabilizer of the invention.
Figures 44, 45:
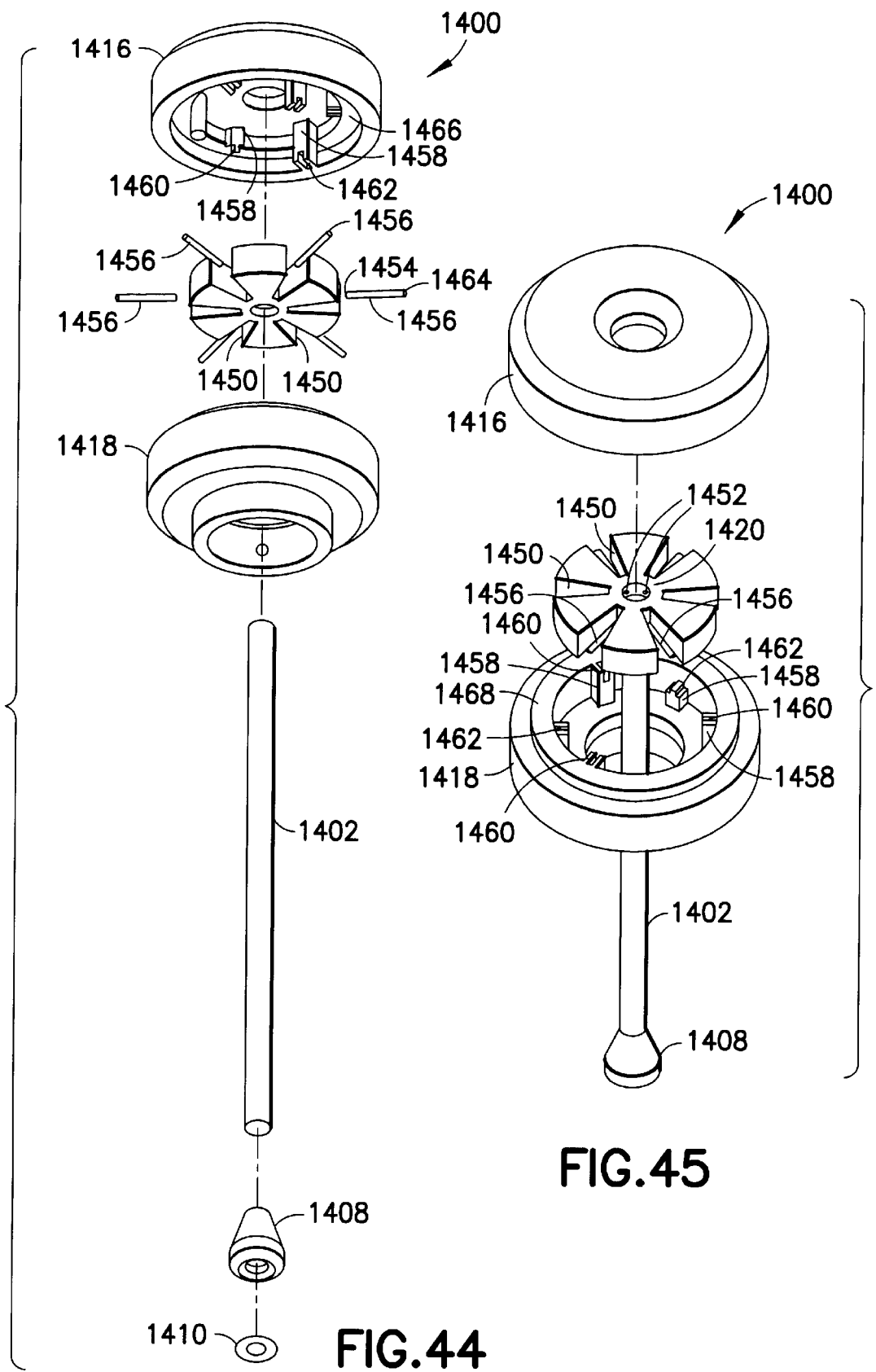
FIG. 44 is an exploded bottom perspective view of the fourth embodiment of the instrument stabilizer of the invention.
FIG. 45 is an exploded top perspective view of the fourth embodiment of the instrument stabilizer of the invention.

Referring now to FIGS. 43 through 45, a fourth embodiment of an instrument stabilizer 1400, substantially similar to the first embodiment, is shown. The instrument stabilizer 1400 includes upper and lower shells 1416, 1418, and a disk 1420 therebetween. The disk 1420 is provided between the upper and lower shells, and includes six radial slots 1450 and a radial bore 1452 centrally located relative to each slot. Each radial bore 1452 is provided with a first end 1454 of a strut 1456. The interior of each shell 1416, 1418 includes six circumferentially positioned, equally spaced apart strut mounts 1458. The strut mounts 1458 are provided with alternating upper and lower strut purchases 1460, 1462, angled downward and upward, respectively (FIG. 43), on which to receive a second end 1464 of a respective strut 1456. The upper shell 1416 includes a circular channel 1466, and the lower shell 1418 includes a circular ridge 1468 sized to fit within the channel 1466. The upper and lower shells 1416, 1418 are sandwiched about the disk 1420 such that second end 1464 of the struts 1456 are received by the respective strut mounts 1458 of the upper and lower shells, and such that the ridge 1468 fits within the channel 1466. The shells 1416, 1418 are then assembled together and sealed to each other, e.g., via sonic welding. With the shells assembled, alternating struts 1456 are bent in upward and downward configurations. Together the struts provide a stabilizing force to the disk. The cannula 1402 is coupled within the disk 1420, and movement of an endoscopic instrument through an O-ring 1410 in a ferrule 1408 of the cannula 1402, is thereby damped.

Figure 46:
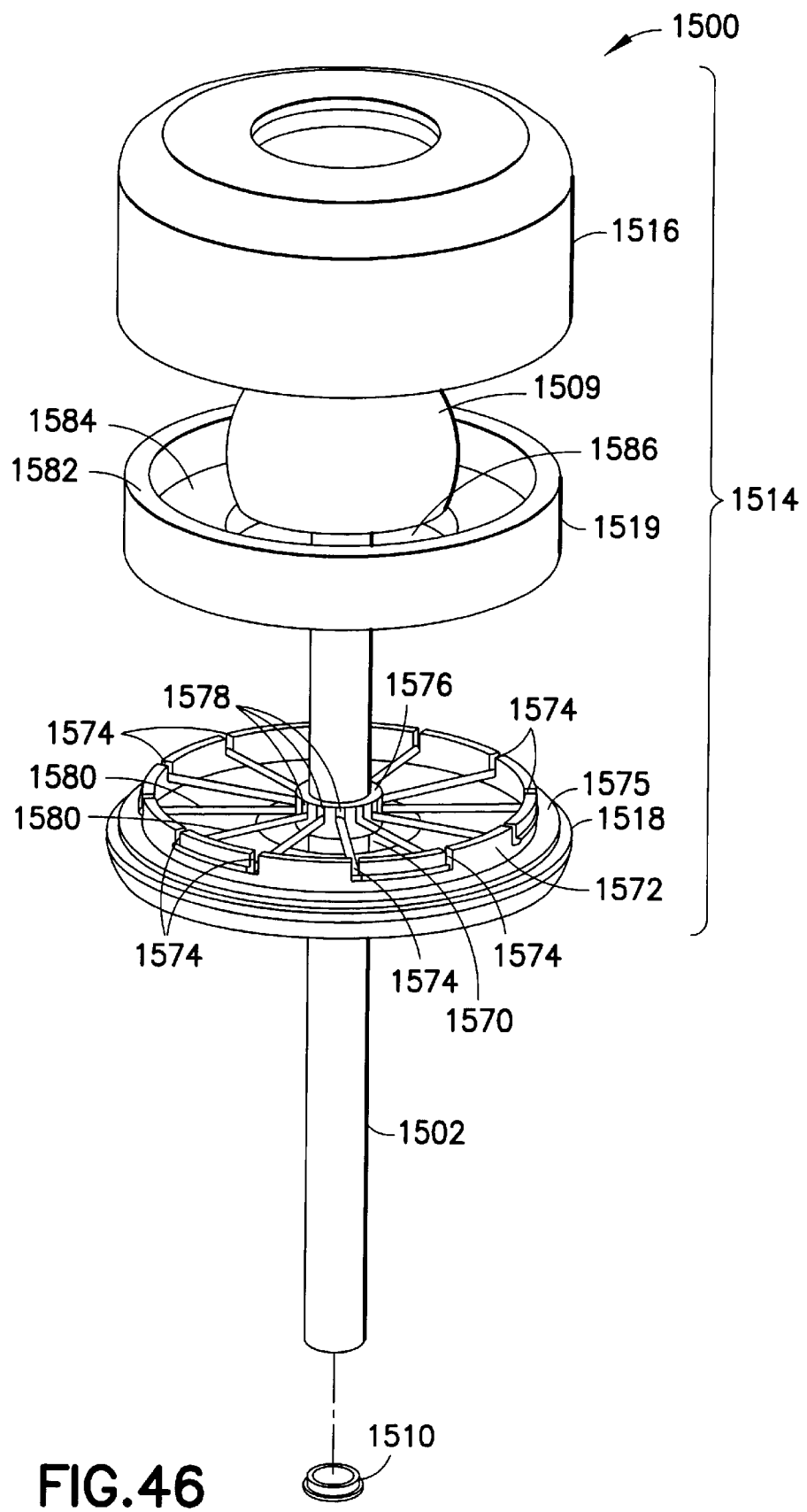
FIG. 46 is an exploded perspective view of a fifth embodiment of an instrument stabilizer of the invention.

Referring now to FIG. 46, a fifth embodiment of an instrument stabilizer 1500 is provided. The instrument stabilizer 1500 includes a cannula 1502 coupled to a housing 1514. The cannula 1502 is provided with a proximal hemispherical head 1509 providing an opening into the cannula, and a distal grommet 1510 sized to be in close contact with an endoscopic instrument extending through the cannula. The housing 1514 includes a lower platform 1518, an upper cap 1516, and a central ring 1519 therebetween. The upper cap 1516 includes a concave interior surface (not shown) on which the hemispherical head 1509 can articulate, and an interior lip (not shown). The lower platform 1518 includes a central opening 1570, a peripheral circular ridge 1572 provided with a plurality of spaced apart slots 1574, and an outer lip 1575. A collar 1576 is rigidly coupled about a portion of the cannula 1502, and positioned within the ridge 1572 of the platform 1518. The collar 1576 includes a plurality of slots 1578 corresponding to the slots 1574 on the ridge 1572. One or more elastic or resilient band or bands 1580 extend between and within the slots 1574 and 1578 to stabilize the collar 1576 relative to the opening 1570 of the platform 1518. The central ring 1519 includes an outer wall 1582 and a plate portion 1584 with a central opening 1586. When the upper cap 1516 is joined with the platform 1518, the outer wall 1582 is held between the interior lip of the upper cap 1516 and the outer lip 1575 of the platform 1518. The plate portion 1584 operates to prevent disengagement of the bands 1580 from the slots 1574, 1578 when the housing 1514 is assembled and the cannula 1502 is moved relative to the housing. When an instrument is positioned through the cannula 1502 and in contact with the grommet 1510, movement of the instrument is damped and stabilized by the close fit arrangement of the grommet 1510 and the forces of the bands 1580 on the collar 1576 and cannula 1502.

Figure 46A:
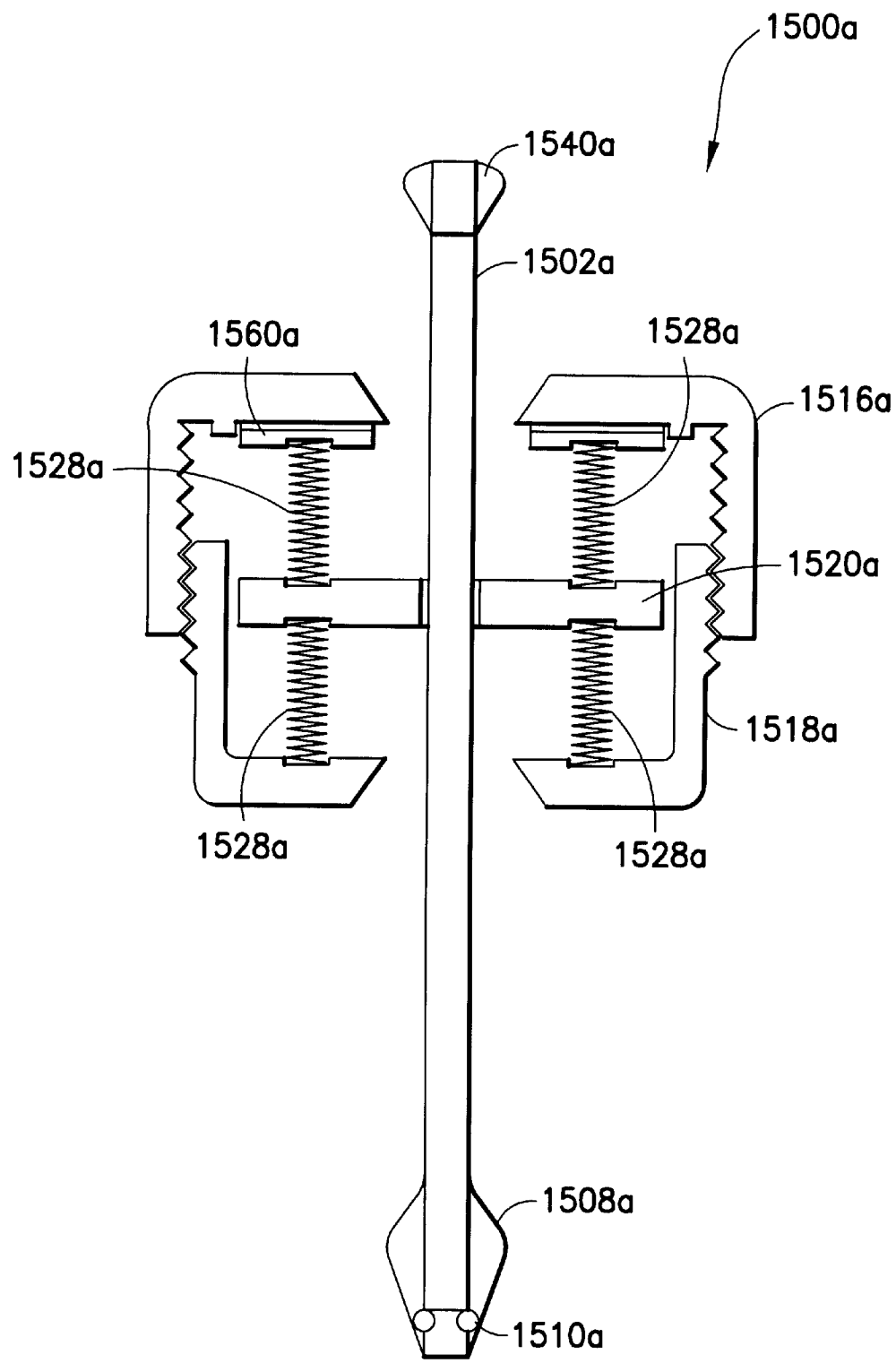
FIG. 46a is a longitudinal section view of a sixth embodiment of the instrument stabilizer of the invention.
Figure 46B:
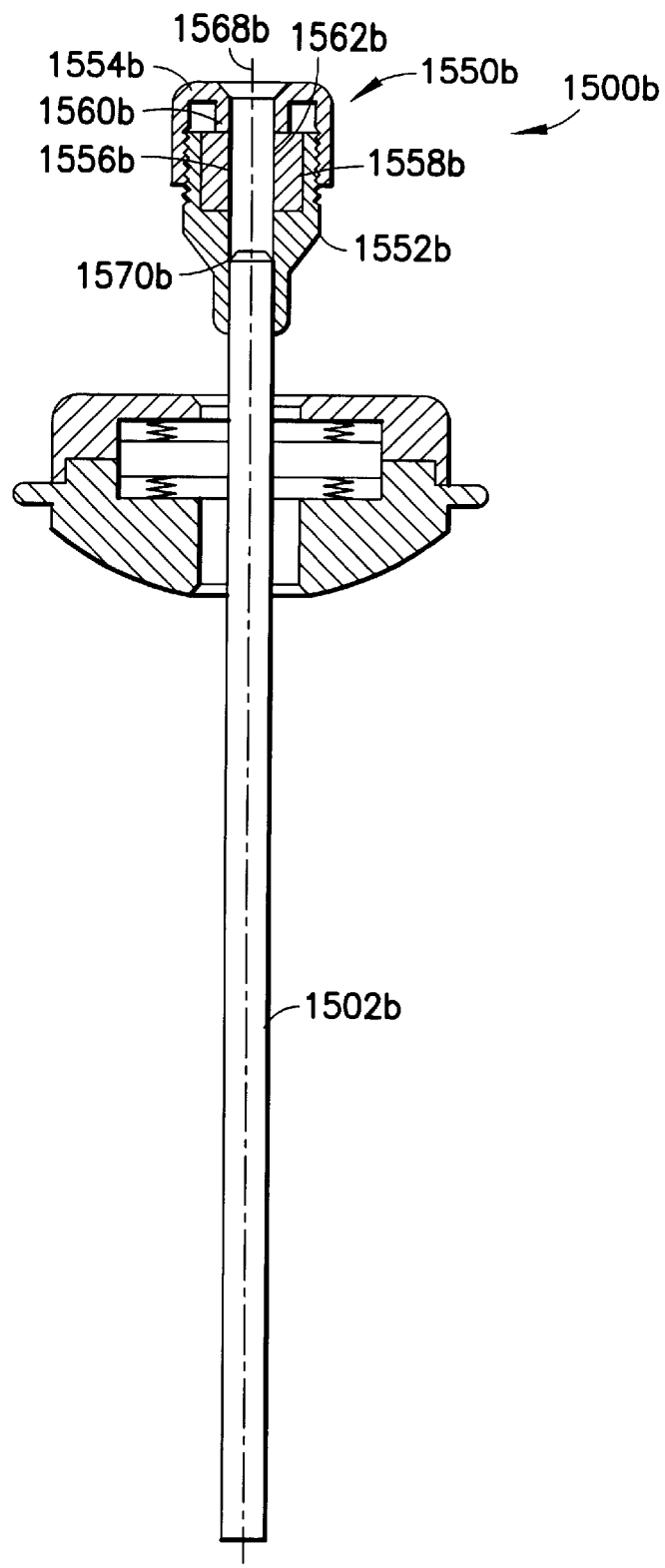

Referring now to FIG. 46a, a sixth embodiment of an instrument stabilizer 1500a is shown. The instrument stabilizer 1500a includes a cannula 1502a interference fit in a disk 1520a, as described in the second embodiment. The proximal end 1512a of the cannula 1502a is provided with a ferrule 1540a, and the distal end 1506a is provided with a ferrule and grommet, as in the first embodiment. Upper and lower shells 1516a, 1518a in a threaded engagement surround the disk 1520a. A plate 1560a is provided against the interior upper surface of the upper shell and permitted to rotate relative thereagainst. Compression springs 1528a are provided on each side of the disk, as described with respect to the first embodiment, such that the disk 1520a 'floats' between the upper and lower shells. The shells 1516a and 1518a may be rotated relative to each other such that the shells the springs are further compressed (e.g., via clockwise rotation) and reduced in compression (e.g., via counterclockwise rotation), thereby controllably altering the stabilizing force upon the cannula.

Figure 66:
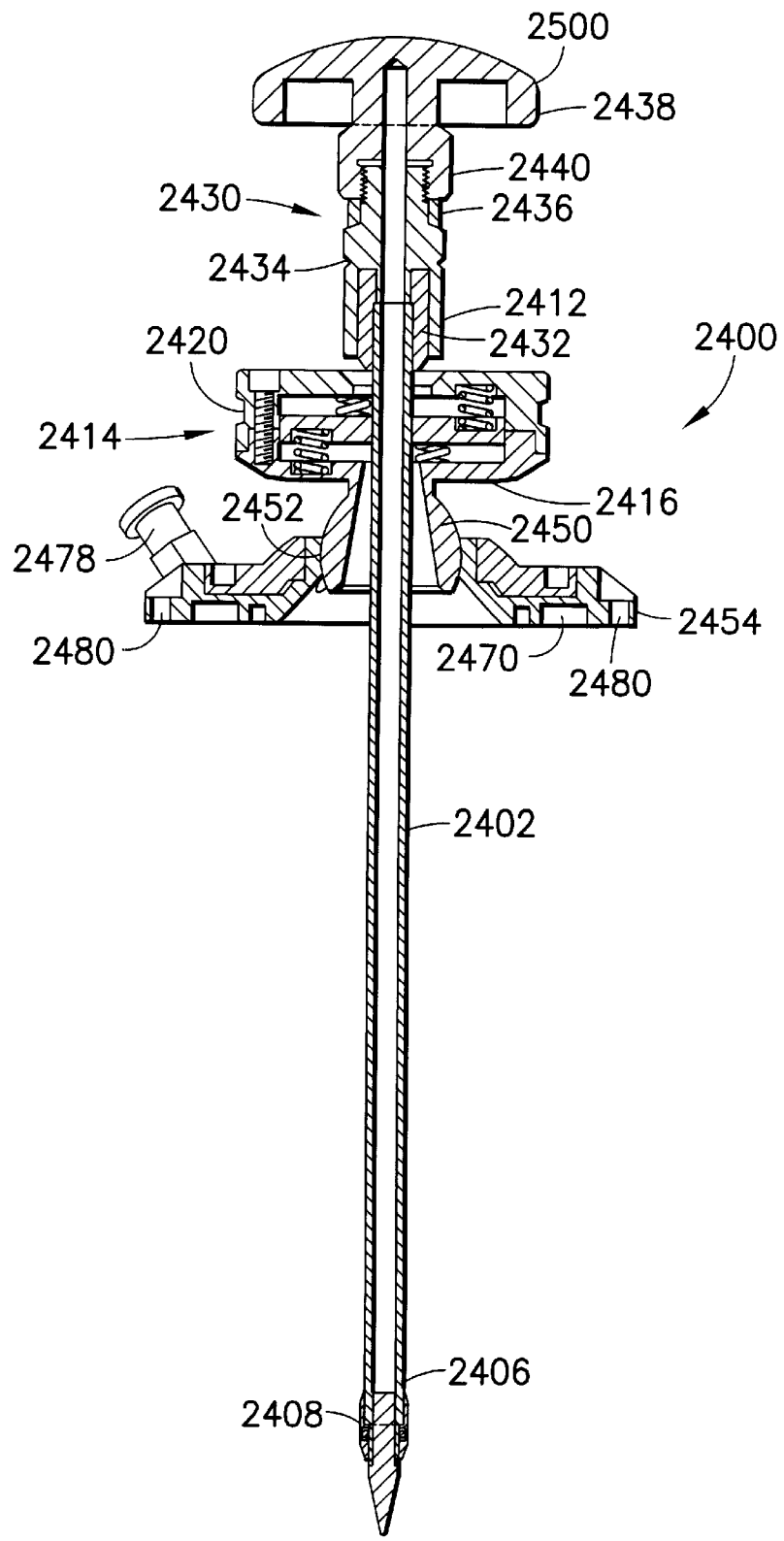
FIG. 66 is a longitudinal section view of a seventh embodiment of an instrument stabilizer according to the invention, shown with a puncture rod inserted therein.
Figure 67:
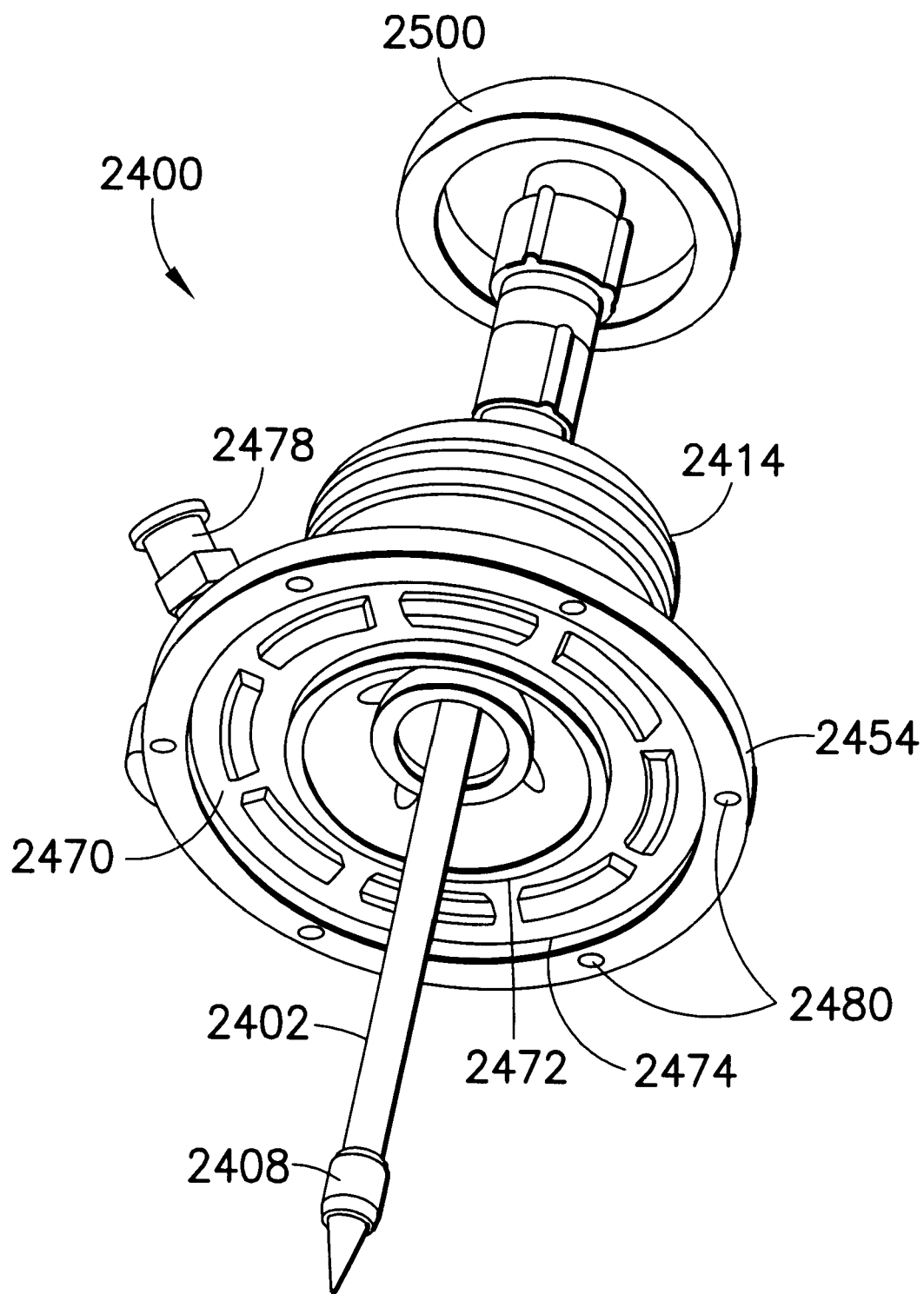
FIG. 67 is a bottom perspective view of the seventh embodiment of an instrument stabilizer, shown with a puncture rod inserted therein.
Figure 68:
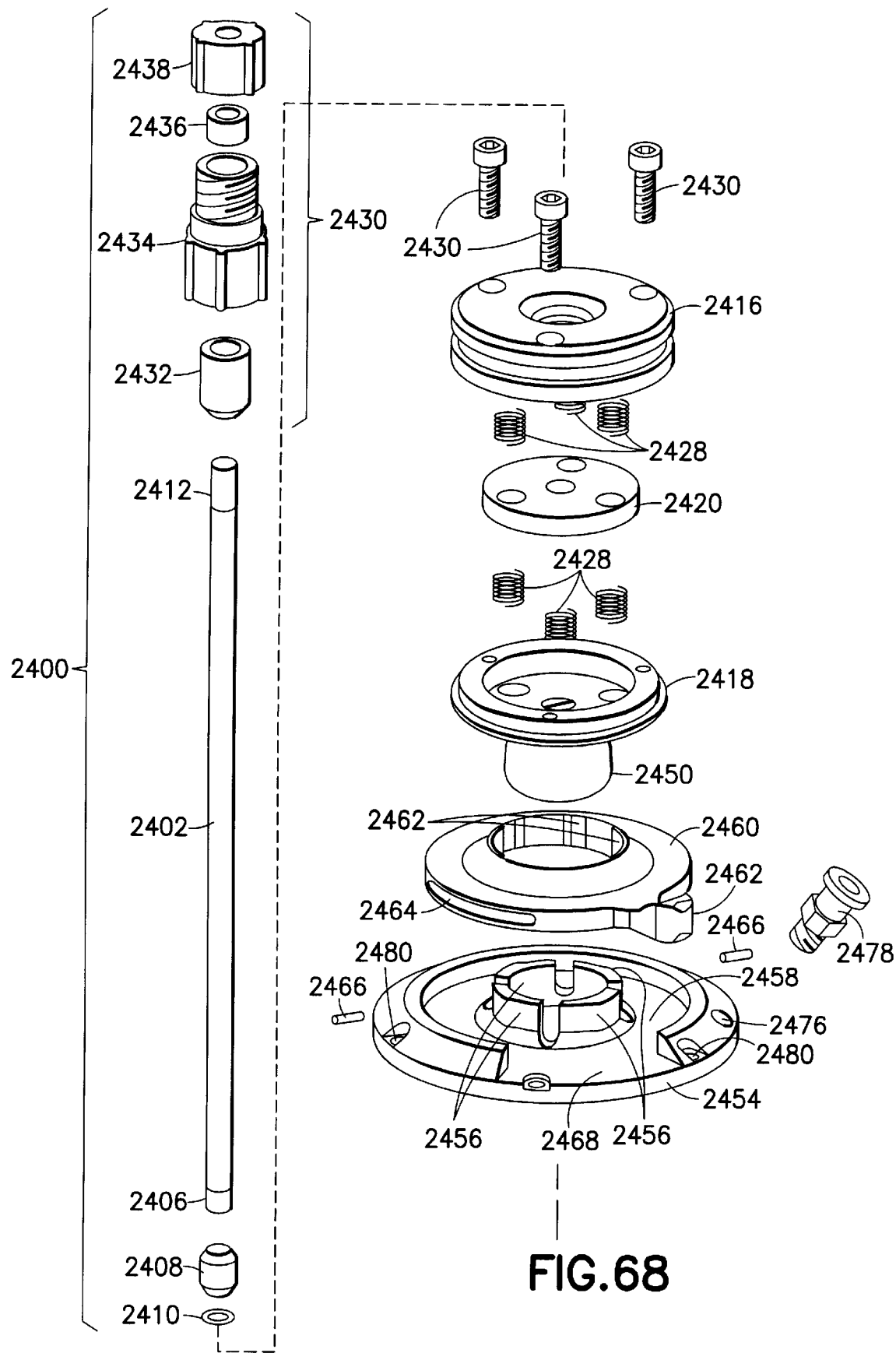
FIG. 68 is an exploded perspective view of the seventh embodiment of an instrument stabilizer.

Referring now to FIGS. 66 through 68, a seventh embodiment of an instrument stabilizer 2400 according to the invention is shown. In FIGS. 66 and 67, a puncture rod 2500 is shown extending through the cannula 2402 of the stabilizer. The cannula 2402 of the stabilizer extends through a housing 2414 having a stabilized disk 2420, as described with respect to the first embodiment. The cannula 2402 is preferably in an interference fit within an opening in the disk 2420 such that the cannula may be slid relative thereto, yet maintains its relative position unless subject to a sufficient relative longitudinal force.

Figure 69:
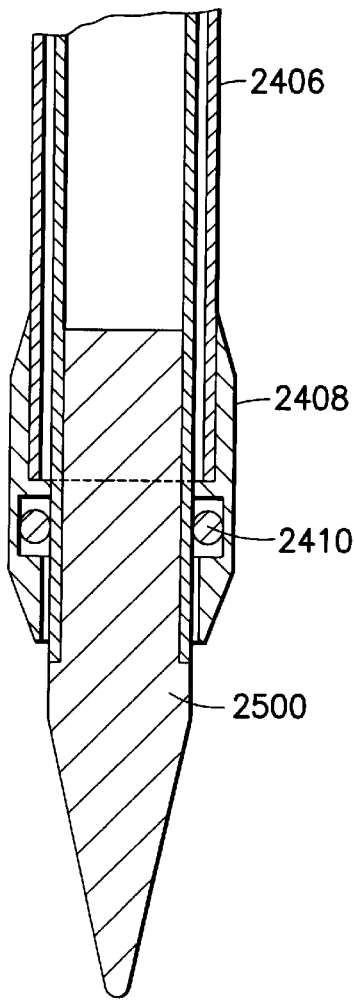
FIG. 69 is an enlarged broken section view of the housing of the seventh embodiment of an instrument stabilizer.

According to one preferred aspect of the seventh embodiment, the proximal end 2412 of the cannula is provided with an adjustable seal assembly 2430 adapted to change the diameter at the entry of the cannula and form a seal about an instrument extended therethrough. This assembly 2430 preferably includes an adapter 2432 provided on the proximal end of the cannula, a seal housing 2434 provided on the adapter 2432, a resilient compressible bushing 2436 provided in the seal housing 2434, and seal cap 2438 thread on the seal housing 2434. The seal cap 2438 includes a central portion 2440 (FIG. 66) positioned to axially compress the bushing 2436 and thereby decrease its diameter when the seal cap 2438 is rotated relative to the seal housing 2434. The distal end 2406 of the cannula is provided with another ferrule 2408 and grommet 2410 sized to contact the puncture rod 2500 or another instrument extending therethrough (FIG. 69).

Figure 70:
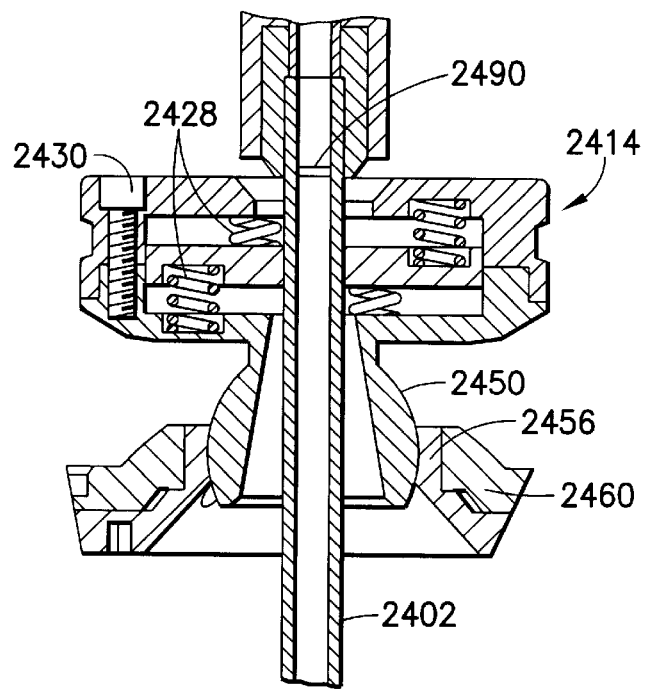
FIG. 70 is an enlarged broken section view of the distal end of the seventh embodiment of an instrument stabilizer, shown with a puncture rod inserted therein.
Figure 73:
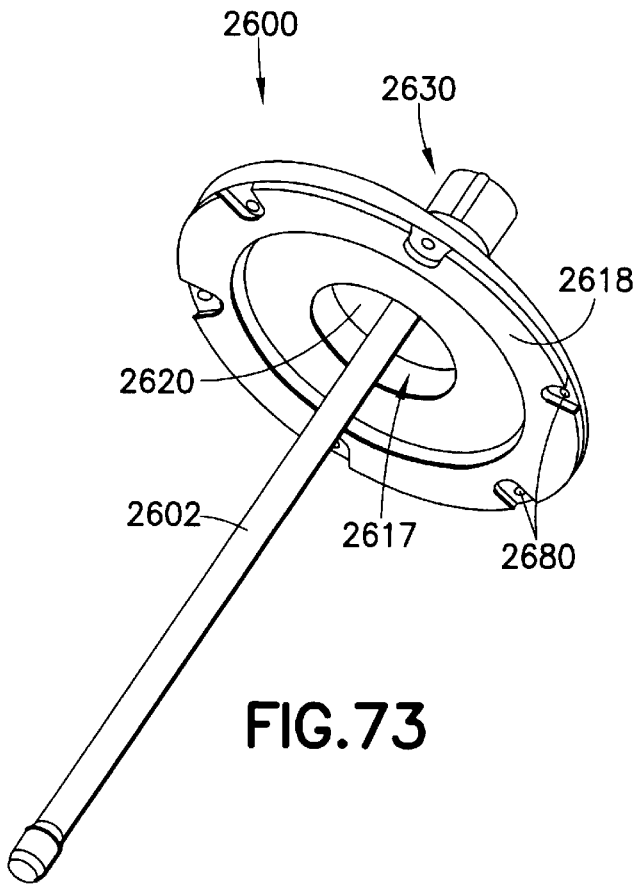
FIG. 73 is a bottom perspective view of the eighth embodiment of an instrument stabilizer according to the invention.

The cannula 2402 optionally includes a valve 2490 (FIG. 70). The valve 2490 (e.g., a flapper, a duckbill or another standard valve) permits the instrument stabilizer to be used for surgical procedures requiring insufflation of the body cavity in which the instrument stabilizer is inserted. The valve 2490 may be provided within the cannula, as shown, or at a location proximal or distal of the cannula. When the valve 2490 is in a closed position, fluid is substantially prevented from passing through the cannula. Preferably, insertion of an endoscopic instrument through the cannula and against the valve automatically opens the valve such that the endoscopic instrument may be moved through the cannula.

Referring to FIGS. 66, 67, 68 and 70, according to another preferred aspect of the seventh embodiment of the instrument stabilizer, the stabilizer housing 2414 includes an upper cap 2416 and a ball base 2418 which together house the disk 2420 and springs 2428. Screws 2430 secure the upper cap 2414 and ball base 2416 together. The ball base 2416 includes a lower oblate spheroid portion 2450 which is coupled in a socket 2452 of a vacuum plate 2454. The socket 2452 is partially defined by four cam surface 2456 on an upper surface of the plate 2454. The upper surface of the plate 2454 also includes a generally annular channel 2458. A ring-shaped locking lever 2460 is received in the channel 2458 and includes inner cams 2462 which, when the lever 2460 is rotated within the channel, contact and radially compress the cam surfaces 2456 to thereby lock the ball base 2418 in position. The lever 2460 includes a handle 2462 to facilitate rotation, and two peripheral slots (one shown) 2464. Two dowel pins 2466 extend radially into the plate 2454 and into the slots 2464 to retain the lever 2460 on the plate, but permit its rotation. Rotation is limited by the handle 2462 which may only travel through a peripheral opening 2468 in the plate 2454. The bottom of the plate 2454 defines a vacuum path 2470 having generally two concentric circular portions 2472, 2474. The vacuum path 2470 is in fluid communication with a hole 2476 extending to the upper surface of the plate 2454, and a luer connector 2478 is coupled in the hole. When a vacuum source (not shown) is coupled to the luer connector 2478 and the plate 2454 is placed on the human body, the negative pressure within the vacuum path 2470 secures the plate, and the instrument stabilizer 2400 to the human body. The plate 2454 may include other vacuum paths. For example, referring to FIG. 71, the vacuum path 2470a of plate 2454 may include a plurality of circular openings 2472a in fluid communication with a ring-like path 2474a which is in fluid communication with the luer connector 2478. Referring to FIGS. 67 and 71, holes 2480 about the periphery of the plate 2454 may also be used to suture the plate to the tissue of the human body to further secure the stabilizer thereto.

Figure 74:
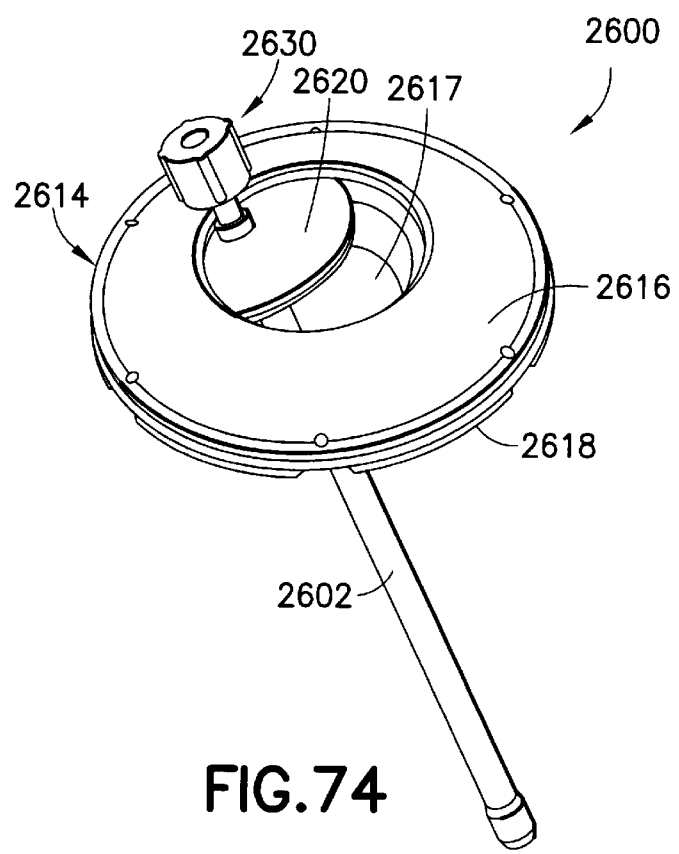
FIG. 74 is a top perspective view of the eighth embodiment of an instrument stabilizer according to the invention, shown in an angled configuration.

Turning now to FIGS. 72 through 76, an eighth embodiment of an instrument stabilizer 2600 is shown. The instrument stabilizer 2600 includes a cannula 2602 having an adjustable seal assembly 2630 at a proximal end and a ferrule 2608 holding a grommet 2610 at a distal end (FIG. 76), as described above with respect to seal assembly 2430, above. A flange 2620 having a spherical radius of curvature is provided about the cannula 2602. The cannula 2602 extends through a housing 2614 having a dome-shaped cap 2616 with a central opening 2617 and a lower base 2618 having a frustoconical opening 2619. The cap 2616 and the base 2618 together define a channel 2615 having a spherical radius of curvature substantially the same as that of the flange 2620 and through which the flange may move. The housing 2614 includes a plurality of peripheral holes 2680. During use, the distal end of the cannula 2602 is inserted through a puncture hole in the patient's body and the housing 2614 is then sutured via the peripheral holes 2680 to the patient so that the housing 2614 sits over the puncture hole. Then, when the cannula 2602 is angled relative to the housing 2614 (as shown in FIGS. 74 through 76), the body tissue of the patient provides the stabilizing force to dampen unwanted movement of an instrument extending through the cannula. The centers of the radius of curvature of the flange 2620 and the channel 2682 preferably reside within the body of the patient during use.

Figure 47:
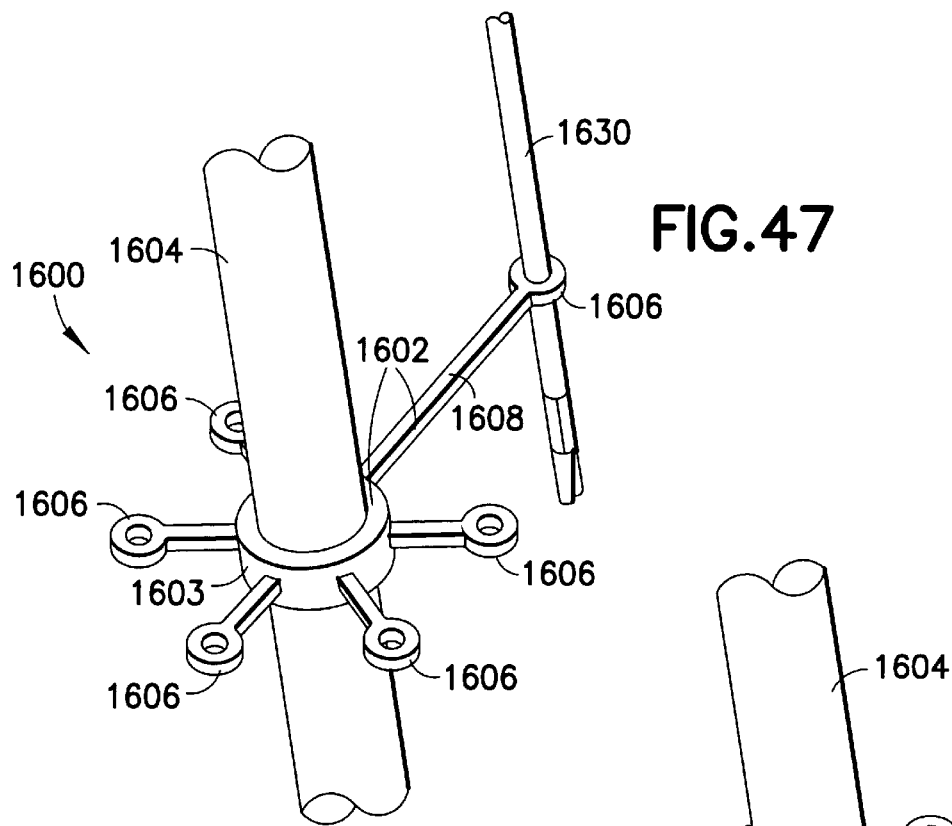
FIG. 47 is a perspective view of a ninth embodiment of the instrument stabilizer of the invention.
Figure 48:
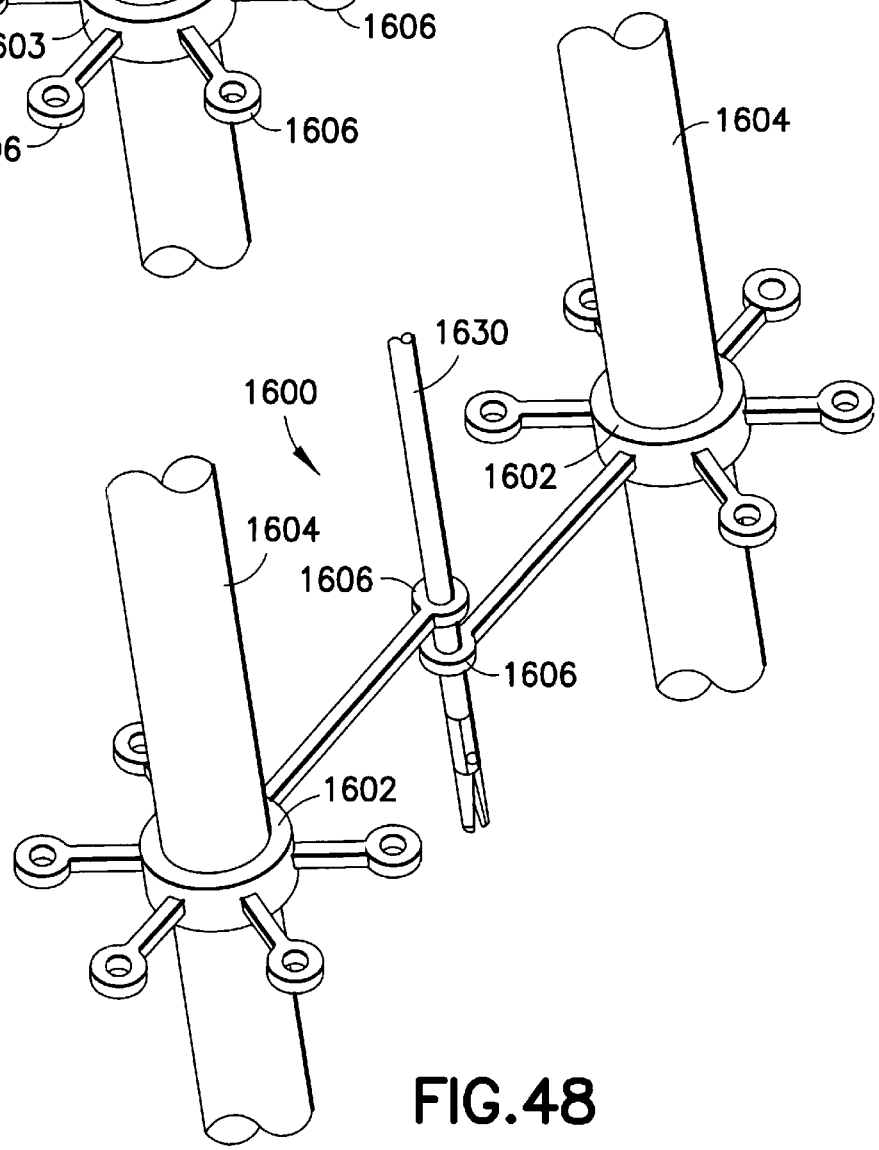
FIG. 48 is a perspective view of a tenth embodiment of the instrument stabilizer of the invention.

Turning now to FIG. 47, a ninth embodiment of an instrument stabilizer 1600 is shown. The instrument stabilizer 1600 includes an instrument coupler 1602 and a preferably stable shaft 1604. The instrument coupler 1602 is preferably elastic and preferably includes a central collar 1603 and plurality of rings 1606 or other instrument gripping means, e.g., ties, collars, tubes, clamps, etc., coupled via an elastic tether 1608 to the preferably ring-shaped shaft collar 1603. The shaft 1604 may be dedicated to the instrument stabilizer, or optionally may be a stabilized shaft of another instrument, e.g., the above described heart stabilizer or another instrument which is substantially stable during a surgical procedure. A surgical instrument 1630 is inserted through one of the rings 1606. Several rings may be occupied by several surgical instruments; the rings being preferably selected based on those which provide best access to the surgical site. The elastic tethers extending from the rings to the shaft collar operate to dampen the unwanted movements to which the surgical instruments are subject. In addition, referring to FIG. 48, instrument coupler 1602 may be used on a plurality of shafts 1604 such that a single instrument 1630 is stabilized by more than one coupler 1602, further damping forces to which the instrument 1630 is subject.

It is intended that the various features of the several embodiments may be utilized in other combinations. As such, while various means for coupling an instrument stabilizer to a patient's body or a port or a shaft (in the case of the ninth embodiment), have been disclosed, it will be appreciated that other suitable means may be used. Furthermore, while in the first through ninth embodiments of the instrument stabilizer, the cannula is coupled to a disk or provided with a flange which is stabilized within the housing, plates other than disc-shaped, e.g, triangular, may be used. Moreover, other damping means may be used. For example, a rubber or other resilient-material plate held within the housing can be used. Such a rubber plate is self-damping and does not require any springs, bands, etc. In addition, while various means having been disclosed for stabilizing and damping the forces to which a surgical instrument and a cannula are subject, it will be appreciated that other means may likewise be used. Furthermore, while an O-ring, a grommet, and a tapered cannula have been disclosed for providing a close fit arrangement with a cannula, other close fitting bushings, e.g., a diaphragm or piece of sponge, may be used. In addition, such bushings may be provided anywhere along the length of the cannula.

However, if the bushing is provided at the proximal end, it is preferable that a close fit between the instrument and the stabilizer also be provided at the distal end. Moreover, an instrument stabilizer may be provided which includes only one of the stabilized disk and the close fit bushing without the other, as discussed in the eighth embodiment. Also, each of the first through sixth and eighth embodiments of the instrument stabilizer may include a seal assembly and/or a valve, as discussed in the seventh embodiment.

Turning now to FIGS. 49 and 50, a stabilizer swivel 1700 according to the invention is shown. The stabilizer swivel, as described further below, permits an instrument stabilizer, such as stabilizer 1100, to be maintained at an angle relative to a location on the body of a patient. The stabilizer swivel 1700 includes upper and lower complementary wedge elements 1702, 1704, respectively, together preferably defining a cylinder, and a disk 1720.

The upper wedge element 1702 includes: an upper surface 1705 provided with a tubular mating portion 1706 defining an opening 1707 through element 1702, a lower surface 1711 including a circular recess 1708 having a periphery 1709, and three threaded bores 1710 spaced about the opening 1707 and extending into the recessed portion of the upper wedge in a direction preferably normal to the surface 1712 of the recess 1708. The upper surface 1705 and lower surface 1711 are preferably at an approximately 22.5° angle relative to each other. In addition, a locking screw 1714 extends through the upper wedge in a direction preferably normal to the upper surface 1705 of the upper wedge.

The lower wedge 1704 includes: an upper surface 1715, a lower surface 1716, a central opening 1717 which is preferably relatively larger than the opening 1707, and three threaded bores 1718 extending into the lower wedge preferably normal to the upper surface 1715 of the lower wedge and preferably equally spaced apart about the opening 1717. The upper surface 1715 and the lower surface 1716 of the lower wedge element are preferably at an approximately 22.5° relative to each other.

The disk 1720 includes a circumferential bevel 1722 on one side and three holes 1724. The disk 1720 is provided in the recess 1708 between the upper and lower wedges 1702, 1704. Preferably three screws 1726, each having a tapered and substantially flat head 1728, are engaged in the three threaded bores 1718, with the taper of the head of the screws 1726 lying complementary to the bevel 1722 on the disk 1720 such that the screws 1726 surround and retain the disk while still permitting the disk to rotate relative to the lower wedge 1704. A second set of screws 1730 extend up through the holes 1724 of the disk and secure the disk in the recess 1708 of the upper wedge 1702. The disk 1720 and periphery 1709 of the recess together define a track through which the heads 1728 of the screws 1726 may be rotated. As such, the upper and lower wedges are coupled to each other and are also permitted to rotate relative to each other such that the tubular mating portion 1706 may be directed at various angles relative to the central opening 1717 of the lower wedge 1704 (FIGS. 51 and 52), and therefore the surface on which the lower wedge is seated. With the given angles of the surfaces of the upper and lower wedges, the tubular mating portion may be directed between 0° and 45° relative to the opening of the lower wedge. It will be appreciated that by providing other relative angles to the respective upper and lower surfaces, a different range of angles at which the mating portion may be directed is obtained. Other mechanisms permitting relative rotational configurations of the upper and lower wedges may also be used.

Referring to FIG. 52, the central opening 1717 is sized such that even when a maximum angle is provided between the mating portion 1706 and the central opening, the pathway through the mating portion is unobstructed at preferably all locations, as indicated by arrow A. Once a desired relative angle is provided, the locking screw 1714 is tightened in to contact with the lower wedge, thereby causing the upper and lower wedges to be forced apart at one side and resulting in sufficient resistance to rotation at the opposite side. Loosening of the locking screw 1714 again permits relative rotation of the upper and lower wedges 1702, 1704.

Figure 53:
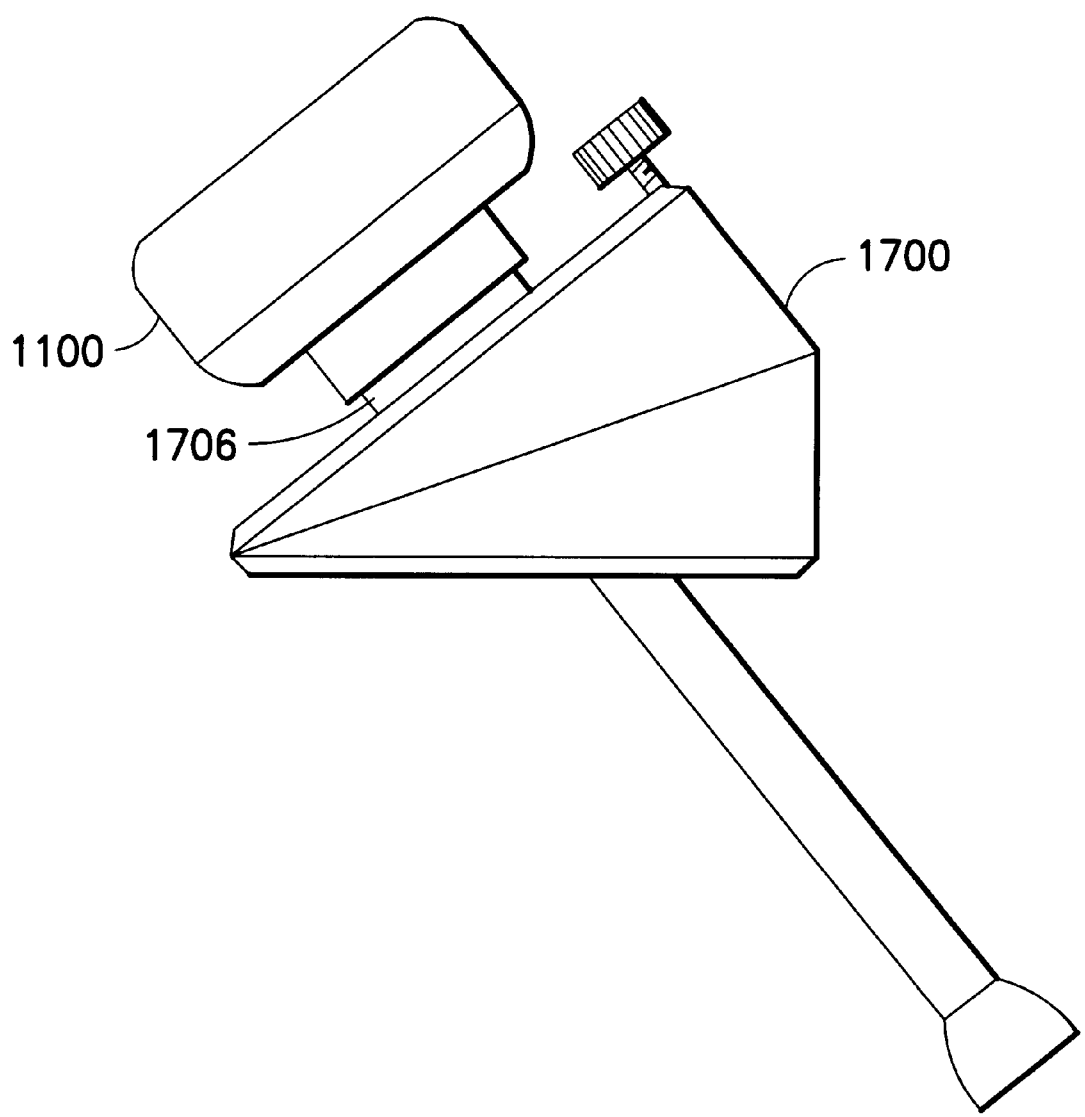
FIG. 53 is a side view of an instrument stabilizer coupled to the stabilizer swivel in the second angular orientation.

Turning now to FIG. 53, an instrument stabilizer, e.g., stabilizer 1100, may be coupled to the stabilizer swivel 1700 at the tubular mating portion 1706. The stabilizer 1100 may then be angled relative to the surface on which the stabilizer swivel is seated, i.e., the patient, to facilitate maintaining the stabilizer, and therefore an instrument extending therethrough, at a desired orientation. Moreover, it will be appreciated that the swivel 1700 can be integrated into an instrument stabilizer such that the two are in a common instrument.

According to a preferred method which utilizes the system, a port device is stably positioned, e.g. clamped, in the chest wall and directed as necessary for operation on the heart wall. A heart stabilizer is coupled to the port, and operated to apply a compressive force against the heart wall surrounding a location of the required bypass such that the location is substantially immobilized. An instrument stabilizer is inserted through a puncture hole in the chest cavity, and the distal tip of the cannula of the stabilizer is located adjacent to the surgical site. A first surgical instrument, e.g., a scalpel or needle holder, is passed through the cannula and operated to perform at least a portion of the procedure. If other surgical instruments are required, the first instrument may be removed and other instruments may be extended therethrough. Alternatively, an instrument stabilizer may be provided for each instrument. Once the bypass procedure is complete, the instruments and instrument stabilizers are removed from the locus of the surgery, and the heart stabilizer is also removed through its port. Then, the clamping forces on the port is loosened and the port is withdrawn from the chest wall. Finally, the incision and puncture holes in which the port and instrument stabilizer were located are closed. This method eliminates the need for many open heart procedures, as well as the need to stop the heart.

There have been described and illustrated herein several embodiments of a system for performing port off-pump coronary artery bypass surgery and a port device and heart stabilizer therefor. While particular embodiments of the invention have been described, it is not intended that the invention be limited thereto, as it is intended that the invention be as broad in scope as the art will allow and that the specification be read likewise. Therefore, while the elements of the system have been particularly described for use in a port off-pump coronary artery bypass procedure, it will be appreciated that each element may be used alone or in combination for other procedures. In addition, while the port and instrument stabilizer have been described with respect to their use with endoscopic instruments, each may be used with other types of surgical instruments. It will therefore be appreciated by those skilled in the art that yet other modifications could be made to the provided invention without deviating from its spirit and scope as claimed.

What is claimed is:

1. A heart stabilization device, comprising:
   a) a shaft having a proximal end provided with a handle, a distal end, and defining a longitudinal axis; and
   b) a pair of stabilization arm assemblies at said distal end of said shaft, each of said stabilization arms provided with a substantially rigid foot having a contact surface which is adapted to contact a surface of the heart, said feet having a first configuration in which said feet extend substantially parallel to said longitudinal axis and are substantially in contact with each other, and a second configuration in which feet extend substantially parallel to said longitudinal axis and are displaced relative to each other; and c) an actuator adapted to move said feet between said first and second configurations.

2. A heart stabilization device according to claim 1, further comprising:

e) a controller adapted to move said feet into a third configuration in which said feet extend substantially parallel to each other and are angled relative to said longitudinal axis of said shaft.

3. A heart stabilization device according to claim 2, further comprising:

f) a lock which locks said feet in at least one of said second configuration and said third configurations.

4. A heart stabilization device according to claim 3, wherein:

said shaft includes a tubular outer member and an inner member longitudinally movable within said outer member, said outer member including a distal closer and said inner member including a distal clevis in which said arm assemblies are coupled, wherein said means for locking moves said inner member longitudinally relative to said outer member such that said clevis is compressed within said closer.

5. A heart stabilization device according to claim 1, wherein:

said controller includes a joystick in said handle, and cables extending from said stabilization arms to said joystick.

6. A heart stabilization device according to claim 1, wherein:

said joystick is rotatable about two axes.

7. A heart stabilization device according to claim 1, wherein:

said contact surfaces are in contact with each other when said feet are in said first configuration.

8. A heart stabilization device according to claim 7, wherein:

each said contact surface has a plurality of spikes and defines a plurality of holes, wherein when said contact surfaces are in contact with each other, said plurality of spikes of a first of said feet enter said plurality of holes of a second of said feet, and said plurality of spikes of said second of said feet enter said plurality of holes of said first of said feet.

9. A heart stabilization device according to claim 1, wherein:

each said contact surface has a plurality of spikes and defines a plurality of holes, wherein when said feet are in said first configuration said contact surfaces are in contact with each other, said plurality of spikes of a first of said feet enter said plurality of holes of a second of said feet, and said plurality of spikes of said second of said feet enter said plurality of holes of said first of said feet.

10. A heart stabilization device according to claim 1, wherein:

each said arm assembly includes an upper arm, a lower arm rotatable relative to said upper arm, a wrist rotatable about said lower arm, and said foot fixedly coupled to said wrist.

11. A heart stabilization device according to claim 10, wherein:

each said upper arm is rotatable about three axes.

12. A heart stabilization device according to claim 11, wherein:

first and second axes of said three axes about which each of said two upper arms rotate extend perpendicular to and through said longitudinal axis of said shaft, and a third axis of said three axes extends perpendicular to, but not through said longitudinal axis of said shaft.

13. A heart stabilization device according to claim 12, wherein:

for each arm assembly, said lower arm rotates relative to said upper arm about a fourth axis parallel to said first and second axes of said three axes.

14. A heart stabilization device according to claim 12, wherein:

said wrist rotates relative to said lower arm about a fifth axis which is perpendicular to each of first, second and third axes.

15. A heart stabilization device according to claim 10, wherein:

one of said two upper arms is rotatable about an axis which is not coaxial with any of said axes about which said other of said two upper arms is rotatable.

16. A heart stabilization device according to claim 10, wherein:

each said arm assembly includes a spring which urges said lower arm to rotate relative to its respective said upper arm.

17. A heart stabilization device according to claim 10, wherein:

each said arm assembly includes a spring which urges each said wrist to rotate relative to its respective said lower arm.

18. A heart stabilization device according to claim 10, further comprising:

interengaging slides which couple said arm assemblies together.

19. A heart stabilization device according to claim 18, further comprising:

a resilient member which urges said arm assemblies toward each other at or adjacent said interengaging slides.

20. A heart stabilization device according to claim 1, wherein:

each of said feet includes holds for suture or vessel loops.

21. A heart stabilization device according to claim 1, wherein:

each of said feet includes a medial scalloped portion.

22. A heart stabilization device according to claim 1, further comprising:

e) means for coupling said shaft to a port.

23. A heart stabilization device according to claim 22, wherein:

said means for coupling is adapted to permit said shaft to be angled relative to a longitudinal axis through said port.

24. A heart stabilization device, comprising:

a) a single shaft having a proximal end provided with a handle, a distal end, and defining a longitudinal axis; and b) a pair of stabilization arm assemblies at said distal end of said single shaft, each of said stabilization arms provided with a foot having a contact surface which is adapted to contact a surface of the heart;

c) a controller which moves said arm assemblies and said feet into selected configurations; and d) a lock which locks said arm assemblies and said feet in a selected configuration.

25. A heart stabilization device according to claim 24, wherein:

said contact surfaces of said feet are substantially parallel to each other in each of said selected configurations.

26. A heart stabilization device according to claim 24, wherein:

said shaft includes a tubular outer member and an inner member longitudinally movable within said outer member, said outer member including a distal closing element and said inner member including a distal clevis in which said arm assemblies are coupled, wherein said lock moves said inner member longitudinally relative to said outer member such that said clevis is compressed within said closing element and immobilizes said arm assemblies.

27. A heart stabilization device according to claim 26, wherein:

said inner member is coupled at its proximal end to a yoke, and a first cam is provided relative to said yoke such that operation of said cam moves said yoke to cause said inner member to move relative to said outer member.

28. A heart stabilization device according to claim 27, wherein:

said first cam is coupled to a lever provided on said handle, wherein rotation of said lever causes movement of said first cam.

29. A heart stabilization device according to claim 24, wherein:

said controller includes a joystick movable relative to said handle, and cables extending from said joystick to said arm assemblies.

30. A heart stabilization device according to claim 29, wherein:

said joystick is rotatable about two perpendicular axes.

31. A heart stabilization device according to claim 29, wherein:

said first cam is rotatably coupled to a second cam means for moving said joystick longitudinally in said handle, wherein longitudinal movement of said joystick in a proximal direction places sufficient tension on said cables to move and maintain said arm assemblies in an open configuration.

32. A heart stabilization device according to claim 24, further comprising:

e) means for coupling said shaft to a port.

33. A heart stabilization device according to claim 32, wherein:

said means for coupling is adapted to permit said shaft to be angled relative to a longitudinal axis through said port.

34. A heart stabilization device, comprising:

a) a shaft having a proximal end provided with a handle, a distal end, and defining a longitudinal axis;

b) a first and second stabilization arms at said distal end of said shaft, said first and second arms including resilient biasing means to urge said first and second arms together in an outstretched configuration in which portions of said arms are in contact;

c) a control element coupled to said handle; and d) a first cable extending from said first arm to said control element and a second cable extending from said second arm to said control element, wherein operation of said control element causes tensioning of said first and second cables such that said arms are moved from said outstretched configuration to a second configuration in which said arms are spaced apart.

35. A heart stabilization device according to claim 34, further comprising:

e) a lock which locks said arm assemblies in said second configuration.

36. A heart stabilization device according to claim 34, wherein:

said first and second stabilization arms are rotatable relative to said distal end of said shaft, and said control element is adapted to tension said first cable more than said second cable, such that when said control element tensions said first cable more than said second cable, said first and second arms are rotated relative to said shaft.

37. A heart stabilization device, comprising:

a) a shaft having a proximal end, a distal end, and defining a longitudinal axis; and b) a pair of stabilization arm assemblies at said distal end of said shaft, each of said stabilization arms provided with an upper arm rotatable relative to said distal end of said shaft in a first plane, and a lower arm rotatable relative to said upper arm in a second plane different than said first plane.

38. A heart stabilization device according to claim 37, further comprising:

c) a controller which manipulates rotation of said upper arms in said first plane.

39. A heart stabilization device according to claim 38, wherein:

said controller moves said first plane out of plane with said longitudinal axis.

40. A heart stabilization device, comprising:

a) a shaft having a proximal end, a distal end, and defining a longitudinal axis;

b) a pair of stabilization arm assemblies at said distal end of said shaft, each of said stabilization arms provided with a foot having a contact surface which is adapted to contact a surface of the heart; and c) means for coupling said shaft to a port adapted to be coupled directly to a human body, wherein said means for coupling is adapted to permit said shaft to be angled relative to a longitudinal axis through said port.

41. A heart stabilization device according to claim 40, wherein:

said means for coupling includes a housing defining a socket, a slit ball collet through which said shaft extends and which is rotatable within said socket, and a clamp which compresses said collet to substantially lock said shaft within said collet.

42. A heart stabilization device according to claim 40, wherein:
  said means for coupling further includes,
   i) a slotted tubular portion,
   ii) a bushing having a proximal portion with a first diameter, and a relatively distal portion with a second diameter greater than said first diameter, and
   iii) means for moving said bushing relative to said slotted tubular portion such that said portion of said bushing with said second diameter moves under said slotted tubular portion and increases an exterior diameter of said slotted tubular portion.

43. A heart stabilization device according to claim 40, wherein:
  said feet have a first configuration in which said feet extend substantially parallel to said longitudinal axis and are substantially in contact with each other, and a second configuration in which feet extend substantially parallel to said longitudinal axis and are displaced relative to each other.

* * * * *